(12) United States Patent
Sato et al.

(10) Patent No.: US 6,903,194 B1
(45) Date of Patent: Jun. 7, 2005

(54) ANTIBODY AGAINST HUMAN PARATHORMONE RELATED PEPTIDES

(75) Inventors: Koh Sato, Shizuoka (JP); Yuji Wakahara, Shizuoka (JP); Naohiro Yabuta, Shizuoka (JP)

(73) Assignee: Chungai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/269,332

(22) PCT Filed: Sep. 24, 1997

(86) PCT No.: PCT/JP97/03382

§ 371 (c)(1),
(2), (4) Date: Mar. 25, 1999

(87) PCT Pub. No.: WO98/13388

PCT Pub. Date: Apr. 2, 1998

(30) Foreign Application Priority Data

Sep. 26, 1996 (JP) ............................................. 8-255196
Jul. 24, 1997 (JP) ............................................. 9-214168

(51) Int. Cl.$^7$ ......................... C07K 1/10; A61K 39/395
(52) U.S. Cl. ............................. 530/387.1; 424/130.1; 424/178.1
(58) Field of Search .......................... 530/387.1, 388.1, 530/388.24, 388.85, 350, 300; 424/130.1, 178.1, 133.1, 134.1, 135.1, 141.1, 156.1, 158.1; 514/2

(56) References Cited

U.S. PATENT DOCUMENTS

| | | | |
|---|---|---|---|
| 5,001,223 A | 3/1991 | Rosenblatt et al. | ......... 530/324 |
| 5,217,896 A | 6/1993 | Kramer et al. | ......... 435/240.27 |
| 5,626,845 A | 5/1997 | Yoneda et al. | ............ 424/145.1 |
| 5,849,695 A | 12/1998 | Cohen et al. | .................. 514/12 |
| 5,993,817 A | 11/1999 | Yoneda et al. | ............ 424/158.1 |

FOREIGN PATENT DOCUMENTS

| | | |
|---|---|---|
| EP | 0 293 130 | 11/1988 |
| EP | 0293 158 | 11/1988 |
| EP | 0 449 405 | 10/1991 |
| EP | 0 811 383 | 12/1997 |
| EP | 0 878 201 A1 | 11/1998 |
| EP | 0 962 467 A1 | 12/1999 |
| EP | 1 004 313 A1 | 5/2000 |
| EP | 1 090 643 A1 | 4/2001 |
| JP | 2-207099 | 8/1990 |
| JP | 04-502408 | 5/1992 |
| JP | 04/228089 | 8/1992 |
| JP | 04-228089 A | 8/1992 |
| JP | 4-228089 | 8/1992 |
| JP | 7-165790 | 6/1995 |
| JP | 7-316195 | 12/1995 |
| JP | 11-80025 | 3/1999 |
| JP | 11-222440 | 8/1999 |
| JP | 2000-080100 | 3/2000 |
| WO | WO 89/11297 | 11/1989 |
| WO | WO 89/11298 | 11/1989 |
| WO | WO 90/07861 | 7/1990 |
| WO | WO 91/16928 | 11/1991 |
| WO | WO 92/00753 | 1/1992 |
| WO | WO 92/17602 | 10/1992 |
| WO | WO 92/19759 | 11/1992 |
| WO | WO 93/13133 | 7/1993 |
| WO | WO 94/11523 | 5/1994 |
| WO | WO 96/03437 | 2/1996 |
| WO | WO 96/39184 | 2/1996 |
| WO | WO 96/22790 | 8/1996 |
| WO | WO 96/26737 | 9/1996 |
| WO | WO 96/33735 | 10/1996 |
| WO | WO 98/13388 | 4/1998 |
| WO | WO 98/51329 | 11/1998 |
| WO | WO 99/57139 | 11/1999 |

OTHER PUBLICATIONS

Wong YW et al . J. Immunol. Apr. 1, 1995; 154(7):3351–8.*
Kemp, B. et al., Parathyroid hormone–related protein of malignancy: active synthetic fragments, Science, 238:1568–1570 (1987).
Baba, PTH/PTHrP, Clinical Calcium, 5:97–101 (1995) [Eng. transl.].
Natsume et al., Binding assay and analysis of kinetic parameters by BIAlcore biosensor, Experimental Medicine, 13:85–91 (1995) [Eng. transl.].
Shigeno, PTH/PTHrP, Clinical Calcium, 5:79–83 (1995) [Eng. transl.].
Ohtomo et al., Humanization of Mouse ONS–M21 Antibody with the Aid of Hybrid Variable Regions, Molecular Immunology, 32:407–416 (1995).
Coleman et al., Biochemical Mechanisms of Parathyroid Hormone Action, The Parathyroids, Basic and Clinical Concepts, 239–258 (1994).
Deftos et al., Utilization of a Potentially Universal Downstream Primer in the Rapid Identification and Characterization of Vλ Genes from Two New Human Vλ Gene Families, Scandanavian Journal of Immunology, 39:95–103 (1994).
Cuisinier et al., Mechanisms that generate human immunoglobulin diversity operate from the 8$^{th}$ week of gestation in fetal liver, European Journal of Immunology, 23:110–118 (1993).
Sato et al., Passive Immunization with Anti–Parathyroid Hormone–Related Protein Monoclonal Antibody Markedly Prolongs Survival Time of Hypercalcemic Nude Mice Bearing Transplanted Human PTHrP–Producing Tumors, Journal of Bone and Mineral Research, 8:849–860 (1993).

(Continued)

Primary Examiner—G. Nickol
Assistant Examiner—C. Yaen
(74) Attorney, Agent, or Firm—Finnegan, Henderson, Farabow, Garrett & Dunner, L.L.P.

(57) ABSTRACT

Disclosed are an antibody against human para-thyroid-hormone-related protein, a DNA coding for the antibody, a recombinant vector containing the DNA, a transformant transformed with the recombinant vector, a method for preparation of the antibody, and uses of the antibody.

11 Claims, 31 Drawing Sheets

OTHER PUBLICATIONS

Sato et al., Reshaping a Human Antibody to Inhibit the Interleukin 6–dependent Tumor Cell Growth, *Cancer Research*, 53:851–856 (1993).

Abou–Samra et al., Expression cloning of a common receptor for parathyroid hormone and parathyroid hormone–related peptide from rat osteoblast–like cells: A single receptor stimulates intracellular accumulation of both cAMP and inositol trisphosphates and increases intracellular free calcium, *Proceedings of the National Academy of Sciences*, 89:2732–2736 (1992).

Burtis, Parathyroid Hormone–Related Protein: Structure, Function, and Measurement, *Clinical Chemistry*, 38:2171–2183 (1992).

Carter et al., Humanization of an anti–p185$^{HER2}$ antibody for human cancer therapy, *Proceedings of the National Academy of Sciences*, 89:4285–4289 (1992).

Co et al., Chimeric and Humanized Antibodies with Specificity for the CD33 Antigen, *The Journal of immunology*, 148:1149–1154 (1992).

Co et al., Humanized antibodies for antiviral therapy, *Proceedings of the National Academy of Sciences*, 88:2869–2873 (1991).

Gorman et al., Reshaping a therapeutic CD4 antibody, *Proceedings of the National Academy of Sciences*, 88:4181–4185 (1991).

Jones et al., Rapid PCR–Cloning of Full–Length Mouse Immunoglobulin Variable Regions, *Bio/Technology*, 9:88–89 (1991).

Jüppner et al., A G Protein–Linked Receptor for Parathyroid Hormone and Parathyroid Hormone–Related Peptide, *Science*, 254:1024–1026 (1991).

Karlsson et al., Kinetic analysis of monoclonal antibody–antigen interactions with a new biosensor based analytical system, *Journal of Immunological Methods*, 145:229–240 (1991).

Kettleborough et al., Humanization of a mouse monoclonal antibody by CDR–grafting: the importance of framework residues on loop conformation, *Protein Engineering*, 4:773–783 (1991).

Maeda et al., Construction of reshaped human antibodies with HIV–neutralizing activity, *Human Antibodies and Hybridomas*, 2:124–134 (1991).

Tempest et al., Reshaping a Human Monoclonal Antibody to Inhibit Human Respiratory Syncytial Virus Infection in vivo. *Bio/Technology*, 9:266–271 (1991).

Mizushima et al., pEF–BOS, a powerful mammalian expression vector, *Nucleic Acids Research*, 18:5322 (1990).

Stewart et al., Clinical Review 16: Parathyroid Hormone–Related Proteins: Coming of Age in the 1990s, *The Journal of Clinical Endocrinology & Metabolism*, 71:1410–1414 (1990).

Belyavsky et al., PCR–based cDNA library construction: general cDNA libraries at the level of a few cells, *Nucleic Acids Research*, 17:2919–2933 (1989).

LoBuglio et al., Mouse/human chimeric monoclonal antibody in man: Kinetics and immune response, *Proceedings of the National Academy of Sciences*, 86:4220–4224 (1989).

Frohman et al., Rapid production of full–length cDNAs from rare transcripts: Amplification using a single gene–specific oligonucleotide primer, *Proceedings of the National Academy of Sciences*, 85:8998–9002 (1988).

Kukreja et al., Antibodies to Parathyroid Hormone–related Protein Lower Serum Calcium in Athymic Mouse Models of Malignancy–associated Hypercalcemia Due to Human Tumors, *The Journal of Clinical Investigation*, 82:1798–1802 (1988).

Riechmann et al., Reshaping human antibodies for therapy, *Nature*, 332:323–327 (1988).

Verhoeyen et al., Reshaping Human Antibodies: Grafting an Antilysozyme Activity, *Science*, 239:1534–1536 (1988).

Chomczynsk et al., Single–Step Method of RNA Isolation by Acid Guanidinium Thiocyanate–Phenol–Chloroform Extraction, *Analytical Biochemistry*, 162:156–159 (1987).

Chothia, Canonical Structures for the Hypervariable Regions of Immunoglobulins, *Journal of Molecular Biology*, 196:901–917 (1987).

Dariavach et al., Human immunoglobulin Cλ6 gene encodes the Kern$^+$Oz λ chain and $C_\lambda 4$ and $C_\lambda 5$ are pseudogenes, *Proceedings of the National Academy of Sciences*, 84:9074–9078 (1987).

Kemp et al., Parathyroid Hormone–Related Protein of Malignancy: Active Synthetic Fragments, *Science*, 238:1568–1570 (1987).

Kozak, At Least Six Nucleotides Preceding the AUG Initiator Codon Enhance Translation in Mammalian Cells, *Journal of Molecular Biology*, 196:947–950 (1987).

Moseley et al., Parathyroid hormone–related protein purified from a human lung cancer cell line, *Proceedings of the National Academy of Sciences*, 84: 5048–5052 (1987).

Sato et al., A highly sensitive bioassay for PTH using ROS 17/2.8 subclonal cells, *Acta Endocrinologica*, 116:113–120 (1987).

Suva et al., A Parathyroid Hormone–Related Protein Implicated in Malignant Hypercalcemia: Cloning and Expression, *Science*, 237:893–896 (1987).

Takahashi et al., Structure of Human Immunoglobulin Gamma Genes: Implications for Evolution of a Gene Family, *Cell*, 29:671–679 (1982).

de St. Groth et al., Production of Monoclonal Antibodies: Strategy and Tactics, *Journal of Immunological Methods*, 35:1–21 (1980).

Chirgwin et al., Isolation of Biologically Active Ribonucleic Acid from Sources Enriched in Ribonuclease, *Biochemistry*, 18:5294–5299 (1979).

Galfre et al., Rat + rat hybrid myelomas and a monoclonal anti–Fd portion of mouse IgG, *Nature*, 277: 131–133 (1979).

Kearney et al., A New Mouse Myeloma Cell Line That Has Lost Immunoglobulin Expression But Permits The Construction of Antibody–Secreting Hybrid Cell Lines, *The Journal of Immunology*, 123:1548–1550 (1979).

Mulligan et al., Synthesis of rabbit β–globin in cultured monkey kidney cells following infection with a SV40 β–globin recombinant genome, *Nature*, 277:108–114 (1979).

Shulman et al., A better cell line making hybridomas secreting specific antibodies, *Nature*, 276:269–270 (1978).

Trowbridge, Interspecies Spleen–Myeloma Hybrid Producing Monoclonal Antibodies Against Mouse Lymphocyte Surface Glycoprotein, T200, *The Journal of Experimental Medicine*, 148:313–323 (1978).

Yelton et al., Fusion of Mouse Myeloma and Spleen Cells, *Lymphocyte Hybridomas, Second Workshop on "Functional Properties of Tumors of T and B Lymphocytes,"* Sponsored by the National Cancer Institute (*NIH*) 1–7 (1978).

Köhler et al., Derivation of specific antibody–producing tissue culture and tumor lines by cell fusion, *European Journal of Immunology*, 6:511–519 (1976).

Margulies et al., Somatic Cell Hybridization of Mouse Myeloma Cells, *Cell*, 8:405–415 (1976).

Roe et al., A Photometric Method for the Determination of Inulin in Plasma and the Urine, *The Journal of Biological Chemistry*, 173:839–845 (1949).

C. Queen, et al., "A humanized antibody that binds to the interleukin 2 receptor," Proc. National Academy Science USA, 86:10029–10033 (Dec. 1989).

Mountain A, et al., Engineering antibodies for therapy (Article), Biotechnol Genet Eng Rev 10:1–142 (1992).

Mountain A, et al., Engineering antibodies for therapy (Abstract only), Biotechnol Genet Eng Rev 10:1–142 (1992).

Abou–Samra et al., Expression Cloning of a Common Receptor for Parathyroid Hormone and Parathyroid Hormone–Related Peptide from Rat Osteoblast–Like Cells: A Single Receptor Stimulates Intracellular Accumulation of Both cAMP and Inositol Trisphosphates and Increases Intracellular Free Calcium, *Proceedings of the National Academy of Sciences*, 89:2732–2736 (1992).

Baba, PTH/PTHrP, *Clinical Calcium*, 5:97–101 (1995) (English Translation).

Beck, S.A., et al., Lipolytic Factor Associated with Murine and Human Cancer Cachexia, *Journal of the National Cancer Institute*, 82:1922–1926 (1990).

Belyavsky et al., PCR–Based cDNA Library Construction: General cDNA Libraries at the Level of a Few Cells, *Nucleic Acids Research* 17:2919–2933(1989).

Benet et al., "Pharmacokinetics: The Dynamics of Drug Absorption, Distibution, and Elimination," In: *The Pharmacological Basis of Therapeutics*, $8^{th}$ edition, pp. 3–32 (1990).

Burtis, Parathyroid Hormone–Related Protein: Structure, Function, and Measurement, *Clinical Chemistry*, 38:2171–2183 (1992).

Carter et al. Humanization of an Anti–p185$^{HER2}$ Antibody for Human Cancer Theraphy, *Proceedings of the National Academy of Sciences*, 89:4285–4289 (1992).

Chirgwin et al., Isolation of Biologically Active Ribonucleic Acid From Sources Enriched in Ribonuclease, Biochemistry, 18:5294–5299 (1979).

Chomczynsk et al., Single–Step Method of RNA Isolation By Acid Guanidinium Thiocyanate–Phenol–Chloroform Extraction, *Analytical Biochemistry*, 162:156–159 (1987).

Chothia, Canonical Structures for the Hypervariable Regions of Immunoglobulins, *Journal of Molecular Biology*, 196:901–917 (1987).

Co et al., Chimeric and Humanized Antibodies with Specificity for the CD33 Antigen, *The Journal of Immunology*, 148:1149–1154 (1992).

Carter et al (PNAS USA 1992 May; 89:4285–4289).*

Co et al., Humanized Antibodies for Antiviral Therapy, *Proceedings of the National Academy of Sciences*, 88:2869–2873 (1991).

Coleman et al., Biochemical Mechanisms of Parathyroid Hormone Action, *The Parathyroids, Basic and Clinical Concepts*, 239–258 (1994).

Cuisinier et al., Mechanisms That Generate Human Immunoglobulin Diversity Operate From the $8^{th}$ Week of Gestation in Fetal Liver, *European Journal of Immunology*, 23:110–118 (1993).

Dariavach et al., Human Immunoglobulin $C_\lambda 6$ Gene Encodes the Kern OZ λ Chain and $C_\lambda 4$ and $C_\lambda 5$ are Pseudogenes, *Proceedings of the National Academy of Sciences*, 84:9074–9078 (1987).

Deftos et al., Utilization of a Potenitally Universal Downstream Primer in the Rapid Identification and Characterization of Vλ Genes From Two New Human Vλ Families, *Scandinavian Journal of Immunology*, 39:95–103 (1994).

de St. Groth, et al., Production of Monoclonal Antibodies: Strategy and Tactics, *Journal of Immunological Methods*, 35:1–21 (1980).

Dworkin, et al., Dietary Intake in Patients with Acquired Immunodeficiency Syndrome (AIDS), Patients with AIDS–Related Complex, and Serologically Positive Human Immunodeficiency Virus Patients: Correlations with Nutritional Status, *Journal of Parenteral and Enteral Nutrition*, 14:605–609 (1990).

Farmer et al., Speculations on the Design of Nonpeptidic Peptidomimetics, *TIPS*, 4:362–365, (1982).

Frohman et al., Rapid Production of Full–Length cDNAs From Rare Transcripts; Amplification Using a Single Gene-Specific Oligonucleotide Primer, *Proceedings of the National Academy of Sciences*, 85:8998–9002 (1988).

Galfre et al., Rat x Rat Hybrid Myelomas and A Monoclonal Anti–Fd Portion of Mouse IgG, *Nature*, 277:131–133 (1979).

Gorman et al., Reshaping a Therapeutic CD4 Antibody, *Proceeding of the National Academy of Sciences*, 88:4181–4185 (1991).

Hammond, M., et al., Respiratory Muscle Strength in Congestive Heart Failure, *Chest*, 98:1091–1094 (1990).

Hardman, J.G. et al. (ed.), Goodman & Gilman's, "The Pharmacological Basic of Therapeutics", Section XIII, Hormones and Hormone Anatgonists, McGraw–Hill Co. (USA) $9^{th}$ ed., at 1528–1529, (1995).

Hardman, J.G., et al., (ed.), "Agents Affecting Calcification and Bone Turnover" in Goodman and Gilman's "The Pharmacological Basis of Therapeutics", McGraw–Hill Co. (USA) $9^{th}$ ed., at 1523–1524 (1995).

Ikeda, K., "Molecular Biology of Parathyroid Hormone–Related Peptide", *Nihon Rinshou*, 53:37–45 (1995).

Ikeda, "Development of Novel Endocrinotherapy Targeting Cancer and Paraneoplastic Syndromes," Progress in Clinical Pharmacology, 16:155–161 (1995) (English Abstract).

Jones et al., Rapid PCR–Cloning of Full–Length Mouse Immunoglobulin Variable Regions, *Bio/Technology*, 9:88–89 (1991).

Jüppner et al., A G Protein–Linked Receptor for Parathyroid Hormone and Parathyroid Hormone–Related Peptide, *Science*, 254:1024–1026 (1991).

Kaji, H. et al., "Role of Dual Signal Transduction Systems in the Stimulation of Bone Resorption by Parathyroid Hormone–Related Peptide, The Direct Involvement of cAMP–Dependent Protein Kinase," *Horm. Metab. Res*. 25:421–424 (1993).

Kajimura, N., et al., Toxohormones Responsible for Cancer Cachexia Syndrome in Nude Mice Bearing Human Cancer Cell Lines, Cancer Chemother Pharmacol, 38:S48–S52 (1996).

Karlsson et al., Kinetic Analysis of Monclonal Antibody––Antigen Interactions with a New Biosensor Based Analytical System, *Journal of Immunological Methods*, 145:229–240 (1991).

Kato, A., et al. "Incisor Change Induced by Excessive PTHrP in Rats," Abstracts of 16th Meeting of Japanese Society of Toxicologic Pathology, p. 17 (2000) (English Translation).

Kearney et al., A New Mouse Myeloma Cell Line That Has Lost Immunoglobulin Expression But Permits the Construction of Antibody–Secreting Hybrid Cell Lines, *The Journal of Immunology*, 123:1548–1550 (1979).

Kemp et al., Parathyroid Hormone–Related Protein of Malignancy: Active Synthetic Fragments, Science 238:1568–1570 (1987).

Kettleborough et al., Humanization of a Mouse Monoclonal Antibody by CDR–Grafting: The Importance of Framework Residues on Loop Conformation, *Protein Engineering*, 4:773–738 (1991).

Köhler et al., Derivation of Specific Antibody–Producing Tissue Culture and Tumor Lines by Cell Fusion, *European Journal of Immunology*, 6:511–519 (1976).

Kozak, At Least Six Nucleotides Preceding the AUG Initiator Condon Enhance Translation in Mammalian Cells, *Journal of Molecular Biology*, 196:947–950 (1987).

Kukreja et al., Tumor Resection and Antibodies to Parathyroid Hormone–Related Protein Cause Similar Changes on Bone Histomorphometry in Hypercalcemia of Cancer, Endocrinology 127(1):305–310 (1990).

Kukreja et al., Antibodies to Parathyroid Hormone–Rated Protein Lower Serum Calcium in Athymic Mouse Models of Malignancy–Associated Hypercalcemia Due to Human Tumors, *The Journal of Clinical Investigation*, 82:1798–1802 (1988).

Liu, J.G. et al., "Developmental Role of PHTrP in Murine Molars," European Journal Oral Sciences 106 (suppl 1):143–146 (1998).

LoBuglio et al., Mouse/Human Chimeric Monclonal Antibody in Man; Kinetics and Immune Response, *Proceedings of the National Academy of Sciences*, 86:4220–4224 (1989).

Lundgren et al., "Parathyroid Hormone (1–34) Receptor–Binding and Second–Messenger Response in Rat incisor Odontoblasts", Calcif. Tissue Int., 62:255–259 (1998).

Maeda et al., Construction of Reshaped Human Antibodies with HIV–Neutralizing Activity, *Human Antibodies and Hybridomas*, 2:124–134 (1991).

Margulies et al., Somatic Cell Hybridization of Mouse Myeloma Cells, *Cell*, 8:405–415 (1976).

Marosi, C., et al., Fatal Encephalitis in a Patient with Chronic Graft–Versus Host Disease, *Bone Marrow Transplantation*, 6:53–57 (1990).

Mizushima et al., pEFBOS, A Powerful Mammalian Expression Vector, *Nucleic Acids Research*, 18:5322 (1990).

Morimoto, PTH/PTHrP, Clincial Calcium 5(12):50–54 (1995) (English Translation).

Moseley et al., Parathyroid Hormone–Related Protein Purified from A Human Lung Cancer Cell Line, *Proceedings of the National Academy of Sciences*, 84:5048–5052 (1987).

Mountain A. et al., "Engineering Antibodies for Therapy," In: Biotechnol Genet Eng Rev. 10:1–142 (1992).

Muller, J.M., et al., Uberwachung und Handhabung von Zentrainervosen und Intestinalen System zur Behandlung der Tumorkachexie, Langenbecks Arch Chir Suppl ll , pp. 261–265 (1990).

Mulligan et al, Synthesis of Rabbit β–globin in Cultured Monkey Kidney Cells Following Infection with a SV40 β–globin Recombinant Genome, Nature, 277:108–114 (1979).

Natsume et al., Binding Assay and Analysis of Kinetic Parameters by Bialcore Biosensor, *Experimental Medicine*, 13:85–91 (1995) (English Translation).

Ogata, E., "Parathyroid Hormone–Related Protein as a Potential Target of Therapy for Cancer–Associated Morbidity", Cancer, 88:2902–2911 (2000).

Ohtoma et al., Humanization of Mouse ONS–M21 Antibody with the Aid of Hybrid Variable Regions, *Molecular Immunology* 32:407–416 (1995).

Olstad, O.K., et al., Expression and Characterization of a Recombinant Human Parathyroid Partial Agonist with Antagonistic Properties: Gly–hPTH(–1→+84), *Peptides*, 16:1031–1037(1995).

Palmieri et al., "Muscle Calcium Accumulation in Muscular Dystrophy," *Intracell. Calcium Regul., Proc. Int. Symp.*, pp. 335–347 (1986).

Philbrick, et al, "Parathyroid Hormone–Related Protein is Required for Tooth Eruption", *Proc. Natl. Acad. Sci. USA*, 95:11846–11851 (1998).

Queen, C., et al., "A Humanized Antibody that Binds to the Interleukin 2 Receptor," *Proc. National Academy of Science USA*, 86:10029–10033(1989).

Riechmann et al., Reshaping Human Antibodies for Therapy, *Nature*, 332:323–327 (1988).

Roe et al., A Photometric Method for the Determination of Insulin in Plasma and Urine, *Journal of Biological Chemistry*, 173:839–845 (1949).

Rosen et al., "The effect of PTH Antagonist BIM–44002 on Serum Calcium and PTH Levels in Hypercalcemic Hyperparathyroid Patients", *Calcified Tissue International* , 61:455–459(1997).

Roubini, E. et al., Synthesis of Fully Active Biotinylated Analogues of Parathyroid Hormone and Parathyroid Hormone–Related Protein as Tools for the Characterization of Parathyroid Hormone Receptors, *Biochemistry*, 31:4026–4033 (1992).

Sato et al., Passive Immunization with Anti–Parathyroid Hormone–Related Protein Monclonal Anitbody Markedly Prolongs Survival Time of Hypercalemic Nude Mice Bearing Transplated Human PTHrP–Producing Tumors, Journal of Bone and Mineral Research, 8:849–860 (1993).

Sato et al, A Highly Sensitive Bioassay for PTH Using ROS 17/2.8 Subclonal Cells, *Acta Endocrinologica*, 116:113–120 (1987).

Sato, Malignancy–associated Hypercalcemia: Pathogenesis and Treatment, *Journal to Tokyo Women's Medical College*, 58(9):939–946 (1988) (English Abstract).

Saito et al., "Potential Involvement of PHTrP in Cancer Cachexia," *Journal of Cancer Research*, 90(Suppl.): Abstract No. 2195 (1999) (English Abstract).

Shigeno, C., PTH/PTHrP Receptor, Clinical Calicum, 5(3):79–83 (1995) (English Translation).

Shulman et al., A Better Cell Line for Making Hybridomas Secreting Specific Antibodies, *Nature*, 276:269–270 (1978).

Stewart et al., Clinical Review 16: Parathyroid Hormone–Related Proteins: Coming of Age in the 1990s, *Journal of Clincial Endocrinology and Metabolism*, 71:1410–1414 (1990).

Strewler, G.J., "The Physiology of Parathyroid Hormone–Related Protein," *The New England Journal of Medicine, Mechanisms of Disease* 342(3):177–185 (2000).

Sumiya et al. Hyercalcemia With Malignant Tumor, *Saishin Igaku*, 46(2):315–324 (1991).

Suva et al., A Parathyroid Hormone–Related Protein Implicated in Malignant Hypercalcemia: Cloning and Expression, *Science*, 237:893–896 (1987).

Takahashi et al., Structure of Human Immunoglobulin Gamma Genes: Implications for Evolution of a Gene Family, *Cell*, 29:671–679 (1982).

Takahashi et al., "Concentrations of Blood Parathyroid Hormone Related Protein (PTHrP) and Various Cytokines in Malignant Tumor Patients," *Record of the Japan Society of Clinical Biochemistry and Metabolism*, 35:107 (1998) (English Abstract).

Tanaka, R., Triple Paraneoplastic Syndrome of Hypercalcemia, Leukocytosis and Cachexia in Two Human Tumor Xerografts in Nude Mice, *Japanese Journal of Clinical Oncology*, 26:88–94 (1996).

Tempester et al., Reshaping A Human Monoclonal Antibody to Inhibit Human Respiraory Syncytial Virus infection in *vivo, Bio/Technology*, 9:266–271 (1991).

Tenorio et al., "An immunohistochemical Investigation of the Expression of Parathyroid Hormone Receptors in Rat Cementoblasts", *Archs Oral Biol.*, 41:299–305 (1996).

Sato et al., Reshaping a Human Antibody to Inhibit the Interleukin 6–dependent Tumor Cell Growth, Cancer Research, 53:851–856 (1993).

Tisdale, M.J., et al., Cancer Cachexia, *International Journal of Pancreatology*, 7:141–150 (1990).

Trowbridge, Interspecies Spleen–Myeloma Hybrid Producing Monoclonal Antibodies Against Mouse Lymphocyte Surface Glycoprotein, T200, *Jornal of Experimental Medicine*, 148:313–323 (1978).

Verhoeyen et al., Reshaping Human Antibodies; Grafting an Antilysoyme Activity, *Science* 239:1534–1536 (1988).

Weissglas, M. et al., Hypercalcemia and Cosecretion of Interleukin–6 and Parathyroid Hormone Related Peptide by a Human Renal Cell Carcinoma Implanted into Nude Mice, The Journal of Urology 153:854–857 (1995).

Wong et al., Modulation of Antibody Affinity by an Engineered Amino Acid Substitution, *J. Immunol.* 154:(7):3351–8 (1995).

Yamamoto, S., et al., "Parathyroid Hormone–Related Peptide–(1–34) PTHrP–(134) Induces Vasopressin Release from the Rat Supraoptic Nucleus *in Vitro* through a Novel Receptor Distinct from a Type I or Type II PTH/PTHrP Receptor", Endocrinology, 138(5):2066–2072 (1997).

Yelton et al., Fusion of Mouse Myeloma and Spleen Cells, Lymphocyte Hybridomas, Second Workshop on "Functional Properties of Tumors of T and B Lymphocytes," Sponsored by the National Cancer Institute (NIH) 1–7 (1978).

Yoshida et al., "Study of Abnormal Calcium Level in Myotonic Dystrophy–Part II: with Respect to Nephrogenous Cylic AMP and Immunoreactivity of Serum Parathyroid Hormone," The Japanese Endocrine Society Endocrine Journal, 64(7):539–547 (1988) (English Abstract).

Zbigniew Zylicz et al., Metabolic Response to Enteral Food in Different Phases of Cancer Cachexia in Rats, *Oncology*, 47:87–97 (1990).

* cited by examiner

Determination of Antigen-Binding Activity

Neutralizing Activity of
Humanized anti-PTHrP (1-34) Antibody

Neutralizing Activity of
Humanized anti-PTHrP (1-34) Antibody

Effect of Chimeric Antibody and Humanized Antibody on Hypercalcemic Model Animal (Nude Mouse Carrying Human Pancreatic Cancer PAN-7)

Effect of Chimeric Antibody and Humanized Antibody on Hypercalcemic Model Animal (Nude Mouse Carrying Human Pancreatic Cancer PAN-7)

Effect of Chimeric Antibody and Humanized Antibody on Hypercalcemic Model Animal (Nude Mouse Carrying Human Pancreatic Cancer PAN-7)

Effect of Chimeric Antibody and Humanized Antibody on Hypercalcemic Model Animal (Nude Mouse Carrying Human Lung Cancer LC-6-JCK)

Sensorgram of Mobilization of PTHrP (1-34+C) onto Sensor Tip

Effect on Body Temperature

SEQUENCE LISTING

<160> NUMBER OF SEQ ID NOS: 113

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 1
aaatagccct tgaccaggca                        20

<210> SEQ ID NO 2
<211> LENGTH: 38
<212> TYPE: DNA

```
<213> ORGANISM: Artificial Sequence
<220> FEATURE:
<223> OTHER INFORMATION: Description of Artificial Sequence: Synthetic
      DNA

<400> SEQUENCE: 2
ctggttcggc ccacctctga aggttccaga atcgatag                           38

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
ggatcccggg ccagtggata gacagatg                                     28

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
ggatcccggg tcagrggaag gtggraaca                                    29

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
gttttcccag tcacgac                                                 17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
caggaaacag ctatgac                                                 17

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
gtctaagctt ccaccatgaa acttcgggct c                                 31

<210> SEQ ID NO 8
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      DNA

<400> SEQUENCE: 8
tgttggatcc ctgcagagac agtgaccaga                                          30

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
gtctgaattc aagcttccac catggggttt gggctg                                   36

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
tttcccgggc ccttggtgga ggctgaggag acggtgacca g                             41

<210> SEQ ID NO 11
<211> LENGTH: 109
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
gtctgaattc aagcttagta cttggccagc ccaaggccaa ccccacggtc accctgttcc         60
cgccctcctc tgaggagctc aagccaaca aggccacact agtgtgtct                      109

<210> SEQ ID NO 12
<211> LENGTH: 110
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
ggtttggtgg tctccactcc cgccttgacg gggctgccat ctgccttcca ggccactgtc         60
acagctcccg ggtagaagtc actgatcaga cacactagtg tggccttgtt                    110

<210> SEQ ID NO 13
<211> LENGTH: 98
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
ggagtggaga ccaccaaacc ctccaaacag agcaacaaca agtacgcggc cagcagctac         60
ctgagcctga cgcccgagca gtggaagtcc cacagaag                                 98
```

<210> SEQ ID NO 14
<211> LENGTH: 106
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
tgttgaattc ttactatgaa cattctgtag gggccactgt cttctccacg gtgctccctt      60
catgcgtgac ctggcagctg tagcttctgt gggacttcca ctgctc                   106

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
gtctgaattc aagcttagta cttggccagc ccaaggccaa ccc                       43

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
tgttgaattc ttactatgaa                                                 20

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
caacaagtac gcggccagca gctacctgag cctgacgcc                            39

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
gtagctgctg gccgcgtact tgttgttgct ctgtttgga                            39

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
gtctgaattc aagcttagtc ctaggtcgaa ctgtggctgc accatc                    46

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
tgttgaattc ttactaacac tctcccctgt tgaa                                  34

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
gtctaagctt ccaccatggc ctggactcct ctctt                                 35

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
tgttgaattc agatctaact acttacctag gacagtgacc ttggtccc                   48

<210> SEQ ID NO 23
<211> LENGTH: 128
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
gtctaagctt ccaccatggg gtttgggctg agctgggttt tcctcgttgc tcttttaaga     60
ggtgtccagt gtcaggtgca gctggtggag tctgggggag gcgtggtcca gcctgggagg    120
tccctgag                                                             128

<210> SEQ ID NO 24
<211> LENGTH: 125
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
accattagta gtggtggtag ttacacctac tatccagaca gtgtgaaggg gcgattcacc     60
atctccagag acaattccaa gaacacgctg tatctgcaaa tgaacagcct gagagctgag    120
gacac                                                                125

<210> SEQ ID NO 25
<211> LENGTH: 132
<212> TYPE: DNA
<213> ORGANISM: Artificial Sequence

```
<220> FEATURE:
<223> OTHER INFORMATION: Description of Artificial Sequence: Synthetic
      DNA

<400> SEQUENCE: 25
ctaccaccac tactaatggt tgccacccac tccagcccct tgcctggagc ctggcggacc      60
caagacatgc catagctact gaaggtgaat ccagaggctg cacaggagag tctcagggac     120
ctcccaggct gg                                                         132

<210> SEQ ID NO 26
<211> LENGTH: 110
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
tgttggatcc ctgaggagac ggtgaccagg gttccctggc cccagtaagc aaagtaagtc      60
atagtagtct gtctcgcaca gtaatacaca gccgtgtcct cagctctcag                110

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
gtctaagctt ccaccatggg gtttgggctg                                       30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
tgttggatcc ctgaggagac ggtgaccagg                                       30

<210> SEQ ID NO 29
<211> LENGTH: 133
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
acaaagcttc caccatggcc tggactcctc tcttcttctt ctttgttctt cattgctcag      60
gttctttctc ccagcttgtg ctgactcaat cgccctctgc ctctgcctcc ctgggagcct     120
cggtcaagct cac                                                        133

<210> SEQ ID NO 30
<211> LENGTH: 118
<212> TYPE: DNA
<213> ORGANISM: Artificial Sequence
<220> FEATURE:
<223> OTHER INFORMATION: Description of Artificial Sequence: Synthetic
      DNA
```

```
<400> SEQUENCE: 30
agcaagatgg aagccacagc acaggtgatg ggattcctga tcgcttctca ggctccagct      60
ctggggctga gcgctacctc accatctcca gcctccagtc tgaggatgag gctgacta       118

<210> SEQ ID NO 31
<211> LENGTH: 128
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
ctgtggcttc catcttgctt aagtttcatc aagtaccgag ggcccttctc tggctgctgc      60
tgatgccatt caatggtgta cgtactgtgc tgactactca aggtgcaggt gagcttgacc     120
gaggctcc                                                              128

<210> SEQ ID NO 32
<211> LENGTH: 114
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
cttggatccg ggctgaccta ggacggtcag tttggtccct ccgccgaaca ccctcacaaa      60
ttgttcctta attgtatcac ccacaccaca gtaatagtca gcctcatcct caga           114

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
acaaagcttc caccatg                                                     17

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
cttggatccg ggctgacct                                                   19

<210> SEQ ID NO 35
<211> LENGTH: 75
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
cttggatccg ggctgaccta ggacggtcag tttggtccct ccgccgaaca cgtacacaaa      60
ttgttcctta attgt                                                       75
```

```
<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
aaaggatcct taagatccat caagtaccga gggggcttct ctg            43

<210> SEQ ID NO 37
<211> LENGTH: 46
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
acaaagctta gcgctacctc accatctcca gcctccagcc tgagga         46

<210> SEQ ID NO 38
<211> LENGTH: 111
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
cttggatccg ggctgaccta ggacggtcag tttggtccct ccgccgaaca cgtacacaaa     60 ttgttccttta attgtatcac ccacaccaca gatatagtca gcctcatcct c            111

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
cttctctggc tgctgctgat accattcaat ggtgtacgta ct             42

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
cgagggccct tctctggctg ctgctg                               26

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
gagaagggcc ctargtacst gatgrawctt aagca                     35
```

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: Synthetic
    DNA

<400> SEQUENCE: 42
cacgaattca ctatcgattc tggaaccttc agagg                35

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
    DNA

<400> SEQUENCE: 43
ggcttggagc tcctcaga                18

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
    DNA

<400> SEQUENCE: 44
gacagtggtt caaagttttt                20

<210> SEQ ID NO 45
<211> LENGTH: 118
<212> TYPE: PRT
<213> ORGANISM: Homo sapiens

<400> SEQUENCE: 45

Gln Leu Val Leu Thr Gln Ser Ser Ser Ala Ser Phe Ser Leu Gly Ala
 1               5                  10                  15

Ser Ala Lys Leu Thr Cys Thr Leu Ser Ser Gln His Ser Thr Tyr Thr
            20                  25                  30

Ile Glu Trp Tyr Gln Gln Pro Leu Lys Pro Pro Lys Tyr Val Met
        35                  40                  45

Asp Leu Lys Gln Asp Gly Ser His Ser Thr Gly Asp Gly Ile Pro Asp
    50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ala Met Tyr Ile Cys Gly Val Gly Asp
                85                  90                  95

Thr Ile Lys Glu Gln Phe Val Tyr Val Phe Gly Gly Gly Thr Lys Val
            100                 105                 110

Thr Val Leu Gly Gln Pro
        115

<210> SEQ ID NO 46
<211> LENGTH: 118
<212> TYPE: PRT
<213> ORGANISM: Homo sapiens

<400> SEQUENCE: 46

-continued

```
Glu Val Gln Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Ser Tyr
            20                  25                  30

Gly Met Ser Trp Ile Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Phe Tyr Cys
                85                  90                  95

Ala Arg Gln Thr Thr Met Thr Tyr Phe Ala Tyr Trp Gly Gln Gly Thr
            100                 105                 110

Leu Val Thr Val Ser Ala
        115
```

<210> SEQ ID NO 47
<211> LENGTH: 116
<212> TYPE: PRT
<213> ORGANISM: Homo sapiens

<400> SEQUENCE: 47

```
Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
            20                  25                  30

Ile Glu Trp His Gln Gln Pro Glu Lys Gly Pro Arg Tyr Leu Met
        35                  40                  45

Lys Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly
        115
```

<210> SEQ ID NO 48
<211> LENGTH: 118
<212> TYPE: PRT
<213> ORGANISM: Homo sapiens

<400> SEQUENCE: 48

```
Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Lys Tyr Leu Met
        35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80
```

```
Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Thr Lys Leu
            100                 105                 110

Thr Val Leu Gly Gln Pro
            115

<210> SEQ ID NO 49
<211> LENGTH: 118
<212> TYPE: PRT
<213> ORGANISM: Homo sapiens

<400> SEQUENCE: 49

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Lys Tyr Val Met
            35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Thr Lys Leu
            100                 105                 110

Thr Val Leu Gly Gln Pro
            115

<210> SEQ ID NO 50
<211> LENGTH: 118
<212> TYPE: PRT
<213> ORGANISM: Homo sapiens

<400> SEQUENCE: 50

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Arg Tyr Leu Met
            35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Thr Lys Leu
            100                 105                 110

Thr Val Leu Gly Gln Pro
            115

<210> SEQ ID NO 51
<211> LENGTH: 118
<212> TYPE: PRT
<213> ORGANISM: Homo sapiens
```

<400> SEQUENCE: 51

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Arg Tyr Val Met
        35                  40                  45

Asp Leu Lys Gln Asp Gly Ser His Ser Thr Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
            115

<210> SEQ ID NO 52
<211> LENGTH: 118
<212> TYPE: PRT
<213> ORGANISM: Homo sapiens

<400> SEQUENCE: 52

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Lys Tyr Leu Met
        35                  40                  45

Asp Leu Lys Gln Asp Gly Ser His Ser Thr Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
            115

<210> SEQ ID NO 53
<211> LENGTH: 118
<212> TYPE: PRT
<213> ORGANISM: Homo sapiens

<400> SEQUENCE: 53

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Arg Tyr Leu Met
        35                  40                  45

Asp Leu Lys Gln Asp Gly Ser His Ser Thr Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 54
<211> LENGTH: 118
<212> TYPE: PRT
<213> ORGANISM: Homo sapiens

<400> SEQUENCE: 54

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Lys Tyr Val Met
        35                  40                  45

Asp Leu Lys Gln Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 55
<211> LENGTH: 118
<212> TYPE: PRT
<213> ORGANISM: Homo sapiens

<400> SEQUENCE: 55

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Arg Tyr Val Met
        35                  40                  45

Asp Leu Lys Gln Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 56
<211> LENGTH: 118

-continued

<212> TYPE: PRT
<213> ORGANISM: Homo sapiens

<400> SEQUENCE: 56

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Thr Thr Met Thr Tyr Phe Ala Tyr Trp Gly Gln Gly Thr
            100                 105                 110

Leu Val Thr Val Ser Ser
        115

<210> SEQ ID NO 57
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: sig_peptide
<222> LOCATION: (1)..(57)
<221> NAME/KEY: mat_peptide
<222> LOCATION: (58)..(411)

<400> SEQUENCE: 57 atg aac ttc ggg ctc agc ttg att ttc ctt gcc ctc att tta aaa ggt      48
Met Asn Phe Gly Leu Ser Leu Ile Phe Leu Ala Leu Ile Leu Lys Gly
            -15                 -10                 -5 gtc cag tgt gag gtg caa ctg gtg gag tct ggg gga gac tta gtg aag      96
Val Gln Cys Glu Val Gln Leu Val Glu Ser Gly Gly Asp Leu Val Lys
        -1  1               5                   10 cct gga ggg tcc ctg aaa ctc tcc tgt gca gcc tct gga ttc act ttc     144
Pro Gly Gly Ser Leu Lys Leu Ser Cys Ala Ala Ser Gly Phe Thr Phe
    15                  20                  25 agt agc tat ggc atg tct tgg att cgc cag act cca gac aag agg ctg     192
Ser Ser Tyr Gly Met Ser Trp Ile Arg Gln Thr Pro Asp Lys Arg Leu
30                  35                  40                  45 gag tgg gtc gca acc att agt agt ggt ggt agt tac acc tac tat cca     240
Glu Trp Val Ala Thr Ile Ser Ser Gly Gly Ser Tyr Thr Tyr Tyr Pro
                50                  55                  60 gac agt gtg aag ggg cga ttc acc atc tcc aga gac aat gcc aag aac     288
Asp Ser Val Lys Gly Arg Phe Thr Ile Ser Arg Asp Asn Ala Lys Asn
            65                  70                  75 acc cta tac ctg caa atg agc agt ctg aag tct gag gac aca gcc atg     336
Thr Leu Tyr Leu Gln Met Ser Ser Leu Lys Ser Glu Asp Thr Ala Met
        80                  85                  90 ttt tac tgt gca aga cag act act atg act tac ttt gct tac tgg ggc     384
Phe Tyr Cys Ala Arg Gln Thr Thr Met Thr Tyr Phe Ala Tyr Trp Gly
    95                  100                 105 caa ggg act ctg gtc act gtc tct gca                                 411
Gln Gly Thr Leu Val Thr Val Ser Ala
110                 115

```
<210> SEQ ID NO 58
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: sig_peptide
<222> LOCATION: (1)..(57)
<221> NAME/KEY: mat_peptide
<222> LOCATION: (58)..(411)

<400> SEQUENCE: 58 atg ggg ttt ggg ctg agc tgg gtt ttc ctc gtt gct ctt tta aga ggt      48
Met Gly Phe Gly Leu Ser Trp Val Phe Leu Val Ala Leu Leu Arg Gly
            -15                 -10                  -5 gtc cag tgt cag gtg cag ctg gtg gag tct ggg gga ggc gtg gtc cag      96
Val Gln Cys Gln Val Gln Leu Val Glu Ser Gly Gly Gly Val Val Gln
        -1   1               5                   10 cct ggg agg tcc ctg aga ctc tcc tgt gca gcc tct gga ttc acc ttc     144
Pro Gly Arg Ser Leu Arg Leu Ser Cys Ala Ala Ser Gly Phe Thr Phe
        15                  20                  25 agt agc tat ggc atg tct tgg gtc cgc cag gct cca ggc aag ggg ctg     192
Ser Ser Tyr Gly Met Ser Trp Val Arg Gln Ala Pro Gly Lys Gly Leu
    30                  35                  40                  45 gag tgg gtg gca acc att agt agt ggt ggt agt tac acc tac tat cca     240
Glu Trp Val Ala Thr Ile Ser Ser Gly Gly Ser Tyr Thr Tyr Tyr Pro
                50                  55                  60 gac agt gtg aag ggg cga ttc acc atc tcc aga gac aat tcc aag aac     288
Asp Ser Val Lys Gly Arg Phe Thr Ile Ser Arg Asp Asn Ser Lys Asn
            65                  70                  75 acg ctg tat ctg caa atg aac agc ctg aga gct gag gac acg gct gtg     336
Thr Leu Tyr Leu Gln Met Asn Ser Leu Arg Ala Glu Asp Thr Ala Val
        80                  85                  90 tat tac tgt gcg aga cag act act atg act tac ttt gct tac tgg ggc     384
Tyr Tyr Cys Ala Arg Gln Thr Thr Met Thr Tyr Phe Ala Tyr Trp Gly
    95                  100                 105 cag gga acc ctg gtc acc gtc tcc tca                                 411
Gln Gly Thr Leu Val Thr Val Ser Ser
110                 115

<210> SEQ ID NO 59
<211> LENGTH: 11
<212> TYPE: PRT
<213> ORGANISM: Homo sapiens

<400> SEQUENCE: 59

Lys Ala Ser Gln Asp Val Asn Thr Ala Val Ala
 1               5                   10

<210> SEQ ID NO 60
<211> LENGTH: 7
<212> TYPE: PRT
<213> ORGANISM: Homo sapiens

<400> SEQUENCE: 60

Ser Ala Ser Asn Arg Tyr Thr
 1               5

<210> SEQ ID NO 61
<211> LENGTH: 9
<212> TYPE: PRT
<213> ORGANISM: Homo sapiens
```

```
<400> SEQUENCE: 61

Gln Gln His Tyr Ser Thr Pro Phe Thr
  1               5

<210> SEQ ID NO 62
<211> LENGTH: 5
<212> TYPE: PRT
<213> ORGANISM: Homo sapiens

<400> SEQUENCE: 62

Pro Tyr Trp Met Gln
  1               5

<210> SEQ ID NO 63
<211> LENGTH: 16
<212> TYPE: PRT
<213> ORGANISM: Homo sapiens

<400> SEQUENCE: 63

Ser Ile Phe Gly Asp Gly Asp Thr Arg Tyr Ser Gln Lys Phe Lys Gly
  1               5                  10                  15

<210> SEQ ID NO 64
<211> LENGTH: 11
<212> TYPE: PRT
<213> ORGANISM: Homo sapiens

<400> SEQUENCE: 64

Gly Leu Arg Arg Gly Gly Tyr Tyr Phe Asp Tyr
  1               5                  10

<210> SEQ ID NO 65
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: sig_peptide
<222> LOCATION: (1)..(57)
<221> NAME/KEY: mat_peptide
<222> LOCATION: (58)..(411)

<400> SEQUENCE: 65 atg gcc tgg act cct ctc ttc ttc ttt gtt ctt cat tgc tca ggt         48
Met Ala Trp Thr Pro Leu Phe Phe Phe Val Leu His Cys Ser Gly
            -15                 -10                  -5 tct ttc tcc caa ctt gtg ctc act cag tca tct tca gcc tct ttc tcc    96
Ser Phe Ser Gln Leu Val Leu Thr Gln Ser Ser Ser Ala Ser Phe Ser
        -1   1               5                  10 ctg gga gcc tca gca aaa ctc acg tgc acc ttg agt agt cag cac agt   144
Leu Gly Ala Ser Ala Lys Leu Thr Cys Thr Leu Ser Ser Gln His Ser
     15                  20                  25 acg tac acc att gaa tgg tat cag caa cag cca ctc aag cct cct aag   192
Thr Tyr Thr Ile Glu Trp Tyr Gln Gln Gln Pro Leu Lys Pro Pro Lys
 30                  35                  40                  45 tat gtg atg gat ctt aag caa gat gga agc cac agc aca ggt gat ggg   240
Tyr Val Met Asp Leu Lys Gln Asp Gly Ser His Ser Thr Gly Asp Gly
                 50                  55                  60 att cct gat cgc ttc tct gga tcc agc tct ggt gct gat cgc tac ctt   288
Ile Pro Asp Arg Phe Ser Gly Ser Ser Ser Gly Ala Asp Arg Tyr Leu
                     65                  70                  75 agc att tcc aac atc cag cca gaa gat gaa gca atg tac atc tgt ggt   336
```

```
Ser Ile Ser Asn Ile Gln Pro Glu Asp Glu Ala Met Tyr Ile Cys Gly
                80                  85                  90 gtg ggt gat aca att aag gaa caa ttt gtg tat gtt ttc ggc ggt ggg      384
Val Gly Asp Thr Ile Lys Glu Gln Phe Val Tyr Val Phe Gly Gly Gly
         95                 100                 105 acc aag gtc act gtc cta ggt cag ccc                                  411
Thr Lys Val Thr Val Leu Gly Gln Pro
110                 115

<210> SEQ ID NO 66
<211> LENGTH: 405
<212> TYPE: DNA
<213> ORGANISM: Homo sapiens
<220> FEATURE:
<221> NAME/KEY: CDS
<222> LOCATION: (1)..(405)
<221> NAME/KEY: sig_peptide
<222> LOCATION: (1)..(57)
<221> NAME/KEY: mat_peptide
<222> LOCATION: (58)..(405)

<400> SEQUENCE: 66 atg gcc tgg act cct ctc ttc ttc ttc ttt gtt ctt cat tgc tca ggt       48
Met Ala Trp Thr Pro Leu Phe Phe Phe Phe Val Leu His Cys Ser Gly
                -15                 -10                  -5 tct ttc tcc cag ctt gtg ctg act caa tcg ccc tct gcc tct gcc tcc       96
Ser Phe Ser Gln Leu Val Leu Thr Gln Ser Pro Ser Ala Ser Ala Ser
         -1   1                   5                  10 ctg gga gcc tcg gtc aag ctc acc tgc acc ttg agt agt cag cac agt      144
Leu Gly Ala Ser Val Lys Leu Thr Cys Thr Leu Ser Ser Gln His Ser
         15                  20                  25 acg tac acc att gaa tgg cat cag cag cag cca gag aag ggc cct cgg      192
Thr Tyr Thr Ile Glu Trp His Gln Gln Gln Pro Glu Lys Gly Pro Arg
 30                  35                  40                  45 tac ttg atg aaa ctt aag caa gat gga agc cac agc aca ggt gat ggg      240
Tyr Leu Met Lys Leu Lys Gln Asp Gly Ser His Ser Thr Gly Asp Gly
                 50                  55                  60 att cct gat cgc ttc tca ggc tcc agc tct ggg gct gag cgc tac ctc      288
Ile Pro Asp Arg Phe Ser Gly Ser Ser Ser Gly Ala Glu Arg Tyr Leu
             65                  70                  75 acc atc tcc agc ctc cag tct gag gat gag gct gac tat tac tgt ggt      336
Thr Ile Ser Ser Leu Gln Ser Glu Asp Glu Ala Asp Tyr Tyr Cys Gly
         80                  85                  90 gtg ggt gat aca att aag gaa caa ttt gtg tac gtg ttc ggc gga ggg      384
Val Gly Asp Thr Ile Lys Glu Gln Phe Val Tyr Val Phe Gly Gly Gly
         95                 100                 105 acc aaa ctg acc gtc cta ggt                                          405
Thr Lys Leu Thr Val Leu Gly
110                 115

<210> SEQ ID NO 67
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: sig_peptide
<222> LOCATION: (1)..(57)
<221> NAME/KEY: mat_peptide
<222> LOCATION: (58)..(411)

<400> SEQUENCE: 67 atg gcc tgg act cct ctc ttc ttc ttc ttt gtt ctt cat tgc tca ggt       48
Met Ala Trp Thr Pro Leu Phe Phe Phe Phe Val Leu His Cys Ser Gly
```

-continued

```
                    -15                 -10                  -5
tct ttc tcc cag ctt gtg ctg act caa tcg ccc tct gcc tct gcc tcc        96
Ser Phe Ser Gln Leu Val Leu Thr Gln Ser Pro Ser Ala Ser Ala Ser
         -1   1                   5                  10 ctg gga gcc tcg gtc aag ctc acc tgc acc ttg agt agt cag cac agt       144
Leu Gly Ala Ser Val Lys Leu Thr Cys Thr Leu Ser Ser Gln His Ser
     15                  20                  25 acg tac acc att gaa tgg tat cag cag cag cca gag aag ggc cct aag       192
Thr Tyr Thr Ile Glu Trp Tyr Gln Gln Gln Pro Glu Lys Gly Pro Lys
 30                  35                  40                  45 tac ctg atg gat ctt aag caa gat gga agc cac agc aca ggt gat ggg       240
Tyr Leu Met Asp Leu Lys Gln Asp Gly Ser His Ser Thr Gly Asp Gly
             50                  55                  60 att cct gat cgc ttc tca ggc tcc agc tct ggg gct gag cgc tac ctc       288
Ile Pro Asp Arg Phe Ser Gly Ser Ser Ser Gly Ala Glu Arg Tyr Leu
             65                  70                  75 acc atc tcc agc ctc cag tct gag gat gag gct gac tat tac tgt ggt       336
Thr Ile Ser Ser Leu Gln Ser Glu Asp Glu Ala Asp Tyr Tyr Cys Gly
             80                  85                  90 gtg ggt gat aca att aag gaa caa ttt gtg tac gtg ttc ggc gga ggg       384
Val Gly Asp Thr Ile Lys Glu Gln Phe Val Tyr Val Phe Gly Gly Gly
     95                 100                 105 acc aaa ctg acc gtc cta ggc cag ccc                                   411
Thr Lys Leu Thr Val Leu Gly Gln Pro
110                 115

<210> SEQ ID NO 68
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: sig_peptide
<222> LOCATION: (1)..(57)
<221> NAME/KEY: mat_peptide
<222> LOCATION: (58)..(411)

<400> SEQUENCE: 68 atg gcc tgg act cct ctc ttc ttc ttc ttt gtt ctt cat tgc tca ggt        48
Met Ala Trp Thr Pro Leu Phe Phe Phe Phe Val Leu His Cys Ser Gly
                    -15                 -10                  -5 tct ttc tcc cag ctt gtg ctg act caa tcg ccc tct gcc tct gcc tcc        96
Ser Phe Ser Gln Leu Val Leu Thr Gln Ser Pro Ser Ala Ser Ala Ser
         -1   1                   5                  10 ctg gga gcc tcg gtc aag ctc acc tgc acc ttg agt agt cag cac agt       144
Leu Gly Ala Ser Val Lys Leu Thr Cys Thr Leu Ser Ser Gln His Ser
     15                  20                  25 acg tac acc att gaa tgg tat cag cag cag cca gag aag ggc cct aag       192
Thr Tyr Thr Ile Glu Trp Tyr Gln Gln Gln Pro Glu Lys Gly Pro Lys
 30                  35                  40                  45 tac gtg atg gat ctt aag caa gat gga agc cac agc aca ggt gat ggg       240
Tyr Val Met Asp Leu Lys Gln Asp Gly Ser His Ser Thr Gly Asp Gly
             50                  55                  60 att cct gat cgc ttc tca ggc tcc agc tct ggg gct gag cgc tac ctc       288
Ile Pro Asp Arg Phe Ser Gly Ser Ser Ser Gly Ala Glu Arg Tyr Leu
             65                  70                  75 acc atc tcc agc ctc cag tct gag gat gag gct gac tat tac tgt ggt       336
Thr Ile Ser Ser Leu Gln Ser Glu Asp Glu Ala Asp Tyr Tyr Cys Gly
             80                  85                  90 gtg ggt gat aca att aag gaa caa ttt gtg tac gtg ttc ggc gga ggg       384
Val Gly Asp Thr Ile Lys Glu Gln Phe Val Tyr Val Phe Gly Gly Gly
```

-continued

```
                    95                  100                 105
acc aaa ctg acc gtc cta ggc cag ccc                                          411
Thr Lys Leu Thr Val Leu Gly Gln Pro
110                 115

<210> SEQ ID NO 69
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: sig_peptide
<222> LOCATION: (1)..(57)
<221> NAME/KEY: mat_peptide
<222> LOCATION: (58)..(411)

<400> SEQUENCE: 69 atg gcc tgg act cct ctc ttc ttc ttt gtt ctt cat tgc tca ggt                  48
Met Ala Trp Thr Pro Leu Phe Phe Phe Val Leu His Cys Ser Gly
            -15                 -10                 -5 tct ttc tcc cag ctt gtg ctg act caa tcg ccc tct gcc tct gcc tcc             96
Ser Phe Ser Gln Leu Val Leu Thr Gln Ser Pro Ser Ala Ser Ala Ser
        -1   1               5                   10 ctg gga gcc tcg gtc aag ctc acc tgc acc ttg agt agt cag cac agt            144
Leu Gly Ala Ser Val Lys Leu Thr Cys Thr Leu Ser Ser Gln His Ser
    15                  20                  25 acg tac acc att gaa tgg tat cag cag cag cca gag aag ggc cct agg            192
Thr Tyr Thr Ile Glu Trp Tyr Gln Gln Gln Pro Glu Lys Gly Pro Arg
30                  35                  40                  45 tac ctg atg gat ctt aag caa gat gga agc cac agc aca ggt gat ggg            240
Tyr Leu Met Asp Leu Lys Gln Asp Gly Ser His Ser Thr Gly Asp Gly
                50                  55                  60 att cct gat cgc ttc tca ggc tcc agc tct ggg gct gag cgc tac ctc            288
Ile Pro Asp Arg Phe Ser Gly Ser Ser Ser Gly Ala Glu Arg Tyr Leu
            65                  70                  75 acc atc tcc agc ctc cag tct gag gat gag gct gac tat tac tgt ggt            336
Thr Ile Ser Ser Leu Gln Ser Glu Asp Glu Ala Asp Tyr Tyr Cys Gly
        80                  85                  90 gtg ggt gat aca att aag gaa caa ttt gtg tac gtg ttc ggc gga ggg            384
Val Gly Asp Thr Ile Lys Glu Gln Phe Val Tyr Val Phe Gly Gly Gly
    95                  100                 105 acc aaa ctg acc gtc cta ggc cag ccc                                          411
Thr Lys Leu Thr Val Leu Gly Gln Pro
110                 115

<210> SEQ ID NO 70
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: sig_peptide
<222> LOCATION: (1)..(57)
<221> NAME/KEY: mat_peptide
<222> LOCATION: (58)..(411)

<400> SEQUENCE: 70 atg gcc tgg act cct ctc ttc ttc ttt gtt ctt cat tgc tca ggt                  48
Met Ala Trp Thr Pro Leu Phe Phe Phe Val Leu His Cys Ser Gly
            -15                 -10                 -5 tct ttc tcc cag ctt gtg ctg act caa tcg ccc tct gcc tct gcc tcc             96
Ser Phe Ser Gln Leu Val Leu Thr Gln Ser Pro Ser Ala Ser Ala Ser
        -1   1               5                   10
```

-continued

```
ctg gga gcc tcg gtc aag ctc acc tgc acc ttg agt agt cag cac agt      144
Leu Gly Ala Ser Val Lys Leu Thr Cys Thr Leu Ser Ser Gln His Ser
    15                  20                  25 acg tac acc att gaa tgg tat cag cag cag cca gag aag ggc cct agg      192
Thr Tyr Thr Ile Glu Trp Tyr Gln Gln Gln Pro Glu Lys Gly Pro Arg
30                  35                  40                  45 tac gtg atg gat ctt aag caa gat gga agc cac agc aca ggt gat ggg      240
Tyr Val Met Asp Leu Lys Gln Asp Gly Ser His Ser Thr Gly Asp Gly
                50                  55                  60 att cct gat cgc ttc tca ggc tcc agc tct ggg gct gag cgc tac ctc      288
Ile Pro Asp Arg Phe Ser Gly Ser Ser Ser Gly Ala Glu Arg Tyr Leu
            65                  70                  75 acc atc tcc agc ctc cag tct gag gat gag gct gac tat tac tgt ggt      336
Thr Ile Ser Ser Leu Gln Ser Glu Asp Glu Ala Asp Tyr Tyr Cys Gly
        80                  85                  90 gtg ggt gat aca att aag gaa caa ttt gtg tac gtg ttc ggc gga ggg      384
Val Gly Asp Thr Ile Lys Glu Gln Phe Val Tyr Val Phe Gly Gly Gly
    95                  100                 105 acc aaa ctg acc gtc cta ggc cag ccc                                  411
Thr Lys Leu Thr Val Leu Gly Gln Pro
110                 115
```

<210> SEQ ID NO 71
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: sig_peptide
<222> LOCATION: (1)..(57)
<221> NAME/KEY: mat_peptide
<222> LOCATION: (58)..(411)

<400> SEQUENCE: 71

```
atg gcc tgg act cct ctc ttc ttc ttc ttt gtt ctt cat tgc tca ggt       48
Met Ala Trp Thr Pro Leu Phe Phe Phe Phe Val Leu His Cys Ser Gly
                -15                 -10                 -5 tct ttc tcc cag ctt gtg ctg act caa tcg ccc tct gcc tct gcc tcc       96
Ser Phe Ser Gln Leu Val Leu Thr Gln Ser Pro Ser Ala Ser Ala Ser
        -1  1               5                   10 ctg gga gcc tcg gtc aag ctc acc tgc acc ttg agt agt cag cac agt      144
Leu Gly Ala Ser Val Lys Leu Thr Cys Thr Leu Ser Ser Gln His Ser
    15                  20                  25 acg tac acc att gaa tgg tat cag cag cag cca gag aag ggc cct aag      192
Thr Tyr Thr Ile Glu Trp Tyr Gln Gln Gln Pro Glu Lys Gly Pro Lys
30                  35                  40                  45 tac ctg atg gat ctt aag caa gat gga agc cac agc aca ggt gat ggg      240
Tyr Leu Met Asp Leu Lys Gln Asp Gly Ser His Ser Thr Gly Asp Gly
                50                  55                  60 att cct gat cgc ttc tca ggc tcc agc tct ggg gct gag cgc tac ctc      288
Ile Pro Asp Arg Phe Ser Gly Ser Ser Ser Gly Ala Glu Arg Tyr Leu
            65                  70                  75 acc atc tcc agc ctc cag tct gag gat gag gct gac tat atc tgt ggt      336
Thr Ile Ser Ser Leu Gln Ser Glu Asp Glu Ala Asp Tyr Ile Cys Gly
        80                  85                  90 gtg ggt gat aca att aag gaa caa ttt gtg tac gtg ttc ggc gga ggg      384
Val Gly Asp Thr Ile Lys Glu Gln Phe Val Tyr Val Phe Gly Gly Gly
    95                  100                 105 acc aaa ctg acc gtc cta ggc cag ccc                                  411
Thr Lys Leu Thr Val Leu Gly Gln Pro
110                 115
```

```
<210> SEQ ID NO 72
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: sig_peptide
<222> LOCATION: (1)..(57)
<221> NAME/KEY: mat_peptide
<222> LOCATION: (58)..(411)

<400> SEQUENCE: 72 atg gcc tgg act cct ctc ttc ttc ttc ttt gtt ctt cat tgc tca ggt      48
Met Ala Trp Thr Pro Leu Phe Phe Phe Phe Val Leu His Cys Ser Gly
                -15                 -10                  -5 tct ttc tcc cag ctt gtg ctg act caa tcg ccc tct gcc tct gcc tcc      96
Ser Phe Ser Gln Leu Val Leu Thr Gln Ser Pro Ser Ala Ser Ala Ser
             -1   1               5                  10 ctg gga gcc tcg gtc aag ctc acc tgc acc ttg agt agt cag cac agt     144
Leu Gly Ala Ser Val Lys Leu Thr Cys Thr Leu Ser Ser Gln His Ser
         15                  20                  25 acg tac acc att gaa tgg tat cag cag cag cca gag aag ggc cct agg     192
Thr Tyr Thr Ile Glu Trp Tyr Gln Gln Gln Pro Glu Lys Gly Pro Arg
 30                  35                  40                  45 tac ctg atg gat ctt aag caa gat gga agc cac agc aca ggt gat ggg     240
Tyr Leu Met Asp Leu Lys Gln Asp Gly Ser His Ser Thr Gly Asp Gly
                 50                  55                  60 att cct gat cgc ttc tca ggc tcc agc tct ggg gct gag cgc tac ctc     288
Ile Pro Asp Arg Phe Ser Gly Ser Ser Ser Gly Ala Glu Arg Tyr Leu
             65                  70                  75 acc atc tcc agc ctc cag tct gag gat gag gct gac tat atc tgt ggt     336
Thr Ile Ser Ser Leu Gln Ser Glu Asp Glu Ala Asp Tyr Ile Cys Gly
         80                  85                  90 gtg ggt gat aca att aag gaa caa ttt gtg tac gtg ttc ggc gga ggg     384
Val Gly Asp Thr Ile Lys Glu Gln Phe Val Tyr Val Phe Gly Gly Gly
     95                 100                 105 acc aaa ctg acc gtc cta ggc cag ccc                                 411
Thr Lys Leu Thr Val Leu Gly Gln Pro
110                 115

<210> SEQ ID NO 73
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: sig_peptide
<222> LOCATION: (1)..(57)
<221> NAME/KEY: mat_peptide
<222> LOCATION: (58)..(411)

<400> SEQUENCE: 73 atg gcc tgg act cct ctc ttc ttc ttc ttt gtt ctt cat tgc tca ggt      48
Met Ala Trp Thr Pro Leu Phe Phe Phe Phe Val Leu His Cys Ser Gly
                -15                 -10                  -5 tct ttc tcc cag ctt gtg ctg act caa tcg ccc tct gcc tct gcc tcc      96
Ser Phe Ser Gln Leu Val Leu Thr Gln Ser Pro Ser Ala Ser Ala Ser
             -1   1               5                  10 ctg gga gcc tcg gtc aag ctc acc tgc acc ttg agt agt cag cac agt     144
Leu Gly Ala Ser Val Lys Leu Thr Cys Thr Leu Ser Ser Gln His Ser
         15                  20                  25
```

-continued

```
acg tac acc att gaa tgg tat cag cag cag cca gag aag ggc cct aag      192
Thr Tyr Thr Ile Glu Trp Tyr Gln Gln Gln Pro Glu Lys Gly Pro Lys
 30              35                  40                  45 tac gtg atg gat ctt aag caa gat gga agc cac agc aca ggt gat ggg      240
Tyr Val Met Asp Leu Lys Gln Asp Gly Ser His Ser Thr Gly Asp Gly
             50                  55                  60 att cct gat cgc ttc tca ggc tcc agc tct ggg gct gag cgc tac ctc      288
Ile Pro Asp Arg Phe Ser Gly Ser Ser Ser Gly Ala Glu Arg Tyr Leu
         65                  70                  75 acc atc tcc agc ctc cag tct gag gat gag gct gac tat atc tgt ggt      336
Thr Ile Ser Ser Leu Gln Ser Glu Asp Glu Ala Asp Tyr Ile Cys Gly
     80                  85                  90 gtg ggt gat aca att aag gaa caa ttt gtg tac gtg ttc ggc gga ggg      384
Val Gly Asp Thr Ile Lys Glu Gln Phe Val Tyr Val Phe Gly Gly Gly
 95                 100                 105 acc aaa ctg acc gtc cta ggc cag ccc                                  411
Thr Lys Leu Thr Val Leu Gly Gln Pro
110             115
```

<210> SEQ ID NO 74
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: sig_peptide
<222> LOCATION: (1)..(57)
<221> NAME/KEY: mat_peptide
<222> LOCATION: (58)..(411)

<400> SEQUENCE: 74

```
atg gcc tgg act cct ctc ttc ttc ttt gtt ctt cat tgc tca ggt           48
Met Ala Trp Thr Pro Leu Phe Phe Phe Val Leu His Cys Ser Gly
                -15                 -10                 -5 tct ttc tcc cag ctt gtg ctg act caa tcg ccc tct gcc tct gcc tcc       96
Ser Phe Ser Gln Leu Val Leu Thr Gln Ser Pro Ser Ala Ser Ala Ser
         -1  1               5                  10 ctg gga gcc tcg gtc aag ctc acc tgc acc ttg agt agt cag cac agt      144
Leu Gly Ala Ser Val Lys Leu Thr Cys Thr Leu Ser Ser Gln His Ser
 15                  20                  25 acg tac acc att gaa tgg tat cag cag cag cca gag aag ggc cct agg      192
Thr Tyr Thr Ile Glu Trp Tyr Gln Gln Gln Pro Glu Lys Gly Pro Arg
 30              35                  40                  45 tac gtg atg gat ctt aag caa gat gga agc cac agc aca ggt gat ggg      240
Tyr Val Met Asp Leu Lys Gln Asp Gly Ser His Ser Thr Gly Asp Gly
             50                  55                  60 att cct gat cgc ttc tca ggc tcc agc tct ggg gct gag cgc tac ctc      288
Ile Pro Asp Arg Phe Ser Gly Ser Ser Ser Gly Ala Glu Arg Tyr Leu
         65                  70                  75 acc atc tcc agc ctc cag tct gag gat gag gct gac tat atc tgt ggt      336
Thr Ile Ser Ser Leu Gln Ser Glu Asp Glu Ala Asp Tyr Ile Cys Gly
     80                  85                  90 gtg ggt gat aca att aag gaa caa ttt gtg tac gtg ttc ggc gga ggg      384
Val Gly Asp Thr Ile Lys Glu Gln Phe Val Tyr Val Phe Gly Gly Gly
 95                 100                 105 acc aaa ctg acc gtc cta ggc cag ccc                                  411
Thr Lys Leu Thr Val Leu Gly Gln Pro
110             115
```

<210> SEQ ID NO 75
<211> LENGTH: 34
<212> TYPE: PRT

-continued

<213> ORGANISM: Homo sapiens

<400> SEQUENCE: 75

```
Ala Val Ser Glu His Gln Leu Leu His Asp Lys Gly Lys Ser Ile Gln
  1               5                  10                  15

Asp Leu Arg Arg Arg Phe Phe Leu His Leu Ile Ala Glu Ile His
             20                  25                  30

Thr Ala
```

<210> SEQ ID NO 76
<211> LENGTH: 137
<212> TYPE: PRT
<213> ORGANISM: Homo sapiens

<400> SEQUENCE: 76

```
Met Asn Phe Gly Leu Ser Leu Ile Phe Leu Ala Leu Ile Leu Lys Gly
                -15                 -10                  -5

Val Gln Cys Glu Val Gln Leu Val Glu Ser Gly Gly Asp Leu Val Lys
             -1   1               5                  10

Pro Gly Gly Ser Leu Lys Leu Ser Cys Ala Ala Ser Gly Phe Thr Phe
         15                  20                  25

Ser Ser Tyr Gly Met Ser Trp Ile Arg Gln Thr Pro Asp Lys Arg Leu
 30                  35                  40                  45

Glu Trp Val Ala Thr Ile Ser Ser Gly Gly Ser Tyr Thr Tyr Tyr Pro
                 50                  55                  60

Asp Ser Val Lys Gly Arg Phe Thr Ile Ser Arg Asp Asn Ala Lys Asn
             65                  70                  75

Thr Leu Tyr Leu Gln Met Ser Ser Leu Lys Ser Glu Asp Thr Ala Met
         80                  85                  90

Phe Tyr Cys Ala Arg Gln Thr Thr Met Thr Tyr Phe Ala Tyr Trp Gly
     95                 100                 105

Gln Gly Thr Leu Val Thr Val Ser Ala
110                 115
```

<210> SEQ ID NO 77
<211> LENGTH: 137
<212> TYPE: PRT
<213> ORGANISM: Homo sapiens

<400> SEQUENCE: 77

```
Met Gly Phe Gly Leu Ser Trp Val Phe Leu Val Ala Leu Leu Arg Gly
                -15                 -10                  -5

Val Gln Cys Gln Val Gln Leu Val Glu Ser Gly Gly Gly Val Val Gln
             -1   1               5                  10

Pro Gly Arg Ser Leu Arg Leu Ser Cys Ala Ala Ser Gly Phe Thr Phe
         15                  20                  25

Ser Ser Tyr Gly Met Ser Trp Val Arg Gln Ala Pro Gly Lys Gly Leu
 30                  35                  40                  45

Glu Trp Val Ala Thr Ile Ser Ser Gly Gly Ser Tyr Thr Tyr Tyr Pro
                 50                  55                  60

Asp Ser Val Lys Gly Arg Phe Thr Ile Ser Arg Asp Asn Ser Lys Asn
             65                  70                  75

Thr Leu Tyr Leu Gln Met Asn Ser Leu Arg Ala Glu Asp Thr Ala Val
         80                  85                  90

Tyr Tyr Cys Ala Arg Gln Thr Thr Met Thr Tyr Phe Ala Tyr Trp Gly
     95                 100                 105
```

-continued

```
Gln Gly Thr Leu Val Thr Val Ser Ser
110             115

<210> SEQ ID NO 78
<211> LENGTH: 137
<212> TYPE: PRT
<213> ORGANISM: Homo sapiens

<400> SEQUENCE: 78

Met Ala Trp Thr Pro Leu Phe Phe Phe Val Leu His Cys Ser Gly
                -15             -10             -5

Ser Phe Ser Gln Leu Val Leu Thr Gln Ser Ser Ala Ser Phe Ser
        -1  1           5               10

Leu Gly Ala Ser Ala Lys Leu Thr Cys Thr Leu Ser Ser Gln His Ser
    15              20              25

Thr Tyr Thr Ile Glu Trp Tyr Gln Gln Pro Leu Lys Pro Pro Lys
    30              35              40              45

Tyr Val Met Asp Leu Lys Gln Asp Gly Ser His Ser Thr Gly Asp Gly
                50              55              60

Ile Pro Asp Arg Phe Ser Gly Ser Ser Ser Gly Ala Asp Arg Tyr Leu
            65              70              75

Ser Ile Ser Asn Ile Gln Pro Glu Asp Glu Ala Met Tyr Ile Cys Gly
        80              85              90

Val Gly Asp Thr Ile Lys Glu Gln Phe Val Tyr Val Phe Gly Gly Gly
        95              100             105

Thr Lys Val Thr Val Leu Gly Gln Pro
110             115

<210> SEQ ID NO 79
<211> LENGTH: 135
<212> TYPE: PRT
<213> ORGANISM: Homo sapiens

<400> SEQUENCE: 79

Met Ala Trp Thr Pro Leu Phe Phe Phe Val Leu His Cys Ser Gly
                -15             -10             -5

Ser Phe Ser Gln Leu Val Leu Thr Gln Ser Pro Ser Ala Ser Ala Ser
        -1  1           5               10

Leu Gly Ala Ser Val Lys Leu Thr Cys Thr Leu Ser Ser Gln His Ser
    15              20              25

Thr Tyr Thr Ile Glu Trp His Gln Gln Pro Glu Lys Gly Pro Arg
    30              35              40              45

Tyr Leu Met Lys Leu Lys Gln Asp Gly Ser His Ser Thr Gly Asp Gly
                50              55              60

Ile Pro Asp Arg Phe Ser Gly Ser Ser Ser Gly Ala Glu Arg Tyr Leu
            65              70              75

Thr Ile Ser Ser Leu Gln Ser Glu Asp Glu Ala Asp Tyr Tyr Cys Gly
        80              85              90

Val Gly Asp Thr Ile Lys Glu Gln Phe Val Tyr Val Phe Gly Gly Gly
        95              100             105

Thr Lys Leu Thr Val Leu Gly
110             115

<210> SEQ ID NO 80
<211> LENGTH: 137
<212> TYPE: PRT
<213> ORGANISM: Homo sapiens
```

-continued

```
<400> SEQUENCE: 80

Met Ala Trp Thr Pro Leu Phe Phe Phe Val Leu His Cys Ser Gly
            -15                 -10                 -5

Ser Phe Ser Gln Leu Val Leu Thr Gln Ser Pro Ser Ala Ser Ala Ser
         -1   1               5                  10

Leu Gly Ala Ser Val Lys Leu Thr Cys Thr Leu Ser Ser Gln His Ser
         15                  20                  25

Thr Tyr Thr Ile Glu Trp Tyr Gln Gln Pro Glu Lys Gly Pro Lys
 30                  35                  40                  45

Tyr Leu Met Asp Leu Lys Gln Asp Gly Ser His Ser Thr Gly Asp Gly
                 50                  55                  60

Ile Pro Asp Arg Phe Ser Gly Ser Ser Ser Gly Ala Glu Arg Tyr Leu
                 65                  70                  75

Thr Ile Ser Ser Leu Gln Ser Glu Asp Glu Ala Asp Tyr Tyr Cys Gly
             80                  85                  90

Val Gly Asp Thr Ile Lys Glu Gln Phe Val Tyr Val Phe Gly Gly Gly
         95                  100                 105

Thr Lys Leu Thr Val Leu Gly Gln Pro
110                 115

<210> SEQ ID NO 81
<211> LENGTH: 137
<212> TYPE: PRT
<213> ORGANISM: Homo sapiens

<400> SEQUENCE: 81

Met Ala Trp Thr Pro Leu Phe Phe Phe Val Leu His Cys Ser Gly
            -15                 -10                 -5

Ser Phe Ser Gln Leu Val Leu Thr Gln Ser Pro Ser Ala Ser Ala Ser
         -1   1               5                  10

Leu Gly Ala Ser Val Lys Leu Thr Cys Thr Leu Ser Ser Gln His Ser
         15                  20                  25

Thr Tyr Thr Ile Glu Trp Tyr Gln Gln Pro Glu Lys Gly Pro Lys
 30                  35                  40                  45

Tyr Val Met Asp Leu Lys Gln Asp Gly Ser His Ser Thr Gly Asp Gly
                 50                  55                  60

Ile Pro Asp Arg Phe Ser Gly Ser Ser Ser Gly Ala Glu Arg Tyr Leu
                 65                  70                  75

Thr Ile Ser Ser Leu Gln Ser Glu Asp Glu Ala Asp Tyr Tyr Cys Gly
             80                  85                  90

Val Gly Asp Thr Ile Lys Glu Gln Phe Val Tyr Val Phe Gly Gly Gly
         95                  100                 105

Thr Lys Leu Thr Val Leu Gly Gln Pro
110                 115

<210> SEQ ID NO 82
<211> LENGTH: 137
<212> TYPE: PRT
<213> ORGANISM: Homo sapiens

<400> SEQUENCE: 82

Met Ala Trp Thr Pro Leu Phe Phe Phe Val Leu His Cys Ser Gly
            -15                 -10                 -5

Ser Phe Ser Gln Leu Val Leu Thr Gln Ser Pro Ser Ala Ser Ala Ser
         -1   1               5                  10

Leu Gly Ala Ser Val Lys Leu Thr Cys Thr Leu Ser Ser Gln His Ser
```

-continued

```
                 15                  20                  25
Thr Tyr Thr Ile Glu Trp Tyr Gln Gln Gln Pro Glu Lys Gly Pro Arg
 30                  35                  40                  45

Tyr Leu Met Asp Leu Lys Gln Asp Gly Ser His Ser Thr Gly Asp Gly
                 50                  55                  60

Ile Pro Asp Arg Phe Ser Gly Ser Ser Gly Ala Glu Arg Tyr Leu
                 65                  70                  75

Thr Ile Ser Ser Leu Gln Ser Glu Asp Glu Ala Asp Tyr Tyr Cys Gly
                 80                  85                  90

Val Gly Asp Thr Ile Lys Glu Gln Phe Val Tyr Val Phe Gly Gly Gly
                 95                 100                 105

Thr Lys Leu Thr Val Leu Gly Gln Pro
110                 115

<210> SEQ ID NO 83
<211> LENGTH: 137
<212> TYPE: PRT
<213> ORGANISM: Homo sapiens

<400> SEQUENCE: 83

Met Ala Trp Thr Pro Leu Phe Phe Phe Val Leu His Cys Ser Gly
                -15                 -10                  -5

Ser Phe Ser Gln Leu Val Leu Thr Gln Ser Pro Ser Ala Ser Ala Ser
         -1   1                   5                  10

Leu Gly Ala Ser Val Lys Leu Thr Cys Thr Leu Ser Ser Gln His Ser
                 15                  20                  25

Thr Tyr Thr Ile Glu Trp Tyr Gln Gln Gln Pro Glu Lys Gly Pro Arg
 30                  35                  40                  45

Tyr Val Met Asp Leu Lys Gln Asp Gly Ser His Ser Thr Gly Asp Gly
                 50                  55                  60

Ile Pro Asp Arg Phe Ser Gly Ser Ser Gly Ala Glu Arg Tyr Leu
                 65                  70                  75

Thr Ile Ser Ser Leu Gln Ser Glu Asp Glu Ala Asp Tyr Tyr Cys Gly
                 80                  85                  90

Val Gly Asp Thr Ile Lys Glu Gln Phe Val Tyr Val Phe Gly Gly Gly
                 95                 100                 105

Thr Lys Leu Thr Val Leu Gly Gln Pro
110                 115

<210> SEQ ID NO 84
<211> LENGTH: 137
<212> TYPE: PRT
<213> ORGANISM: Homo sapiens

<400> SEQUENCE: 84

Met Ala Trp Thr Pro Leu Phe Phe Phe Val Leu His Cys Ser Gly
                -15                 -10                  -5

Ser Phe Ser Gln Leu Val Leu Thr Gln Ser Pro Ser Ala Ser Ala Ser
         -1   1                   5                  10

Leu Gly Ala Ser Val Lys Leu Thr Cys Thr Leu Ser Ser Gln His Ser
                 15                  20                  25

Thr Tyr Thr Ile Glu Trp Tyr Gln Gln Gln Pro Glu Lys Gly Pro Lys
 30                  35                  40                  45

Tyr Leu Met Asp Leu Lys Gln Asp Gly Ser His Ser Thr Gly Asp Gly
                 50                  55                  60

Ile Pro Asp Arg Phe Ser Gly Ser Ser Ser Gly Ala Glu Arg Tyr Leu
```

```
                65                  70                  75
Thr Ile Ser Ser Leu Gln Ser Glu Asp Glu Ala Asp Tyr Ile Cys Gly
            80                  85                  90

Val Gly Asp Thr Ile Lys Glu Gln Phe Val Tyr Val Phe Gly Gly Gly
        95                  100                 105

Thr Lys Leu Thr Val Leu Gly Gln Pro
110                 115

<210> SEQ ID NO 85
<211> LENGTH: 137
<212> TYPE: PRT
<213> ORGANISM: Homo sapiens

<400> SEQUENCE: 85

Met Ala Trp Thr Pro Leu Phe Phe Phe Val Leu His Cys Ser Gly
                -15                 -10                 -5

Ser Phe Ser Gln Leu Val Leu Thr Gln Ser Pro Ser Ala Ser Ala Ser
         -1   1               5                  10

Leu Gly Ala Ser Val Lys Leu Thr Cys Thr Leu Ser Ser Gln His Ser
        15                  20                  25

Thr Tyr Thr Ile Glu Trp Tyr Gln Gln Pro Glu Lys Gly Pro Arg
 30                  35                  40                  45

Tyr Leu Met Asp Leu Lys Gln Asp Gly Ser His Ser Thr Gly Asp Gly
            50                  55                  60

Ile Pro Asp Arg Phe Ser Gly Ser Ser Ser Gly Ala Glu Arg Tyr Leu
                65                  70                  75

Thr Ile Ser Ser Leu Gln Ser Glu Asp Glu Ala Asp Tyr Ile Cys Gly
            80                  85                  90

Val Gly Asp Thr Ile Lys Glu Gln Phe Val Tyr Val Phe Gly Gly Gly
        95                  100                 105

Thr Lys Leu Thr Val Leu Gly Gln Pro
110                 115

<210> SEQ ID NO 86
<211> LENGTH: 137
<212> TYPE: PRT
<213> ORGANISM: Homo sapiens

<400> SEQUENCE: 86

Met Ala Trp Thr Pro Leu Phe Phe Phe Val Leu His Cys Ser Gly
                -15                 -10                 -5

Ser Phe Ser Gln Leu Val Leu Thr Gln Ser Pro Ser Ala Ser Ala Ser
         -1   1               5                  10

Leu Gly Ala Ser Val Lys Leu Thr Cys Thr Leu Ser Ser Gln His Ser
        15                  20                  25

Thr Tyr Thr Ile Glu Trp Tyr Gln Gln Pro Glu Lys Gly Pro Lys
 30                  35                  40                  45

Tyr Val Met Asp Leu Lys Gln Asp Gly Ser His Ser Thr Gly Asp Gly
            50                  55                  60

Ile Pro Asp Arg Phe Ser Gly Ser Ser Ser Gly Ala Glu Arg Tyr Leu
                65                  70                  75

Thr Ile Ser Ser Leu Gln Ser Glu Asp Glu Ala Asp Tyr Ile Cys Gly
            80                  85                  90

Val Gly Asp Thr Ile Lys Glu Gln Phe Val Tyr Val Phe Gly Gly Gly
        95                  100                 105

Thr Lys Leu Thr Val Leu Gly Gln Pro
```

-continued

```
110             115

<210> SEQ ID NO 87
<211> LENGTH: 137
<212> TYPE: PRT
<213> ORGANISM: Homo sapiens

<400> SEQUENCE: 87

Met Ala Trp Thr Pro Leu Phe Phe Phe Val Leu His Cys Ser Gly
             -15                 -10                  -5

Ser Phe Ser Gln Leu Val Leu Thr Gln Ser Pro Ser Ala Ser Ala Ser
         -1    1               5                  10

Leu Gly Ala Ser Val Lys Leu Thr Cys Thr Leu Ser Ser Gln His Ser
         15                  20                  25

Thr Tyr Thr Ile Glu Trp Tyr Gln Gln Pro Glu Lys Gly Pro Arg
 30                  35                  40                  45

Tyr Val Met Asp Leu Lys Gln Asp Gly Ser His Ser Thr Gly Asp Gly
                 50                  55                  60

Ile Pro Asp Arg Phe Ser Gly Ser Ser Ser Gly Ala Glu Arg Tyr Leu
                 65                  70                  75

Thr Ile Ser Ser Leu Gln Ser Glu Asp Glu Ala Asp Tyr Ile Cys Gly
             80                  85                  90

Val Gly Asp Thr Ile Lys Glu Gln Phe Val Tyr Val Phe Gly Gly Gly
         95                  100                 105

Thr Lys Leu Thr Val Leu Gly Gln Pro
110             115

<210> SEQ ID NO 88
<211> LENGTH: 118
<212> TYPE: PRT
<213> ORGANISM: Murine sp.

<400> SEQUENCE: 88

Glu Val Gln Leu Val Glu Ser Gly Gly Asp Leu Val Lys Pro Gly Gly
 1               5                  10                  15

Ser Leu Lys Leu Ser Cys Ala Ala Ser Gly Phe Thr Phe Ser Ser Tyr
                 20                  25                  30

Gly Met Ser Trp Ile Arg Gln Thr Pro Asp Lys Arg Leu Glu Trp Val
             35                  40                  45

Ala Thr Ile Ser Ser Gly Gly Ser Tyr Thr Tyr Tyr Pro Asp Ser Val
         50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Phe Tyr Cys
                 85                  90                  95

Ala Arg Gln Thr Thr Met Thr Tyr Phe Ala Tyr Trp Gly Gln Gly Thr
             100                 105                 110

Leu Val Thr Val Ser Ala
         115

<210> SEQ ID NO 89
<211> LENGTH: 115
<212> TYPE: PRT
<213> ORGANISM: Homo sapiens

<400> SEQUENCE: 89

Gln Val Gln Leu Val Glu Ser Gly Gly Gly Val Val Gln Pro Gly Arg
 1               5                  10                  15
```

```
Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ser Arg Gly Asp Tyr Trp Gly Gln Gly Thr Leu Val Thr
            100                 105                 110

Val Ser Ser
        115

<210> SEQ ID NO 90
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 90

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met Ser Trp Val Arg Gln Ala Pro Gly Lys Gly Leu Glu Trp Val
         35                  40                  45

Ala Thr Ile Ser Ser Gly Gly Ser Tyr Thr Tyr Tyr Pro Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gln Thr Thr Met Thr Tyr Phe Ala Tyr Trp Gly Gln Gly Thr
            100                 105                 110

Leu Val Thr Val Ser Ser
        115

<210> SEQ ID NO 91
<211> LENGTH: 118
<212> TYPE: PRT
<213> ORGANISM: Murine sp.

<400> SEQUENCE: 91

Gln Leu Val Leu Thr Gln Ser Ser Ser Ala Ser Phe Ser Leu Gly Ala
 1               5                  10                  15

Ser Ala Lys Leu Thr Cys Thr Leu Ser Ser Gln His Ser Thr Tyr Thr
             20                  25                  30

Ile Glu Trp Tyr Gln Gln Gln Pro Leu Lys Pro Pro Lys Tyr Val Met
         35                  40                  45

Asp Leu Lys Gln Asp Gly Ser His Ser Thr Gly Asp Gly Ile Pro Asp
     50                  55                  60

Arg Phe Ser Gly Ser Ser Ser Gly Ala Asp Arg Tyr Leu Ser Ile Ser
 65                  70                  75                  80
```

```
Asn Ile Gln Pro Glu Asp Glu Ala Met Tyr Ile Cys Gly Val Gly Asp
                85                  90                  95

Thr Ile Lys Glu Gln Phe Val Tyr Val Phe Gly Gly Gly Thr Lys Val
            100                 105                 110

Thr Val Leu Gly Gln Pro
        115

<210> SEQ ID NO 92
<211> LENGTH: 99
<212> TYPE: PRT
<213> ORGANISM: Homo sapiens

<400> SEQUENCE: 92

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gly His Ser Ser Tyr Ala
             20                  25                  30

Ile Ala Trp His Gln Gln Pro Glu Lys Gly Pro Arg Tyr Leu Met
         35                  40                  45

Lys Leu Asn Ser Asp Gly Ser His Ser Lys Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gln Thr Trp Gly
                 85                  90                  95

Thr Gly Ile

<210> SEQ ID NO 93
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 93

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr
             20                  25                  30

Ile Glu Trp His Gln Gln Pro Glu Lys Gly Pro Arg Tyr Leu Met
         35                  40                  45

Lys Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 94
<211> LENGTH: 118
<212> TYPE: PRT
<213> ORGANISM: Artificial Sequence
<220> FEATURE:
```

-continued

<223> OTHER INFORMATION: Description of Artificial Sequence: synthetic
      peptide

<400> SEQUENCE: 94

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr
             20                  25                  30

Ile Glu Trp His Gln Gln Pro Glu Lys Gly Pro Arg Tyr Leu Met
         35                  40                  45

Lys Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Thr Ile Lys Glu Gln Phe Val Tyr Val Phe Gly Gly Gly Thr Lys Leu
            100                 105                 110

Thr Val Leu Gly Gln Pro
            115

<210> SEQ ID NO 95
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 95

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr
             20                  25                  30

Ile Glu Trp His Gln Gln Pro Glu Lys Pro Pro Arg Tyr Leu Met
         35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Thr Ile Lys Glu Gln Phe Val Tyr Val Phe Gly Gly Gly Thr Lys Leu
            100                 105                 110

Thr Val Leu Gly Gln Pro
            115

<210> SEQ ID NO 96
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 96

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr

```
                        20                  25                  30

Ile Glu Trp His Gln Gln Pro Glu Lys Gly Pro Arg Tyr Leu Met
        35                  40                  45

Lys Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Pro Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
            115

<210> SEQ ID NO 97
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 97

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp His Gln Gln Pro Glu Lys Gly Pro Arg Tyr Leu Met
        35                  40                  45

Lys Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
            115

<210> SEQ ID NO 98
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 98

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp His Gln Gln Pro Glu Lys Pro Pro Arg Tyr Leu Met
        35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
```

-continued

```
                65                  70                  75                  80
Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
            115

<210> SEQ ID NO 99
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 99

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp His Gln Gln Pro Glu Lys Gly Pro Arg Tyr Leu Met
            35                  40                  45

Lys Leu Lys Gln Asp Gly Ser His Ser Thr Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Pro Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
            115

<210> SEQ ID NO 100
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 100

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Arg Tyr Leu Met
            35                  40                  45

Lys Leu Lys Gln Asp Gly Ser His Ser Thr Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
```

<210> SEQ ID NO 101
<211> LENGTH: 118
<212> TYPE: PRT
<213> ORGANISM: Artificial Sequence
<220> FEATURE:
<223> OTHER INFORMATION: Description of Artificial Sequence: synthetic peptide

<400> SEQUENCE: 101

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Arg Tyr Leu Met
            35                  40                  45

Lys Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
            115

<210> SEQ ID NO 102
<211> LENGTH: 118
<212> TYPE: PRT
<213> ORGANISM: Artificial Sequence
<220> FEATURE:
<223> OTHER INFORMATION: Description of Artificial Sequence: synthetic peptide

<400> SEQUENCE: 102

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Lys Tyr Leu Met
            35                  40                  45

Lys Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
            115

<210> SEQ ID NO 103
<211> LENGTH: 118
<212> TYPE: PRT
<213> ORGANISM: Artificial Sequence
<220> FEATURE:
<223> OTHER INFORMATION: Description of Artificial Sequence: synthetic -continued peptide

<400> SEQUENCE: 103

```
Gln Leu Val Leu Thr Gln Ser Pro Ser Ala Ser Ala Ser Leu Gly Ala
  1               5                  10                  15
Ser Val Lys Leu Thr Cys Thr Leu Ser Ser Gln His Ser Thr Tyr Thr
             20                  25                  30
Ile Glu Trp Tyr Gln Gln Pro Glu Lys Gly Pro Lys Tyr Leu Met
         35                  40                  45
Asp Leu Lys Gln Asp Gly Ser His Ser Thr Gly Asp Gly Ile Pro Asp
 50                  55                  60
Arg Phe Ser Gly Ser Ser Ser Gly Ala Glu Arg Tyr Leu Thr Ile Ser
 65                  70                  75                  80
Ser Leu Gln Ser Glu Asp Glu Ala Asp Tyr Tyr Cys Gly Val Gly Asp
                 85                  90                  95
Thr Ile Lys Glu Gln Phe Val Tyr Val Phe Gly Gly Gly Thr Lys Leu
            100                 105                 110
Thr Val Leu Gly Gln Pro
            115
```

<210> SEQ ID NO 104
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 104

```
Gln Leu Val Leu Thr Gln Ser Pro Ser Ala Ser Ala Ser Leu Gly Ala
  1               5                  10                  15
Ser Val Lys Leu Thr Cys Thr Leu Ser Ser Gln His Ser Thr Tyr Thr
             20                  25                  30
Ile Glu Trp Tyr Gln Gln Pro Glu Lys Gly Pro Lys Tyr Val Met
         35                  40                  45
Lys Leu Lys Gln Asp Gly Ser His Ser Thr Gly Asp Gly Ile Pro Asp
 50                  55                  60
Arg Phe Ser Gly Ser Ser Ser Gly Ala Glu Arg Tyr Leu Thr Ile Ser
 65                  70                  75                  80
Ser Leu Gln Ser Glu Asp Glu Ala Asp Tyr Tyr Cys Gly Val Gly Asp
                 85                  90                  95
Thr Ile Lys Glu Gln Phe Val Tyr Val Phe Gly Gly Gly Thr Lys Leu
            100                 105                 110
Thr Val Leu Gly Gln Pro
            115
```

<210> SEQ ID NO 105
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 105

```
Gln Leu Val Leu Thr Gln Ser Pro Ser Ala Ser Ala Ser Leu Gly Ala
  1               5                  10                  15
Ser Val Lys Leu Thr Cys Thr Leu Ser Ser Gln His Ser Thr Tyr Thr
             20                  25                  30
```

```
Ile Glu Trp Tyr Gln Gln Pro Glu Lys Gly Pro Lys Tyr Val Met
        35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 106
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 106

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
             20                  25                  30

Ile Glu Trp Tyr Gln Gln Pro Glu Lys Gly Pro Arg Tyr Leu Met
        35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 107
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 107

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
             20                  25                  30

Ile Glu Trp Tyr Gln Gln Pro Glu Lys Gly Pro Arg Tyr Val Met
        35                  40                  45

Lys Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80
```

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
            115

<210> SEQ ID NO 108
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 108

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Arg Tyr Val Met
            35                  40                  45

Asp Leu Lys Gln Asp Gly Ser His Ser Thr Gly Asp Gly Ile Pro Asp
50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
            115

<210> SEQ ID NO 109
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 109

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Lys Tyr Leu Met
            35                  40                  45

Lys Leu Lys Gln Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
            115

-continued

```
<210> SEQ ID NO 110
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 110

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Lys Tyr Leu Met
         35                  40                  45

Asp Leu Lys Gln Asp Gly Ser His Ser Thr Gly Asp Gly Ile Pro Asp
     50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Ile Cys Gly Val Gly Asp
                 85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 111
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 111

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Arg Tyr Leu Met
         35                  40                  45

Asp Leu Lys Gln Asp Gly Ser His Ser Thr Gly Asp Gly Ile Pro Asp
     50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Ile Cys Gly Val Gly Asp
                 85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 112
<211> LENGTH: 118
<212> TYPE: PRT
<213> ORGANISM: Artificial Sequence
<220> FEATURE:
<223> OTHER INFORMATION: Description of Artificial Sequence: synthetic
      peptide
```

<400> SEQUENCE: 112

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Lys Tyr Val Met
        35                  40                  45

Asp Leu Lys Gln Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 113
<211> LENGTH: 118
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 113

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Arg Tyr Val Met
        35                  40                  45

Asp Leu Lys Gln Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

ANTIBODY AGAINST HUMAN PARATHORMONE RELATED PEPTIDES

TECHNICAL FIELD

The present invention relates to a human/mouse chimeric antibody comprising a variable region (V region) of a mouse monoclonal antibody against a parathyroid hormone related protein and a constant region (C region) of a human antibody, a humanized antibody in which complementarity determining regions of the light chain (L chain) and heavy chain (H chain) V regions of a mouse monoclonal antibody against a parathyroid hormone related protein (PTHrP) are grafted to a human antibody, the L and H chains of said antibody, as well as a polypeptide comprising the V region constituting the L or H chain of said antibody.

The present invention also relates to a DNA comprising a base sequence coding for the above mentioned antibody, particularly its V region, and a DNA coding for an L or H chain comprising the V region. Further, the present invention relates to a recombinant vector comprising said DNA and a host transformed with said vector.

Furthermore, the present invention relates to processes for preparing the chimeric and humanized antibodies against a PTHrP. Still further, the present invention relates to a pharmaceutical composition, and hypercalcemia-suppressing or hypophosphatemia-improving agent comprising the antibody against a PTHrP as an effective ingredient.

BACKGROUND OF THE INVENTION

Hypercalcemia associated with malignant tumor is a serious complicated symptom found in 5 to 20% of the whole patients suffering from malignant tumor and is considered to be a terminal symptom of malignant tumor since it certainly leads to death if it is left as it is. Control of hypercalcemia may greatly affect the prognosis and QOL (quality of life) of a patient; therefore, it will clinically play a significant role.

Generally, hypercalcemia in patients suffering from malignant tumor is roughly classified between HHM (humoral hypercalcemia of malignancy) based on tumor-producing humoral bone resorption factors and LOH (local osteolytic hypercalcemia) based on local action of tumor transferred or infiltrated to the bone. In HHM, it is believed that bone resorption or osteoclasis is promoted to increase the flow of calcium and produces hypercalcemia in cooperation with the reduced renal calcium-excreting ability (S. Wada and N. Nagata, Internal Medicine, 69, 644–648).

Hypercalcemia is considered to exhibit its symptoms when the concentration of calcium in the serum exceeds 12 mg/dl; as its symptoms, anorexia (inappetence), nausea and emesis (vomiting) are non-specifically observed at the early stage in patients suffering from malignant tumor. When hypercalcemia is worsened, the reduction of water-concentrating ability due to lesion of the renal distal tubules leads to hyperuresis (polyuria) and anorexia and nausea will be accompanied with dehydration due to insufficient uptake of water.

As humoral factors causing HHM among the hypercalcemia associated with malignant tumor, Moseley, J. M. et al. found parathyroid hormone related protein (hereinafter referred to as "PTHrP") which are substances like parathyroid hormone (PTH): Proc. Natl. Acad. Sci. USA (1987) 84, 5048–5052.

Thereafter, a gene coding for PTHrP was isolated (Suva, L. J. et al., Science (1987) 237, 893) and it was elucidated from its analysis that there are three kinds of human PTHrPs having 139, 141 and 173 amino acids due to alternative splicing of the gene and that various fragments are present in the blood due to restricted degradation of PTHrP (1–139) having the whole structure: Baba, H., Clinical Calcium (1995) 5, 229–223. In PTHrP, 8 amino acids of the N-terminal 13 amino acids are identical with those in PTH and it is deduced that the amino acid site at position 14 to position 34 has a steric structure similar to PTH as well; thus, PTHrP and PTH bind to a common PTH/PTHrP receptor at least in the N-terminal region: Jueppner, H. et al., Science (1991) 254, 1024–1026; Abou-Samra, A-B. et al., Proc. Natl. Acad. Sci. USA (1992) 89, 2732–2736.

PTHrP is reported to be produced in a variety of tumoral tissues and it has been elucidated that not only in tumors, PTHrP is also produced in various normal tissues of from fetuses to adults, including skin, central nervous system, uterus, placenta, lactating mammary gland, thyroid gland, parathyroid gland, adrenal gland, liver, kidney and urinary bladder: Burtis, W. J., Clin. Chem. (1992) 38, 2171–2183; Stewart, A. F. & Broadus, A. E., J. Clin. Endocrinol. (1991) 71, 1410–1414. Further, PTHrP is considered to play an important role in the metabolic regulation of calcium which is maintained at a higher level in the fetal to newborn period than in the mother.

PTH/PTHrP receptors are known to be present mainly in the bone and kidney (C. Shigeno, Clinical Calcium (1995) 5, 355–359) and to activate plural intracellular signal transmission systems by binding of PTHrP to the receptors. One of them is adenylate cyclase and the other is phospholipase C. Activation of adenylate cyclase increases the concentration of intracellular cAMP to activate protein kinase A. Phospholipase C decomposes phosphatidylinositol 4,5-bisphosphonate to produce inositol 1,4,5-triphosphonate and diacylglycerol. G-protein is involved in these signal transmission systems: Coleman, D. T. et al., Biochemical mechanisms of parathyroid hormone action. In: "The parathyroids" (Bilezikian, J. P. et al.), Raven Press, New York (1994) page 239.

Through these signal transmission systems, PTHrP causes hypercalcemia, hypophosphatemia, decrease of renal phosphate-resorbing ability, increase of renal cAMP-excretion and the like which are observed in HHM.

Thus, it has been elucidated that PTHrP is closely related to hypercalcemia associated with malignant tumor. In the treatment of hypercalcemia associated with malignant tumor, calcitonin, steroid agents, indomethacin, inorganic phosphate salts, bisphosphonates and the like are used, as well as fluid replacement. However, these agents may show reduction of their effects upon consecutive use, some serious side-effects, or slow expression of their pharmacological effects; accordingly, use of agents or drugs which have higher therapeutic effects and less side-effects is highly expected.

On the other hand, as a new attempt to treat hypercalcemia associated with malignant tumor, Kukreja, S. C. et al. reported that when a neutralizing antiserum against PTHrP was administered to athymic mice in which human lung or larynx cancer cells had been transplanted to generate hypercalcemia, the blood calcium concentration and urinary cAMP level were reduced: J. Clin. Invest. (1988) 82, 1798–1802. Kanji Sato et al. reported that when an antibody against PTHrP (1–34) was administered to nude mice to which a PTHrP-producing human tumor was transplanted, the hypercalcemia was reduced and the viable time period of the mice was greatly prolonged: J. bone & Mine. Res. (1993) 8, 849–860. Further, Japanese Patent Application Laid Open Publication No. 4-228089 discloses mouse/human chimeric antibodies against human PTHrP (1–34).

Mouse monoclonal antibodies are highly immunogenic (sometimes also referred to as "antigenic") in humans, which limits the medical therapeutic values of the mouse monoclonal antibodies in humans. For instance, a mouse antibody may be metabolized as a foreign matter when administered to a human; therefore, the half-life of the mouse antibody is relatively short in humans and its expected effects are not sufficiently exhibited. Further, human anti-mouse antibodies. (HAMA) raised against the administered mouse antibody may cause immune responses which are inconvenient and dangerous to patients, such as serum diseases and other allergic reactions. Accordingly, mouse monoclonal antibodies can not frequently be administered to humans.

In order to solve these problems, methods for reducing the immunogenicity of non-human derived antibodies, for example, mouse-derived monoclonal antibodies have been developed. One of these methods is to make a chimeric antibody in which the variable-region (V region) is derived from a mouse monoclonal antibody and the constant region (C region) is derived from an appropriate human antibody.

Since the resulting chimeric antibody has the intact variable region of the original mouse antibody, it can be expected that the chimeric antibody may bind to an antigen with the same specificity as the original mouse antibody. Further, such a chimeric antibody has a substantially reduced proportion of an amino acid sequence derived from a non-human animal; therefore, it is anticipated to have a lower immunogenicity as compared with the original mouse antibody. Although the chimeric antibody binds to its antigen equivalently with the original mouse monoclonal antibody while showing a lower immunogenicity, some immune responses to the mouse variable region may still be possibly generated: LoBuglio, A. F. et al., Proc. Natl. Acad. Sci. USA, 86, 4220–4224, 1989.

A second method for reducing the immunogenicity of mouse antibodies is still more complicated but expected to further greatly reduce the potential immunogenicity of the mouse antibodies. In this method, only the complementarity determining regions (CDRs) of the variable region of a mouse antibody are grafted to a human variable region to create a "reshaped" human variable region. If required, a partial amino acid sequence of a framework region (FR) supporting the CDRs in a variable region of a mouse antibody may be grafted to a human variable region in order to make the structure of CDRs in the reshaped human variable region closer to that of the original mouse antibody.

Then, these humanized, reshaped human variable regions are combined with human constant regions. In the finally reshaped, humanized antibody, the portions derived from non-human amino acid sequences are only CDRs and a very small part of FR. The CDRs are composed of a hypervariable amino acid sequence and these do not show any species-specific sequences. Therefore, a humanized antibody comprising mouse CDRs will no longer have any stronger immunogenicity than a naturally occurring human antibody containing human CDRs.

With respect to humanized antibodies, further reference should be made to Riechmann, L. et al., Nature, 332, 323–327, 1988; Verhoeye, M. et al., Science, 239, 1534–1536, 1988; Kettleborough, C. A. et al., Protein Engng., 4, 773–783, 1991; Maeda, H. et al., Human Antibodies and Hybridoma, 2, 124–134, 1991; Gorman, S. D. et al., Proc. Natl. Acad. Sci. USA, 88, 4181–4185, 1991; Tempest, P. R. et al., Bio/Technology, 9, 266–271, 1991; Co, M. S. et al., Proc. Natl. Acad. Sci. USA, 88, 2869–2873, 1991; Carter, P. et al., Proc. Natl. Acad. Sci. USA, 89, 4285–4289, 1992; Co, M. S. et al., J. Immunol., 148, 1149–1154 1992; and Sato, K. et al., Cancer Res., 53, 851–856, 1993.

Although humanized antibodies are expected to be useful for therapeutic purposes as previously mentioned, no humanized antibody against PTHrP has been known nor suggested in the aforementioned references. Further, there is no standardized means generally applicable to any antibodies in the process for preparing humanized antibodies; various means and methods are necessary to make a humanized antibody exhibiting a sufficient binding, neutralizing activity to a specific antigen: see, for example, Sato, K. et al., Cancer Res., 53, 851–856, 1993.

DISCLOSURE OF THE INVENTION

It is an object of the present invention to provide a human/mouse chimeric antibody comprising a variable region (V region) of a mouse monoclonal antibody against PTHrP and a constant region (C region) of a human antibody, a humanized antibody in which complementarity determining regions of V regions of the light chain (L chain) and heavy chain (H chain) of a mouse monoclonal antibody against PTHrP are grafted to a human antibody, the L and H chains of said antibody, as well as a polypeptide comprising the V region constituting the L or H chain of said antibody.

It is another object of the present invention to provide a DNA comprising a base sequence coding for the above mentioned antibody, particularly its V region, and a DNA coding for an L or H chain comprising a polypeptide comprising the V region. Still another object of the present invention is to provide a recombinant vector comprising said DNA and a host transformed with said vector. Further, an object of the present invention is to provide processes for preparing the chimeric and humanized antibodies against PTHrP. It is a still another object of the present invention to provide an antibody against PTHrP having a high neutralizing activity. A still further object of the present invention is to provide a pharmaceutical composition, and hypercalcemia-suppressing, hypophosphatemia-improving or alkalosis-improving agent comprising the antibody or humanized antibody against PTHrP as an effective ingredient.

As a result of the energetic study with a view to the above mentioned objects, the present inventors have successfully obtained an antibody in which the immunogenicity of mouse monoclonal antibodies against PTHrP is reduced in humans; thus, the present invention has been accomplished.

The present invention is directed to a chimeric L chain comprising an L chain C region of a human antibody and an L chain V region of a mouse monoclonal antibody against PTHrP. The L chain V region includes one comprising an amino acid sequence as shown in SEQ ID NO:45 and the L chain C region includes a Cλ region.

The present invention is also directed to a chimeric H chain comprising an H chain C region of a human antibody and an H chain V region of a mouse monoclonal antibody against PTHrP. The H chain V region includes one comprising an amino acid sequence as shown in SEQ ID NO:46 and the C region includes a Cλ region.

Further, the present invention is directed to a chimeric monoclonal antibody against PTHrP comprising said chimeric L chain and said chimeric H chain.

Still further, the present invention includes a polypeptide comprising an L chain V region of a humanized antibody comprising framework regions 1 to 4 of an L chain V region of a human antibody and complementarity determining regions 1 to 3 of an L chain V region of a mouse monoclonal antibody against PTHrP. The complementarity determining regions 1 to 3 include those comprising amino acid sequences as shown in SEQ ID NOs: 59–61, respectively; the framework regions 1 to 3 include those derived from the framework regions 1 to 3 of human antibody HSU03868, respectively, and the framework region 4 includes one derived from the framework region 4 of human antibody S25755; or the framework regions 1 to 3 include those substantially identical with the framework regions 1 to 3 of human antibody HSU03868, respectively, and the framework region 4 includes one substantially identical with the framework region 4 of human antibody S25755.

The term "substantially identical" as used herein means that the framework regions of the human antibody used in a humanized antibody may have a deletion, replacement and/or addition of amino acid(s) required to form the complementarity determining regions of a mouse monoclonal antibody such that the humanized antibody should have an activity equivalent to that of the mouse monoclonal antibody.

Thus, the present invention is concerned with a polypeptide comprising an L chain V region of a humanized antibody wherein in the framework regions the 36th and 49th amino acids in accordance with Kabat's prescription (Kabat, E. A. et al., US Dept. Health and Human Services, US Government Printing Offices, 1991) are tyrosine and aspartic acid, respectively.

The present invention is also directed to a polypeptide comprising an L chain V region of a humanized antibody comprising an amino acid sequence as shown in any of SEQ ID NOs:48–51.

Further, the present invention is directed to a polypeptide comprising an L chain V region of a humanized antibody wherein the 45th and 87th amino acids in accordance with Kabat's prescription in the framework regions are lysine and isoleucine, respectively.

Still further, the present invention is directed to a polypeptide comprising an L chain V region of a humanized antibody comprising an amino acid sequence as shown in any of SEQ ID NOs: 52–55.

The present invention is further concerned with a polypeptide comprising an H chain V region of a humanized antibody comprising framework regions 1 to 4 of an H chain V region of a human antibody and complementarity determining regions 1 to 3 of an H chain V region of a mouse monoclonal antibody against a human PTHrP. The complementarity determining regions 1 to 3 include those comprising amino acid sequences as shown in SEQ ID NOs:62–64, respectively, the framework regions 1 to 4 include those derived from framework regions 1 to 4 of a human antibody belonging to human subgroup III (Human Subgroup III (HSG III), Kabat, E. A. et al., US Dept. Health and Human Services, US Government Printing Offices, 1991), more particularly those derived from the framework regions 1 to 4 of human antibody S31679, respectively, or those substantially identical with the framework regions 1 to 4 of human antibody S31679, respectively.

Also, the present invention is concerned with a polypeptide comprising an H chain V region of a humanized antibody comprising the amino acid sequence as shown in SEQ ID NO:56.

The present invention is also concerned with an L chain of a humanized antibody against a human PTHrP comprising a polypeptide comprising an L chain V region of said humanized antibody and a polypeptide comprising an L chain C region of a human antibody. The C region includes a Cλ region, the framework regions 1 to 3 include those substantially identical with the framework regions 1 to 3 of human antibody HSU03868, respectively, the framework region 4 includes one substantially identical with the framework region 4 of human antibody S25755, and the amino acid sequences of the complementarity determining regions 1 to 3 include those represented by SEQ ID NOs:59–61, respectively.

Further, the present invention is also concerned with an H chain of a humanized antibody against a human PTHrP comprising polypeptides comprising an H chain C region and H chain V region of said human antibody. The C region includes a Cy1 region, the framework regions 1 to 4 include those derived from the framework regions 1 to 4 derived from a human antibody belonging to HSGIII, and the complementarity determining regions 1 to 3 include those comprising the amino acid sequences as shown in SEQ ID NOs:62–64, respectively.

Still further, the present invention is also concerned with an anti-PTHrP antibody with a weak antigenicity and a high neutralizing activity. The PTHrP antibody includes a human antibody, a humanized antibody, a chimeric antibody and a primatized antibody, which may be utilized in the treatment of human diseases. The antibody has a low dissociation constant. Further, the antibody of the present invention has a high neutralizing activity due to its low dissociation constant and, therefore, can be utilized for the treatment of human diseases.

The antibody of the present invention has a dissociation constant of $1.86 \times 10^{-7}$ [M] or less, a dissociation rate constant of $1.22 \times 10^{-1}$ [1/Sec] or less, and an association rate constant of $6.55 \times 10^{4}$ [1/M.Sec] or more. These constants may be measured by Scatchard analysis using RI labeled ligands or Surface plasmon resonance sensor.

The present invention is further directed to a DNA comprising a base sequence coding for an L chain V region or H chain V region of a mouse monoclonal antibody against a human PTHrP. The L chain V region and H chain V region include those comprising the amino acid sequence as shown in SEQ ID NOs:45–46, respectively, the DNA comprising a base sequence coding for the L chain V region includes, for example, one represented by SEQ ID NO: 65, and the DNA comprising a base sequence coding for the H chain V region includes one represented by SEQ ID NO:57.

Further, the present invention is also directed to a DNA coding for said chimeric L or H chain. The DNA coding for said L chain includes, for example, one comprising the base sequence as shown in SEQ ID NO:65 and the DNA coding for said H chain includes one comprising the base sequence as shown in SEQ ID NO:57.

Still further, the present invention is also directed to a DNA comprising a base sequence coding for an L chain V region or H chain V region of said humanized antibody. The DNA comprising a base sequence coding for the L chain V region includes one comprising the base sequence as shown in any of SEQ ID NOs:66–74 and the DNA comprising a base sequence coding for the H chain V region includes one represented by SEQ ID NO:58.

The present invention also relates to a DNA for an L chain V region of a humanized antibody comprising a base sequence coding for the amino acid sequence as shown in any of SEQ ID NOs:47–55. Said DNA includes one comprising the base sequence as shown in any of SEQ ID NOs:66–74.

Still further, the present invention relates to a DNA for an H chain V region of a humanized antibody coding for the amino acid sequence as shown in SEQ ID NO:56. Said DNA includes one comprising the base sequence as shown in SEQ ID NO:58.

The present invention further relates to a recombinant vector comprising any of said DNAs.

The present invention still further relates to a transformant transformed with said recombinant vector.

Also, the present invention relates to a process for preparing a chimeric or humanized antibody against a human parathyroid hormone related protein comprising cultivating said transformant and collecting a chimeric or humanized antibody against a human parathyroid hormone related protein from the resulting culture.

Still further, the present invention also relates to a pharmaceutical composition, or hypercalcemia-suppressing or hypophosphatemia-improving agent comprising said antibody as an effective ingredient. The calcemia is caused by malignant tumor and the hypophosphatemia is often observed in patients suffering from hypercalcemia associated with malignant tumor. Thus, the antibody of the present invention can be used in the treatment of the malignant tumor or in the improvement of hypercalcemia or hypophosphatemia symptoms. The malignant tumor may include, but not limited to, at least one selected from the group consisting of pancreas, lung, pharynx, larynx, tongue, gingiva, esophagus, stomach, biliary duct, breast, kidney, urinary bladder, uterus and prostate cancers, and malignant lymphoma. The hypercalcemia-suppressing agent of the present invention can be applicable to any malignant tumor which may cause hypercalcemia.

The present invention will be described in detail hereinbelow.

1. Production of Mouse Monoclonal Antibodies Against Human PTHrP

Mouse monoclonal antibodies against PTHrP may be prepared by preparing hybridomas through cell fusion between myeloma cells and antibody-producing cells derived from animals immunized with the antigen and selecting clones producing antibodies specifically inhibiting the PTHrP activity from the resulting hybridomas.

(1) Preparation of Antigens

PTHrP used for the immunization of animals includes peptides having the whole or part of the amino acid sequence of PTHrP prepared by recombinant DNA technology or chemical synthesis, and PTHrP derived from supernatants of cancer cells causing hypercalcemia. For example, a peptide [PTHrP(1–34)] comprising the 1st to 34th amino acids of the known PTHrP (Kemp, B. E. et al., Science (1987) 238, 1568–1570) may be used as the antigen. The human PTHrP (1–34) has an amino acid sequence as shown in SEQ ID NO:75.

The resultant PTHrP is attached to a carrier protein such as thyroglobulin followed by addition of an adjuvant. Any adjuvant may be mixed, including Freund's complete and incomplete adjuvants.

(2) Immunization and Collection of Antibody Producing Cells

The above resultant antigen is administered to a mammal, such as mouse, rat, horse, monkey, rabbit, goat or sheep. Immunization may be carried out by any known methods, including intravenous, subcutaneous and intraperitoneal injections. Intervals of injections for immunization are not particularly limited and may be a few days to a few weeks, preferably 4 to 21 days.

Two or three days after final immunization, antibody producing cells are collected. The antibody producing cells include spleen, lymph node and peripheral blood cells; generally, spleen cells are utilized. The single dose amount of antigen used for immunization is 100 µg per mouse.

(3) Determination of Antibody Titers

In order to determine the immune response levels of immunized animals and select hybrodomas of interest from the cells subjected to cell fusion treatment, the antibody titer in the blood of the immunized animal or the antibody titer in the supernatant of the antibody producing cells is measured.

Methods for detecting the antibodies are known, including EIA (enzyme immunoassay), RIA (radio immunoassay), and ELISA (enzyme linked immunosorbent assay).

(4) Cell Fusion

Myeloma cells used to be fused with antibody producing cells include cell lines which are derived from various animals such as mouse, rat and human, and generally available for those skilled in the art. Suitable cell lines used are those having a drug resistance, incapable of surviving in a selective medium such as HAT medium in the unfused state, and capable of surviving therein only in the fused state. Generally used are 8-azaguanine resistant cell lines, which lack hypoxanthine-guanine-phosphoribosyltransferase and can not grow in a hypoxanthine-aminopterin-thymidine (HAT) medium.

Suitable myeloma cells to be used include various known cell lines, such as P3 (P3×63Ag8.653) (J. Immunol. (1979) 123:1548–1550); P3×63Ag8U.1 (Current Topics in Microbiology and Immunology (1978) 81:1–7); NS-1 (Kohler, G and Milstein, C., Eur. J. Immunol. (1976) 6:511–519); MPC-11 (Margulies, D. H. et al., Cell (1976) 8:405–415); SP2/0 (Shulman, M. et al., Nature (1978) 276:269–270); FO (de St. Groth, S. F. et al., J. Immunol. Methods (1980) 35:1–21); S194 (Trowbridge, I. S., J. Exp. Med. (1978) 148:313–323); and R210 (Galfre, G. et al., Nature (1979) 277:131–133).

Antibody producing cells may be obtained from spleen cells, lymph node cells, or the like. That is, the spleen, lymph node or the like is extracted or removed from any of the aforementioned animals and the tissue is crushed. The resulting crushed materials are suspended in a medium or buffer, such as PBS, DMEM or RPMI1640, filtered through stainless mesh or the like and centrifuged to prepare the desired antibody producing c ells.

Then, said myeloma cells and antibody producing cells are subjected to cell fusion.

Cell fusion may be carried out by bringing the myeloma and antibody-producing cells into contact with each other at a ratio of 1:1 to 1:10 in a medium for the culture of animal cells, such as MEM, DMEM or RPME-1640, in the presence of a fusion accelerator at 30 to 37° C. for 1 to 15 minutes. To accelerate the cell fusion, any fusion accelerator or virus can be used, such as polyethylene glycol with an average molecular weight of 1,000 to 6,000, polyvinyl alcohol or Sendai virus. The fusion of the antibody producing and myeloma cells may also be performed in a commercially available cell fusion apparatus utilizing an electric stimulation such as electroporation.

(5) Selection and Cloning of Hybridomas

Hybridomas of interest are selected from the cells after the cell fusion, for example, by a method utilizing selective growth of cells in selective media.

That is, a cell suspension is diluted with a suitable medium and inoculated on a microtiter plate. A selective medium such as HAT medium is added to each well and incubated while properly replacing the selective medium with a fresh one.

Thus, the growing cells a re collected as hybridomas.

These hybridomas are then screened by the limiting dilution, fluorescence-activated cell sorter or other method. Finally, hybridomas producing a monoclonal antibody are obtained.

(6) Collection of Monoclonal Antibodies

Methods for collecting monoclonal antibodies from the obtained hybridomas include conventional cell culture and ascites formation methods.

In the cell culture method, the hybridomas are cultivated in a medium for the culture of animal cells, such as RPMI-1640 medium containing 10 to 20% fetal bovine serum, MEM medium or serum-free medium, under conventional conditions (e.g., 37° C., 5% $CO_2$) for 2 to 14 days and the antibodies are collected from the supernatant.

In the formation of ascites, the hybridomas are inoculated intraperitoneally to the same species of mammal as the source of the myeloma cells so that the hybridomas grow abundantly. After 1 to 4 weeks, the ascites or sera are collected.

When the antibodies are necessary to be purified in these methods, known methods such as the ammonium sulfate precipitation, ion exchange chromatography and affinity chromatography may optionally be selected or combined.

2. Construction of Chimeric Antibodies (1) Cloning of DNA Comprising Base Sequence Coding for V Region of Mouse Monoclonal Antibody Against Human PTHrP (i) Preparation of mRNA To clone DNA comprising a base sequence coding for V region of mouse monoclonal antibody against human PTHrP, the collected hybridomas are treated in a conventional manner, for example, guanidine-ultracentrifugation (Chirgwin, J. M. et al., Biochemistry (1979) 18, 5294–5299), or AGPC method (Chomczynski, P et al., Analytical Biochemistry (1987) 162, 156–159), to prepare the total RNA, from which mRNA is prepared by e.g. Oligo(dT)-cellulose span column attached to mRNA Purification Kit (Pharmacia)-Quick Prep mRNA Purification Kit (Pharmacia AB) can also be used to prepare mRNA without need of extraction of the total RNA.

(ii) Preparation and Amplification of cDNA

From the mRNA obtained in (i) above, each cDNA in the V regions of L and H chains is synthesized with the use of a reverse transcriptase. In the synthesis of cDNA, Oligo-dT primer or an other appropriate primer which hybridizes to L or H chain C region, for example, MHC2 primer having the base sequence as shown in SEQ ID NO:1, may be used.

In the cDNA synthesis, said mRNA and primer are mixed and the reaction is effected in the presence of a reverse transcriptase at e.g. 52° C. for 30 minutes.

Amplification of cDNA of both L and H chains can be performed by PCR (polymerase chain reaction) based on 5'-RACE method (Frohman; M. A. et al., Proc. Natl. Acad. Sci. USA, 85, 8998–9002, 1988; Belyavsky, A. et al., Nucleic Acids Res., 17, 2919–2932, 1989) using 5'-Ampli FINDER RACE kit (CLONTECH Inc.). Thus, Ampli FINDER Anchor (SEQ ID NO:42) is linked to 5' end of the cDNA synthesized above and PCR is effected for DNAs comprising base sequences coding for L and H chain V regions. (Hereinafter, the DNA comprising a base sequence coding for L chain V region is sometimes referred to simply as "DNA for L chain V region" or "DNA coding for L chain V region". This also applies to H chain V region, C region etc. similarly.)

The primer for amplifying DNA for L chain V region which may be used includes, for example, Anchor primer (SEQ ID NO: 2) and primers designed from conserved sequences in Lλ chain constant region (Cλ region) of mouse antibodies such as MLC primer having the base sequence as shown in SEQ ID NO:4. The primer for amplifying DNA for H chain V region which may be used includes, for example, Anchor primer (SEQ ID NO:2) and MHC-GL primer (SEQ ID NO:3) (S. T. Jones, et al., Biotechnology, 9, 88, 1991).

(iii) Purification of DNA and Determination of Base Sequence

The PCR products are subjected to agarose gel electrophoresis according to conventional procedures to excise DNA fragments of interest, which are then recovered, purified and ligated to a vector DNA.

Purification of DNA may be carried out using commercially, available kits such as GENECLEAN II; BIO101. Vector DNA for carrying the DNA fragments which may be used herein is known, for example, pUC19 or Bluescript.

Said DNA and vector DNA are ligated using a known ligation kit (Takara Shuzo) to yield a recombinant vector. The resultant recombinant vector is introduced into e.g. *Escherichia coli* JM109 and ampicillin resistant colonies are selected; thus, a vector DNA is prepared in a known method: J. Sambrook, et al., "Molecular Cloning", Cold Spring Harbor Laboratory Press, 1989. After the vector DNA is digested with restriction enzyme(s), the base sequence of a desired DNA is determined by a known method such as dideoxy method: J. Sambrook, et al., "Molecular Cloning", Cold Spring Harbor Laboratory Press, 1989. In the present invention, an automated base sequence determining apparatus (DNA Sequencer 373A; ABI Inc.) may be used.

(iv) Complementarity Determining Region

H and L chain V regions form an antigen binding site and their whole structures have some similarity to each other. That is, four framework region (FR) portions are linked through three hypervariable regions, or complementarity determining region (CDR). The amino acid sequence in the FR is relatively well conserved while variability of the amino acid sequence in the CDR region is very high: Kabat, E. A. et al, "Sequence of Proteins of Immunological Interest" US Dept. Health and Human Services, 1983.

Many portions of the four FRs have β sheet structure and, as a result, three CDRs form a loop. The CDR may sometimes form a part of the β sheet structure. Therefore, three CDRs are sterically held at very near positions to each other by FRs, which form an antigen binding site together with the three CDRs in the paired regions.

In view of such facts, CDR regions can be found by comparison between the amino acid sequence in the variable region of a mouse monoclonal antibody against human PTHrP and the database of amino acid sequences for antibodies prepared by Kabat et al. ("Sequence of Proteins of Immunological Interest" US Dept. Health and Human Services, 1983) to investigate the homology therebetween.

(2) Construction of Expression Vector of Chimeric Antibody

Once DNA fragments coding for L and H chain V regions of mouse monoclonal antibody (hereinafter L or H chain of an antibody may sometimes be referred to as "mouse L chain" etc. for mouse antibodies and "human H chain" etc. for human antibodies) are cloned, the DNAs coding for mouse V regions and DNAs coding for human antibody constant regions are ligated and expressed to yield chimeric anti-human PTHrP antibodies.

A standard method for preparing chimeric antibodies involves ligating a mouse leader sequence and V region sequence present in a cloned cDNA to a sequence coding for a human antibody C region already present in an expression vector of a mammalian cell. Alternatively, a mouse leader sequence and v region sequence present in a cloned cDNA are ligated to a sequence coding for a human antibody C region followed by ligation to a mammalian cell expression vector.

The polypeptide comprising human antibody C region can be any of H or L chain C regions of human antibodies, including, for example, Cγ1, Cγ2, Cγ3 or Cγ4 for human H chains or Cλ or Cκ for L chains.

To prepare a chimeric antibody, two expression vectors are first constructed; that is, an expression vector containing DNAs coding for mouse L chain V region and human L chain C region under the control of an expression control region such as an enhancer/promoter system, and an expression vector containing DNAs coding for mouse H chain V region and human H chain C region under the control of an expression control region such as an enhancer/promoter system, are constructed. Then, host cells such as mammalian cells are cotransformed with these expression vectors and the transformed cells are cultivated in vitro or in vivo to produce a chimeric antibody: see, for example, WO91/16928.

Alternatively, the mouse leader sequence present in the cloned cDNA and DNAs coding for mouse L chain V region and human L chain C region as well as the mouse leader sequence and DNAs coding for mouse H chain V region and human H chain C region are introduced into a single expression vector (see, for example, WO94/11523) and said vector is used to transform a host cell; then, the transformed host is cultivated in vivo or in vitro to produce a desired chimeric antibody.

(i) Production of Chimeric Antibody H Chain

The vector for the expression of H chain of a chimeric antibody can be obtained by introducing cDNA comprising a base sequence coding for mouse H chain V region (hereinafter referred to also as "cDNA for H chain V region") into a suitable expression vector containing the genomic DNA comprising a base sequence coding for H chain C region of human antibody (hereinafter referred to also as "genomic DNA for H chain C region") or cDNA coding for said region (hereinafter referred to also as "cDNA for H chain C region"). The H chain C region includes, for example, Cγ1, Cγ2, Cγ3 or Cγ4 regions.

(i-a) Construction of Chimeric H Chain Expression Vector Containing Genomic DNA Coding for H Chain C Region The expression vectors having the genomic DNA coding for H chain C region, in particular, those coding for Cγ1 region, include, for example, HEF-PMh-g γ1 (WO92/19759) and DHFR-Δ E-RVh-PM1-f (WO92/19759).

When cDNA for mouse H chain V region is inserted into these expression vectors, an appropriate base sequence can be introduced into said cDNA through PCR method. For instance, PCR may be effected using a PCR primer which is designed such that said cDNA has a recognition sequence for a suitable restriction enzyme at its 5'-end and Kozak consensus sequence immediately before the initiation codon thereof so as to improve the transcription efficiency, as well as a PCR primer which is designed such that said cDNA has a recognition sequence for a suitable restriction enzyme at its 3'-end and a splice donor site for properly splicing the primary transcription products of the genomic DNA to give a mRNA, to introduce these appropriate base sequences into the expression vector.

After the thus constructed cDNA coding for mouse H chain V region is treated with a siutable restriction enzyme (s), it is inserted into said expression vector to construct a chimeric H chain expression vector containing the genome DNA coding for H chain C region (Cγ1 region).

(i-b) Construction of Chimeric H Chain Expression Vector Containing cDNA Comprising Base Sequence Coding for H Chain The expression vectors having the cDNA coding for H chain C region, such as Cγ1 region, may be constructed in the following manner: mRNA is prepared from CHO cells into which an expression vector DHFR-ΔE-RVh-PM1-f (see WO92/19759) comprising DNA coding for H chain V region of a humanized PM1 antibody and genomic DNA of H chain C region Cγ1 of a human antibody (N. Takahashi, et al., Cell, 29, 671–679 (1982)) and an expression vector RV1-PM1a (see WO92/19759) comprising genomic DNA coding for L chain V region of the humanized PM1 antibody and genomic DNA of Lκ chain C region of a human antibody have been introduced, and cDNA coding for the H chain V region of the humanized PM1 antibody and cDNA coding for the H chain C region (Cγ1) of the human antibody are cloned by RT-PCR method and ligated to an animal cell expression vector which has been treated with a suitable restriction enzyme(s), to construct a desired expression vector.

When cDNA coding for mouse H chain V region is directly ligated to cDNA coding for H chain C region Cγ1 of a human antibody, appropriate base sequences can be introduced into a fragment comprising cDNA coding for H chain V region through PCR method. For instance, PCR may be effected using a PCR primer which is designed such that said cDNA has a recognition sequence for a suitable restriction enzyme at its 5'-end and Kozak consensus sequence immediately before the initiation codon thereof so as to improve the transcription efficiency, as well as a PCR primer which is designed such that said cDNA has a recognition sequence for a suitable restriction enzyme at its 3'-end for directly ligating to the H chain C region Cγ1, to introduce these appropriate base sequences into said cDNA.

The thus constructed cDNA coding for mouse H chain V region is treated with a siutable restriction enzyme(s), ligated to cDNA coding for said H chain C region Cγ1, and inserted into an expression vector such as pCOS1 or pCHO1 to construct an expression vector containing the cDNA coding for a chimeric H chain.

(ii) Production of Chimeric Antibody L Chain

The vector for the expression of L chain of a chimeric antibody can be obtained by ligating a cDNA coding for mouse L chain V region and a genomic DNA or cDNA coding for L chain C region of a human antibody and introducing into a suitable expression vector. The L chain C region includes, for example, κ chain and λ chain.

(ii-a) Construction of Expression Vector Containing cDNA Coding for Chimeric Lλ chain When an expression vector containing cDNA coding for mouse L chain V region is constructed, appropriate base sequences can be introduced into said expression vector through PCR method. For instance, PCR may be effected using a PCR primer which is designed such that said cDNA has a recognition sequence for a suitable restriction enzyme at its 5'-end and Kozak consensus sequence for improving the transcription efficiency, as well as a PCR primer which is designed such that said cDNA has a recognition sequence for a suitable restriction enzyme at its 3'-end, to introduce these appropriate base sequences into said cDNA.

The whole base sequence of cDNA coding for human Lλ chain C region may be synthesized by a DNA synthesizer and constructed through PCR method. The human Lλ chain C region is known to have at least 4 different isotypes and each isotype can be used to construct an expression vector. For example, based on a search for the homology with Lλ chain C regions of cloned mouse monoclonal antibodies, an isotype Mcg+Ke+Oz– of the fragment of human Lλ chain C region (accession No. X57819) (P. Dariavach et al., Proc. Natl. Acad. Sci. USA, 84, 9074–9078, 1987) can be selected and used to construct an expression vector. To construct cDNA for the known human Lλ chain C region such as Mcg+Ke+Oz–, for example, the following four primers as shown in SEQ ID NOs:11–14 are designed: The primers MBC1HGP1 (SEQ ID NO:11) and MBC1HGP3 (SEQ ID NO:13) have sense DNA sequences and the primers MBC1HGP2 (SEQ ID NO:12) and MBC1HGP4 (SEQ ID NO:14) have antisense DNA sequences wherein each primer has a 20 to 23 bp complementary sequence at either end thereof.

MBC1HGPS (SEQ ID NO:15) and MBC1HGPR (SEQ ID NO: 16) are called external primers, have sequences homologous with MBC1HGP1 and MBC1HGP4, respectively, and have each a recognition sequence for a suitable restriction enzyme. Through PCR method, the four primers are assembled to synthesize full length cDNA and the external primers are added to amplify the cDNA.

The assembly through PCR method means that MBC1HGP1 and MBC1HGP2 or MBC1HGP3 and MBC1HGP4 are annealed through their complementary sequences to synthesize MBC1HGP1-MBC1HGP2 fragment and MBC1HGP3-MBC1HGP4 fragment and each fragment is again annealed through their complementary sequences to synthesize a cDNA coding for the full length human Lλ chain C region.

The thus constructed cDNA coding for human Lλ chain C region and the above constructed cDNA coding for mouse L chain V region can be ligated between suitable restriction enzyme sites and inserted into an expression vector such as pCOS1 or pCHO1 to construct an expression vector containing cDNA coding for a Lλ chain of a chimeric antibody.

(ii-b) Construction of Expression Vector Containing cDNA Coding for Chimeric Lκ Chain When an expression vector containing cDNA coding for mouse L chain V region is constructed, appropriate base sequences can be introduced into said cDNA through PCR method. For instance, PCR may be effected using a PCR primer which is designed such that said cDNA has a recognition sequence for a suitable restriction enzyme at its 5'-end and Kozak consensus sequence for improving the transcription efficiency, and a PCR primer which is designed such that said cDNA has a recognition sequence for a suitable restriction enzyme at its 3'-end, to introduce these appropriate base sequences into said cDNA.

The DNA coding for human Lκ chain C region to be ligated to the DNA coding for mouse L chain V region can be constructed from, for example, HEF-PM1k-gk containing the genomic DNA (see WO92/19759).

Recognition sequences for suitable restriction enzymes can be introduced, through PCR method, into 5'- and 3'-ends of DNA coding for Lκ chain C region, and the DNA coding for mouse L chain V region as constructed above and the DNA coding for Lκ chain C region can be ligated to each other and inserted into an expression vector such as pCOS1 or pCHO1 to construct an expression vector containing cDNA coding for Lκ chain of a chimeric antibody.

3. Production of Humanized Antibodies (1) Search for Homology With Human Antibodies In order to make a humanized antibody in which CDR of a mouse monoclonal antibody is grafted to a human antibody, it is desirable that there exists a high homology between FR of the mouse monoclonal antibody and FR of the human antibody. Accordingly, a comparison is made between V regions of H and L chains of mouse anti-human PTHrP monoclonal antibody and the V regions of all the known antibodies w whose structures have been elucidated with the use of Protein Data Bank. Further, they are simultaneously compared with the human antibody subgroups (HSG: Human subgroup) classified by Kabat et al. based on the length of antibody FR, the homology of amino acids, and the like: Kabat, E. A. et al, US Dep. Health and Human Services, US Government Printing Offices, 1991.

Human H chain V regions may be classified into HSG I to III according to the HSG classification by Kabat et al. and mouse anti-human PTHrP monoclonal antibody H chain V regions have a homology of 82.7% with the consensus sequence of HSG III. On the other hand, human Lλ chain V regions may be classified into HSG I to VI according to the HSG classification by Kabat et al. and mouse anti-human PTHrP monoclonal antibody Lλ chain V regions do not have a high homology with the consensus sequences of human Lλ chain V regions belonging to any subgroups.

When mouse anti-human PTHrP monoclonal antibody is to be humanized, therefore, it is desirable to use human H chain V region which belongs to HSG III and has the highest homology, or human H chain V region having a FR structure with a corresponding canonical structure (Chothia C, et al., J. Mol. Biol., 196, 901–917, 1987), as the human H chain V region, to construct a humanized antibody. Further, since there is no consensus sequence with a high homology in subgroups of human Lλ chain V regions, it is desirable to use human antibody Lλ chain V region with a highest homology registered in Protein Data Bank upon construction of a humanized antibody.

(2) Design of DNA Coding for Humanized Antibody V Region

The first step for designing DNA coding for a humanized antibody V region is to select a human antibody V region as a basis for the designing.

In the present invention, FR of a human antibody V region having a homology of higher than 80% with FR of a mouse antibody V region can be used in the humanized antibody. The FR of H chain V region as a fragment of a substantially identical FR may include FR derived from those belonging to the subgroup III, such as S31679: NBRF-PDB, Cuisinier A. M. et al., Eur. J. Immunol., 23, 110–118, 1993. Further, the FR of L chain V region as a fragment of a substantially identical FR may include, for example, FR1, FR2 and FR3 derived from human antibody HSU03868 (GEN-BANK, Deftos M. et al., Scand. J. Immunol., 39, 95–103, 1994) and FR4 derived from human antibody S25755 (NBRF-PDB).

The human antibody S31679 was cloned from cDNA library of human fetal livers while the human antibody HSU03868 was cloned as a novel gene for human Lλ chain V region.

(3) Preparation of Polypeptides Comprising Humanized Antibody V Region

In the humanized antibody of the present invention, the C region and the framework (FR) regions of the V region of said antibody are originated from human and the complementarity determining regions (CDR) of the V region are originated from mouse (FIG. 1). A polypeptide comprising the V region of the humanized antibody according to the present invention can be made in the manner called CDR-grafting by PCR method so long as a DNA fragment of a human antibody would be available as a template. The "CDR-grafting" refers to a method wherein a DNA fragment coding for a mouse-derived CDR is made and replaced for the CDR of a human antibody as a template.

If a DNA fragment of a human antibody to be used as a template is not available, a base sequence registered in a database may be synthesized in a DNA synthesizer and a DNA for a V region of a humanized antibody can be made by the PCR method. Further, when only an amino acid sequence is registered in the database, the whole base sequence may be deduced from the amino acid sequence on the basis of knowledge on the codon usage in antibodies as reported by Kabat, E. A. et al. in US Dep. Health and Human Services, US Government Printing Offices, 1991. This base sequence is synthesized in a DNA synthesizer and a DNA of a humanized antibody V region can be prepared by PCR method and introduced into a suitable host followed by expression thereof to produce the desired polypeptide.

Now, general procedures of CDR-grafting by PCR method are described below when a DNA fragment of a human antibody as a template is available.

(i) CDR-Grafting

Now suppose DNA encoding V region comprises DNAs coding for FR1, CDR1, FR2, CDR2, FR3, CDR3 and FR4 which are linked to each other in this order, as shown in FIG. 2.

First, mouse derived DNA fragments corresponding to respective CDRs are synthesized. CDRs 1 to 3 are synthesized on the basis of the base sequences of the previously cloned mouse H and L chain V regions. Grafting primers B and E are synthesized such that the primer B should have a sequence hybridizing to the mouse CDR1 and human antibody FR2 in the sense direction and the primer E should have a sequence hybridizing to the CDR1 and human antibody FR1 in the antisense direction (FIG. 2 (1)). Similarly, the grafting primers C and F and the primers D and G are synthesized. Further, suitable primers, called "external primers" and corresponding to A and H in FIG. 2 (1), which can hybridize to the regions upstream from FR1 and downstream from FR4, respectively, are also synthesized. Isolation and extraction of the grafting primers may be carried out in known procedures: Sambrook, et al., Molecular Cloning: A Laboratory Manual, Cold Spring Harbor Laboratory Press, 1989.

Then, first PCR is performed using the grafting primer E and external primer A, the grafting primers B and F, the grafting primers C and G as well as the grafting primer D and external primer H resulting in the formation of fragments A–E, B–F, C–G and D–H, respectively, (FIG. 2 (2)).

Since the upstream region of the grafting primer B and a part of the downstream region of the grafting primer E have been designed to overlap with each other (the same being true in the grafting primers C and F as well as D and G), these fragments may be annealed with respective complementary sequences by reacting under suitable temperature conditions and assembled to a DNA having a length from A to H by PCR. Once a DNA fragment coding for the V region is obtained, the external primers A and H may be added and second PCR may be performed to yield a DNA coding for the V region of a humanized antibody in which FRs 1 to 4 are human derived and CDRs 1 to 3 are mouse derived. Then, it may be introduced into a suitable host to express to yield the desired polypeptide (FIG. 2 (3)).

(ii) Construction of DNA and Experssion Vector Coding for Humanized a H Chain V Region In the present invention, the whole base sequence of a DNA coding for H chain V region of a human antibody to be used as a template for a humanized antibody may be synthesized by a DNA synthesizer and constructed by PCR method although said DNA is not available from the natural source.

The H chain V region of a mouse anti-human PTHrP monoclonal antibody has a high homology with S31679 belonging to human subgroup III. In order to employ this human antibody as a template to construct a DNA coding for a humanized H chain V region, four primers as shown in SEQ ID NOs:23–26, for example, are used. The primers MBC1HGP1 (SEQ ID NO:23) and MBC1HGP3 (SEQ ID NO:24) have sense DNA sequences and MBC1HGP2 (SEQ ID NO:25) and MBC1HGP4 (SEQ ID NO:26) have anti-sense DNA sequences. They are designed to each have a 15 to 21 bp complementary sequence at either end thereof.

External primers MBC1HVS1 (SEQ ID NO:27) and MBC1HVR1 (SEQ ID NO:28) have a homologous sequence with MBC1HGP1 and MBC1HGP4, respectively, and each comprises a recognition sequence for a respective suitable restriction enzyme. The four primers are assembled by PCR method to synthesize a full length cDNA, and the external primers are added to amplify the DNA. The "assembling by PCR method" herein involves annealing MBC1HGP1 and MBC1HGP2 or MBC1HGP3 and MBC1HGP4 through their complementary sequences to synthesize a MBC1HGP1-MBC1HGP3 fragment and a MBC1HGP2-MBC1HGP4 fragment and further annealing the fragments through their complementary sequences to synthesize the full length DNA for a humanized H chain V region.

Human antibody H chain C region may be any human H chain C region such as, for example, human H chain Cγ1, Cγ2, Cγ3 or Cγ4.

The DNA for H chain V region of a humanized antibody constructed as above described may be ligated to DNA for any human antibody H chain C region, for example, human H chain Cγ1 region. As mentioned in the section "Production of H chain of chimeric antibody", the DNA for H chain V region may be treated with a suitable restriction enzyme and ligated to a DNA coding for a human H chain C region under an expression control region such as an enhancer/promoter system to make an expression vector containing DNAs for a humanized H chain V region and a human H chain C region.

(iii) Construction of DNA and Experssion Vector Coding for Humanized L Chain V Region In the present invention, the whole base sequence of DNA coding for L chain V region of a human antibody to be used as a template may be synthesized by a DNA synthesizer and constructed by PCR method although the DNA for L chain V region is not available as in the case of the DNA coding for H chain V region.

In order to construct a DNA for a humanized L chain V region using as a template a human antibody SU03868 having a highest homology with the L chain V region of a mouse anti-human PTHrP monoclonal antibody, four primers as shown in SEQ ID NOs:29–32, for example, are used. The primers MBC1LGP1 (SEQ ID NO:29) and MBC1LGP3 (SEQ ID NO:30) have sense DNA sequences and MBC1LGP2 (SEQ ID NO:31) and MBC1LGP4 (SEQ ID NO:32) have antisense DNA sequences. They are designed to each have a 15 to 21 bp complementary sequence at either end thereof.

External primers MBC1LVS1 (SEQ ID NO:33) and MBC1LVR1 (SEQ ID NO:34) have a homologous sequence with MBC1LGP1 and MBC1LGP4, respectively, and each comprises a recognition sequence for a respective suitable restriction enzyme. The four primers are assemled by PCR method to synthesize a full length DNA, and the external primers are added to amplify the DNA. The "assemling by PCR method" herein involves annealing MBC1LGP1 and MBC1LGP3 or MBC1LGP2 and MBC1LGP4 through their complementary sequences to synthesize a MBC1LGP1-MBC1LGP3 fragment and a MBC1LGP2-MBC1LGP4 fragment and further annealing the fragments through their complementary sequences to synthesize a full length DNA coding for a humanized H chain V region.

Human antibody L chain C region may be any human L chain C region such as, for example, human L chain Cγ or Cκ.

The DNA for L chain V region of a humanized antibody constructed as above described may be ligated to DNA for any human antibody L chain C region, for example, human L chain CL region. The DNA for L chain V region may be treated with a suitable restriction enzyme and ligated to a DNA coding for a human Lλ chain C region under an expression control region such as an enhancer/promoter system to make an expression vector containing DNAs coding for a humanized L chain V region and a human Lγ chain C region.

Even if a polypeptide comprising a V region of a humanized antibody could be produced as above described, it is not necessarily clear whether or not said polypeptide would have an activity as an antibody, such as binding or neutralizing activity against its antigen. Particularly in the case of L chain, since the L chain V region of a mouse anti-human PTHrP monoclonal antibody is derived from a very rare Vλx gene, it should be necessary to investigate the presence or absence of the activity by combining it with a humanized H chain and expressing in an animal cell such as COS-7.

As a method for elucidating which FR in a humanized antibody V region may contribute to the binding and neutralizing activity of the humanized antibody, construction of a hybrid V region (Ohtomo, T. et al., Molecular Immunology, 32, 407–416, 1995) and confirmation may be effective. In order to elucidate which amino acid in the L chain V region of the humanized antibody according to the present invention should be mutated to provide one having the activity, a DNA in which a fragment of an FR region of a humanized antibody is recombined with a fragment of a mouse derived FR region is constructed and each region is assessed for humanization.

As shown in FIG. 3, an antibody having a polypeptide comprising a recombinant V region in which FR1 and FR2 are derived from a human antibody and FR3 and FR4 are derived from a mouse antibody (such an antibody having a recombinant fragment being referred to as a "hybrid antibody"), a hybrid antibody in which only FR1 is human derived, and a hybrid antibody in which only FR2 is human derived, are made. Each of DNAs coding for these hybrid antibodies is introduced into an expression vector and the humanized antibodies are temporarily expressed to investigate the presence of antibody activities.

Using this method, the present inventor has investigated polypeptides comprising L chain V regions for antigen binding and neutralizing activities and finally found that certain amino acids to be replaced exist in FR2 and FR3.

Having found that amino acids contributing to the activity exist in FR2 and FR3 regions, the present inventor has elucidated that the 36th, 45th and 49th amino acids in FR2 region and the 87th amino acid in FR3 region (the numbering of amino acids of antibodies having been determined by Kabat, E. A. et al., US Dep. Health and Human Services, US Government Printing Offices, 1991) contribute to the activity.

Thus, a polypeptide comprising a V region in which such amino acid(s) is/are mutated (e.g., replaced) is made in the present invention.

First, a polypeptide comprising a V region having an amino acid sequence as a base into which a mutation of amino acid(s) is to be introduced is prepared by the aforementioned CDR-grafting. This base polypeptide comprises the amino acid sequence as shown in SEQ ID NO:47 and is referred to as "version a" (a in Table 1).

Then, from the version a as a base, various variant fragments in which one or some amino acids of FR are mutated are made.

The introduction of mutation may be carried out by designing an oligonucleotide primer (mutagenic primer) coding for an amino acid to be introduced as a desired mutation and performing PCR using said primer.

Thus, polypeptides comprising V regions (versions b to t) in which a specific amino acid(s) in FR2 and FR3 is/are mutated are made (b to t in Table 1).

Table 1:

TABLE 1

|  | FR1 | CDR1 | | |
|---|---|---|---|---|
|  | 1         2         3 |  | | |
|  | 123456789012345678901234567890 | 12345 | | |
| MBC H. PEP | EVQLVESGGDLVKPGGSLKLSCAASGFTFS | SYGMS | | |
|  | *      ** *   *  * | | | |
| S31679 | QVQLVESGGGVVQPGRSLRLSCAASGFTFS | SYAMH | | |
| hMBCI-H. pep | ------------------------------ | SYGMS | | |
|  | FR2 | CDR2 | | |
|  | 4         5         6 | | | |
|  | 67890123456789  012A3456789012345 | | | |
| MBC H. PEP | WIRQTPDKRLEWVA  TISSGGSYTYYPDSVKG | | | |
|  | *  * * * | | | |
| S31679 | WVRQAPGKGLEWVA  VISYDGSNKYYADSVKG | | | |
| hMBC1-H. pep | --------------  TISSGGSYTYYPDSVKG | | | |
|  | FR3 | | CDR3 | FR4 |
|  | 7         8         9 | | 10 | 11 |
|  | 67890123456789012ABC345678901234 | | 567890A12 | 34567890123 |
| MBC H. PEP | RFTISRDNAKNTLYLQMSSLKSEDTAMFYCAR | | QTTMTYFAY | WGQGTLVTVSA |
|  | *       * **    ** | | | * |
| S31679 | RFTISRDNSKNTLYLQMNSLRAEDTAVYYCAR | | ESRGDY | WGQGTLVTVSS |
| hMBC1-H. pep | -------------------------------- | | QTTMTYFAY | ----------- |

TABLE 1-continued

|  | FR1<br>1         2<br>12345678901234567890123 | CDR1<br>3<br>4567A8901234 | FR2<br>4<br>567890123456789 | CDR2<br>5<br>01234ABCD56 |
|---|---|---|---|---|
| MBC L. PEP | QLVLTQSSS-ASFSLGASAKLTC<br>      *       *       * | TLSSQHSTYTIE | WYQQQPLKPPKYVMD<br>  *      * * * * * | LKQDGSHSTGD |
| HSU03868 | QLVLTQSPS-ASASLGASVKLTC | TLSSGHSSYAIA | WHQQQPEKGPRYLMK | LNSDGSHSKGD |
| hMBC1-L. pep | ----------------------- | TLSSQHSTYTIE | --------------- | LKQDGSHSTGD |
| a | ----------------------- | ------------ | --------------- | ----------- |
| b | ----------------------- | ------------ | --------P-----D | ----------- |
| c | ----------------------- | ------------ | --------------- | ----------- |
| d | ----------------------- | ------------ | --------------- | ----------- |
| e | ----------------------- | ------------ | --------P-----D | ----------- |
| f | ----------------------- | ------------ | --------------- | ----------- |
| g | ----------------------- | ------------ | -Y------------- | ----------- |
| h | ----------------------- | ------------ | -Y------------- | ----------- |
| i | ----------------------- | ------------ | -Y--------K---- | ----------- |
| j | ----------------------- | ------------ | -Y--------K---D | ----------- |
| k | ----------------------- | ------------ | -Y--------K-V-- | ----------- |
| l | ----------------------- | ------------ | -Y--------K-V-D | ----------- |
| m | ----------------------- | ------------ | -Y------------D | ----------- |
| n | ----------------------- | ------------ | -Y----------V-- | ----------- |
| o | ----------------------- | ------------ | -Y----------V-D | ----------- |
| p | ----------------------- | ------------ | -Y--------K---- | ----------- |
| q | ----------------------- | ------------ | -Y--------K---D | ----------- |
| r | ----------------------- | ------------ | -Y------------D | ----------- |
| s | ----------------------- | ------------ | -Y--------K-V-D | ----------- |
| t | ----------------------- | ------------ | -Y----------V-D | ----------- |

|  | FR3<br>         6         7         8<br>7890123456789012345678901234 5678 | CDR3<br>9<br>9012345ABCD67 | FR4<br>10        11<br>890123456A7890 |
|---|---|---|---|
| MBC L. PEP | GIPDRFSGSSSGADRYLSISNIQPEDEAMYIC<br>       *     *   ** *    * * | GVGDTIKEQFVYV | FGGGTKVTVLGQP |
| HSU03868 | GIPDRFSGSSSGAERYLTISSLQSEDEADYYC | QTWGTGI | |
| hMBC1-L.pep | ------------------------------- | GVGDTIKEQFVYV | ------L------ |
| a | ------------------------------- | ------------- | ------L------ |
| b | ------------------------------- | ------------- | ------L------ |
| c | --------------------P---------- | ------------- | ------L------ |
| d | ----------------------------I-- | ------------- | ------L------ |
| e | ----------------------------I-- | ------------- | ------L------ |
| f | --------------------P-------I-- | ------------- | ------L------ |
| g | ------------------------------- | ------------- | ------L------ |
| h | ----------------------------I-- | ------------- | ------L------ |
| i | ------------------------------- | ------------- | ------L------ |
| j | ------------------------------- | ------------- | ------L------ |
| k | ------------------------------- | ------------- | ------L------ |
| l | ------------------------------- | ------------- | ------L------ |
| m | ------------------------------- | ------------- | ------L------ |
| n | ------------------------------- | ------------- | ------L------ |
| o | ----------------------------I-- | ------------- | ------L------ |
| p | ----------------------------I-- | ------------- | ------L------ |
| q | ----------------------------I-- | ------------- | ------L------ |
| r | ----------------------------I-- | ------------- | ------L------ |
| s | ----------------------------I-- | ------------- | ------L------ |
| t | ----------------------------I-- | ------------- | ------L------ |

The DNA cording for each version of L chain V region of a humanized antibody as constructed above may be ligated to a DNA of any L chain C region of a human antibody, such as human L chain Cλ region. Thus, it is treated with a suitable restriction enzyme and ligated to a DNA coding for a human Lλ chain C region under the control of an expression control region such as an enhancer/promoter system to construct an expression vector comprising a DNA coding for each version of the humanized L chain V region and a DNA coding for the humanized Lλ chain C region.

The DNA coding for H chain V region of a humanized antibody and a human H chain C region as previously constructed and the DNA coding for a humanized L chain V region and human L chain C region may also be introduced into a single expression vector such as that disclosed in WO94/11523, said vector may be used to transform a host cell, and the transformed host may be cultivated in vivo or in vitro to produce a desired humanized antibody.

4. Production of Chimeric Antibody and Humanized Antibody

To produce a chimeric or humanized antibody, two expression vectors as above mentioned should be prepared. Thus, with respect to a chimeric antibody, an expression vector comprising a DNA coding for a mouse H chain V region and a human H chain C region under the control of an expression control region such as an enhancer/promoter system, and an expression vector comprising a DNA coding for a mouse L chain V region and a human L chain C region under the control of an expression control region such as an enhancer/promoter system are constructed. With respect to a humanized antibody, an expression vector comprising a DNA coding for a humanized H chain V region and a human H chain C region under the control of an expression control region such as an enhancer/promoter system, and an expression vector comprising a DNA coding for a humanized L chain V region and a human L chain C region under the control of an expression control region such as an enhancer/promoter system are constructed.

Then, a host cell such as a mammalian cell is cotransformed with these expression vectors and the resulting transformed cell is cultivated in vitro or in vivo to produce the chimeric or humanized antibody (see, for example, WO91/16928).

Alternatively, a DNA coding for H chain V and C regions and a DNA coding for L chain V and C regions may be ligated to a single vector and transformed into a suitable host cell to produce an antibody. Thus, in the expression of a chimeric antibody, a DNA coding for a mouse leader sequence present in the cloned cDNA, a mouse H chain V region and a human H chain C region as well as a DNA coding for a mouse leader sequence, a mouse L chain V region and a human L chain C region, are introduced into a single expression vector such as one disclosed in e.g. WO94/11523. In the expression of a humanized antibody, a DNA coding for a humanized H chain V region and a human H chain C region and a DNA coding for a humanized L chain V region and a human L chain C region are introduced into a single expression vector such as one disclosed in e.g. WO94/11523. Such a vector is used to transform a host cell and the transformed host is cultivated in vivo or in vitro to produce a chimeric or humanized antibody of interest.

The chimeric or humanized antibody of interest which is thus produced by cultivating the transformant transformed with a DNA coding for said chimeric or humanized antibody may be isolated from the interior or exterior of the cell and purified to uniformity.

The isolation and purification of the chimeric or humanized antibody of interest according to the present invention may be carried out by using a protein A agarose column, but may also be performed by any methods used in isolation and purification of conventional proteins and thus is not limited. For instance, various chromatography, ultrafiltration, salting out and dialysis may optionally be selected or combined to isolate and purify the chimeric or humanized antibody.

Any expression system may be used to produce the chimeric or humanized antibody against human PTHrP according to the present invention. For example, eukaryotic cells include animal cells such as established mammalian cell lines, mold and fungal cells, and yeast cells; prokaryotic cells include bacterial cells such as *Escherichia coli* cells. Preferably, the chimeric or humanized antibody of the present invention is expressed in a mammalian cell such as COS or CHO cell.

Any conventional promoters useful for the expression in mammalian cells may be used. For example, human cytomegalovirus immediate early (HCMV) promoter is preferably used. Examples of expression vectors comprising HCMV promoter include HCMV-VH-HCγ 1 and HCMV-VL-HCK derived from pSV2neo (WO92/19759).

In addition, promoters for gene expression in mammalian cells which can be used in the present invention may include virus promoters, such as those of retrovirus, polyoma virus, adenovirus and simian virus (SV) 40, and mammalian cell derived promoters, such as those of human polypeptide chain elongation factor-1α (HEF-1α). For example, SV40 promoter may be readily used according to Mulligan et al. method (Nature, 277, 108, 1979); Mizushima, S. et al. method (Nucleic Acids Research, 18, 5322, 1990) may be easily used with HEF-1α promoter.

Origin of replication usable herein includes those derived from SV40, polyoma virus, adenovirus or bovine papilloma virus (BPV). Further, the expression vector may comprise a gene for phosphotransferase APH(3') II or I (neo), thymidine kinase (TK), *E. coli* xanthine-guanine phosphoribosyltransferase (Ecogpt) or dihydrofolate reductase (DHFR) as a selective marker for increasing the gene copy number in a host cell system.

5. Evaluation of Antigen Binding and Neutralizing Activity of Chimeric and Humanized Antibodies (1) Determination of Antibody Concentration The concentration of the resulting purified antibody can be determined by ELISA.

ELISA plates for determining the antibody concentration are prepared in the following manner: 100 μl of a goat anti-human IgG antibody prepared at a concentration of e.g. 1 μg/ml is immobilized in each well of a 96 well plate for ELISA (for example, Maxisorp, NUNC). After blocking with 200 μl of a diluting buffer (for example, 50 mM Tris-HCl, 1 mM $MgCl_2$, 0.1 M NaCl, 0.05% Tween20, 0.02% $NaN_3$, 1% bovine serum albumin (BSA), pH 7.2), a stepwise diluted supernatant of COS-7 or CHO cells in which the chimeric, hybrid or humanized antibody has been expressed, or purified chimeric, hybrid or humanized antibody is added to each well, 100 μl of an alkaline phosphatase-conjugated goat anti-human IgG antibody is added, and 1 mg/ml of a substrate solution (Sigma 104, p-nitrophenylphosphoric acid, SIGMA) is then added, after which the absorbance at 405 nm is measured by a microplate reader (Bio Rad). Hu IgG1λ Purified (The Binding Site) may be used as a standard for the determination of concentrations.

(2) Determination of Antigen Binding Ability

ELISA plates for determining the antigen binding ability are prepared in the following manner: 100 μl of human PTHrP (1–34) prepared at a concentration of 100 μl/ml is immobilized to each well of a 96 well plate for ELISA. After blocking with 200 μl of a diluting buffer, a stepwise diluted supernatant of COS-7 or CHO cells in which the chimeric, hybrid or humanized antibody has been expressed, or purified chimeric, hybrid or humanized antibody is added to each well, 100 μl of an alkaline phosphatase-conjugated goat anti-human (3) Determination of Neutralizing Activity Determination of the neutralizing activity of the mouse, chimeric and humanized antibodies can be carried out by, e.g., using rat osteosarcoma cell line ROS17/2.8–5 cell (Sato, K. et al., Acta Endocrinology, 116, 113–120, 1987). Thus, ROS17/2.8–5 cells are stimulated by 4 mM hydrocortisone to induce PTH/PTHrP receptor. The degradative enzyme for cAMP is inhibited with 1 mM of isobutyl-1-methyl xanthine (IBMX, SIGMA). The mouse, chimeric or humanized antibody to be determined for neutralizing activity is mixed with an equal amount of PTHRP (1–34) and the resulting mixture of each antibody and PTHrP (1–34) is added to each well. The neutralizing ability of the mouse, chimeric or humanized antibody can be estimated by measuring the amount of cAMP produced by rat osteosarcoma cell lines ROS17/2.8–5 cells due to stimulation with PTHrP.

(4) Kinetic Analysis of Interactions Between PTHrP and Anti-PTHrP Antibody

In the present invention, the kinetics in the interactions between PTHrP and anti-PTHrP may be analyzed by a variety of means and procedures. Specifically, dissociation constants, dissociation rate constants and association rate constants may be measured by Scatchard analysis and a surface plasmon resonance sensor called BIACORE (developed and commercialized by Pharmacia Biotech). Analysis by a surface plasmon resonance sensor called BIACORE will be described hereininbelow as one example.

The basic structure of BIACORE comprises an optical source, a prism, a detector and a micro-passage. In practice, a ligand is immobilized on a cassette-type sensor tip and an analyte is injected thereinto. When there is any affinity between them, the binding amount is optically detected.

The detecting principle is a phenomenon called surface plasmon resonance. Thus, of incident light injected to the interface between a glass and a metal film so that total reflection should occur, the incident light at a certain angle is used to excite surface plasmon and damped. The angle vary depending upon the change in concentration of a solvent in contact with the metal film (sensor). BIACORE detects this change.

In BIACORE, this change is called a resonance signal (SPR signal) and a change of 0.1 degree is 1000 RU (resonance units). 1000 RU corresponds to a change in the binding of about 1 ng of a protein onto a thin gold sensor of 1 $mm^2$ in surface area. For a protein, a change of about 50 RU (50 pg) can be fully detected.

The detected signals are converted into a binding curve called a sonsorgram by a computor attached to BIACORE, which is drawn on a computor display in real time: Natsume, T., et al. (1995) Experimental Medicine, 13, 563–569; Karlsson, R., et al. (1991) J. Immunol. Methods 145, 229–240.

Kinetics parameters, i.e., dissociation constant (KD), dissociation rate constant (Kdiss) and association rate constant (Kass), of the anti-PTHrP antibodies of the present invention may be measured by the above mentioned BIACORE.

The anti-PTHrP antibodies of the present invention preferably have as small a dissociation constant (KD value) as possible in view of neutralizing activity. Preferably, the anti-PTHrP antibodies of the present invention have a KD value $1.86 \times 10^{-7}$ or less, more preferably $1.86 \times 10^{-8}$ or less, most preferably $3.58 \times 10^{-10}$ or less.

The KD values are determined from two parameters, dissociation rate constants (Kdiss) and association rate constants (Kass) (KD=Kdiss/Kass). Apparently, therefore, the KD values are smaller when the Kdiss values are smaller and the Kass values are larger.

Specifically, the Kdiss values of the anti-PTHrP antibodies according to the present invention may be $1.22 \times 10^{-1}$ [1/Sec] or less. Preferably, the Kdiss values are $1.22 \times 10^{-2}$ or less, more preferably $3.16 \times 10^{-4}$ or less, most preferably $2.32 \times 10^{-4}$ [1/Sec] or less.

On the other hand, the Kass values may be $6.55 \times 10^4$ [1/M.Sec] or more. Preferably, the Kass values are $6.55 \times 10^5$ or more, more preferably $0.883 \times 10^6$ or more, most preferably $1.03 \times 10^6$ [1/M.Sec] or more.

Further, also preferred are anti-PTHrP antibodies having a Kdiss value of $1.22 \times 10^{-1}$ [1/Sec] and a Kass value of $6.55 \times 10^4$ [1/M.Sec] or more.

More specifically, the anti-PTHrP antibodies of the present invention have a KD value in the range of $1.02 \times 10^{-11}$ to $1.86 \times 10^{-7}$ [M], preferably $1.02 \times 10^{-10}$ to $1.86 \times 10^{-8}$ [M], more preferably $1.34 \times 10^{-10}$ to $3.58 \times 10^{-10}$ [M], most preferably $2.25 \times 10^{-10}$ to $3.58 \times 10^{-10}$ [M].

The Kdiss values are in the range of $7.38 \times 10^{-6}$ to $1.22 \times 10^{-1}$ [1/Sec], preferably $7.38 \times 10^{-5}$ to $1.22 \times 10^{-2}$ [1/Sec], more preferably $1.66 \times 10^{-4}$ to $3.16 \times 10^{-4}$ [1/Sec], most preferably $1.66 \times 10^{-4}$ to $2.32 \times 10^{-4}$ [1/Sec].

The Kass values are in the range of $6.55 \times 10^4$ to $1.24 \times 10^7$ [1/M.Sec], preferably $6.55 \times 10^5$ to $1.24 \times 10^6$ [1/M.Sec], more preferably $7.23 \times 10^5$ to $1.03 \times 10^6$ [1/M.Sec], most preferably $0.883 \times 10^6$ to $1.03 \times 10^6$ [1/M.Sec].

These KD, Kdiss and Kass values may be obtained by Scatchard analysis or a surface plasmon resonance sensor such as BIACORE, preferably by BIACORE.

6. Pharmaceutical Composition and Hypercalcemia-Suppressing Agent Comprising Anti-PTHrP or Humanized Antibody as Effective Ingredient.

The therapeutic effect of the humanized antibody on PTHrP may be confirmed by administering the antibody against PTHrP or the humanized antibody to an animal exhibiting hypercalcemia and measuring an index for hypercalcemia. In animals exhibiting hypercalcemia and patients suffering from hypercalcemia, hypophosphatemia is often observed; the antibodies of the present invention may also be used to improve the hypophosphatemia.

The antibody used in the present invention is an anti-PTHrP antibody including human, chimeric and primatized antibodies or a humanized antibody against PTHrP having the dissociation constant, dissociation rate constant and association rate constant. The antibody will neutralize the activity of PTHrP by binding to PTHrP and preferably includes, in particular, humanized #23-57-137-1 antibody. The method for producing the humanized #23-57-137-1 antibody will be described in Examples 1 to 3.

The antibody used in the present invention can be purified to a high purity by any combination of conventional purification means such as salting out, gel filtration using HPLC etc., and affinity chromatography using a protein A column etc. Recognition of PTHrP by the thus purified antibody with a high accuracy may be confirmed by any conventional immunological means such as radioimmunoassay (RIA), enzyme immunoassay (EIA, ELISA) or immunofluorescence analysis.

The animal exhibiting hypercalcemia which may be used includes a model animal prepared by transplanting PTHrP-producing tumor cells to an experimental animal with reduced or deleted immunological function. The tumor cells transplanted are preferably human derived ones including, for example, human pancrea cancer PAN-7. The animal with reduced or deleted immunological function to which the tumor cells are transplanted includes nude mouse and SCID mouse.

Suppression of hypercalcemia may be evaluated by observing the concentration of calcium in the blood, the reduction of body weight or the reduction of extent of movement with the lapse of time and determining the degree of improvement.

The pharmaceutical composition and hypercalcemia suppressing agent comprising the antibody or humanized antibody against PTHrP as an effective ingredient according to the present invention may be parenterally administered systemically or topically. For example, intravenous injection including drip, intramuscular injection, intraperitoneal injection or subcutaneous injection may be selected. The method of administration may be properly selected depending on the age of a patient and the conditions of disease. An effective single dose may be selected from the range of 0.01 to 1,000 mg per kg of body weight. Alternatively, the dose to a patient may be 5 to 10,000 mg/body, preferably 50 to 1,000 mg/body.

The pharmaceutical composition and hypercalcemia suppressing agent comprising the antibody or humanized antibody against PTHrP as an effective ingredient according to the present invention may further comprise a pharmaceutically acceptable carrier and/or additive(s) depending upon the administration route. Examples of such carrier and additive may include water, pharmaceutically acceptable organic solvents, collagen, polyvinyl alcohol, polyvinyl pyrrolidone, carboxyvinyl polymer, sodium carboxymethyl cellulose, poly(sodium acrylate), sodium arginate, water soluble dextran, sodium carboxymethyl starch, pectin, methyl cellulose, ethyl cellulose, xanthane gum, gum arabic, casein, gelatin, agar, diglycerin, glycerin, propylene glycol, polyethylene glycol, vaseline, paraffin, stearyl alcohol, stearic acid, human serum albumin (HSA), mannitol, sorbitol, lactose, and surfactants acceptable as pharmaceutical additives. The additives used may be properly selected from the above either alone or in combination, but not limited thereto.

The antibody of the present invention may be used widely in hypercalcemia associated with various cancers (malignant tumors). These cancers are not particularly limited and include not only a single cancer but also a combination of a plurality of cancers. The cancers may include for example pancreas, lung, pharynx, larynx, tongue, gingiva, esophagus, stomach, biliary duct, breast, kidney, urinary bladder, uterus and prostate cancers, and malignant lymphoma.

EXAMPLE

Figure 1:
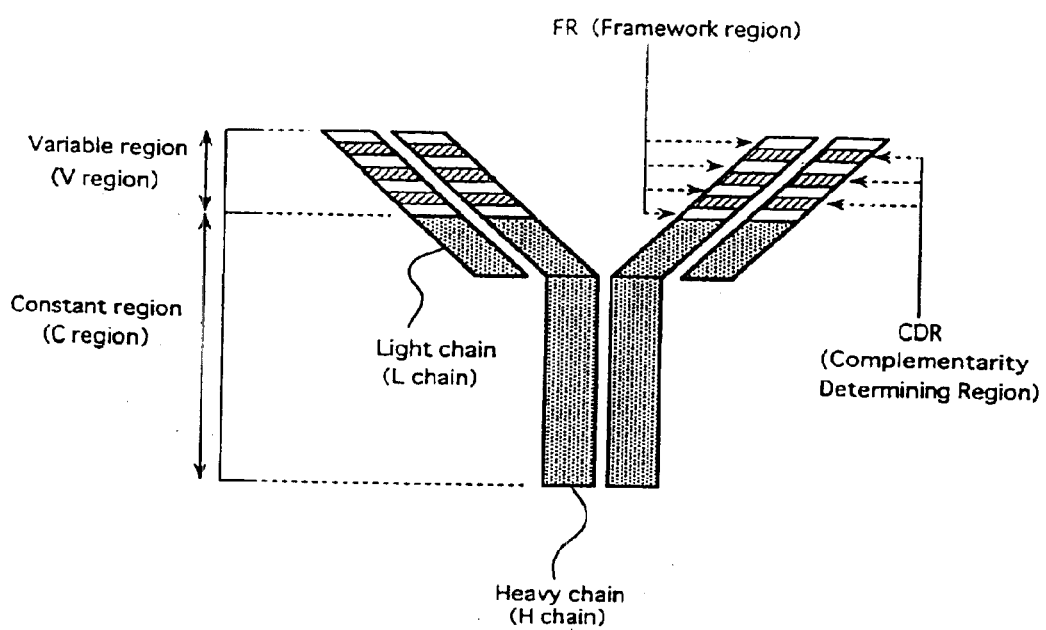
FIG. 1 is a schematic illustration of the antibody according to the present invention.
Figure 2:
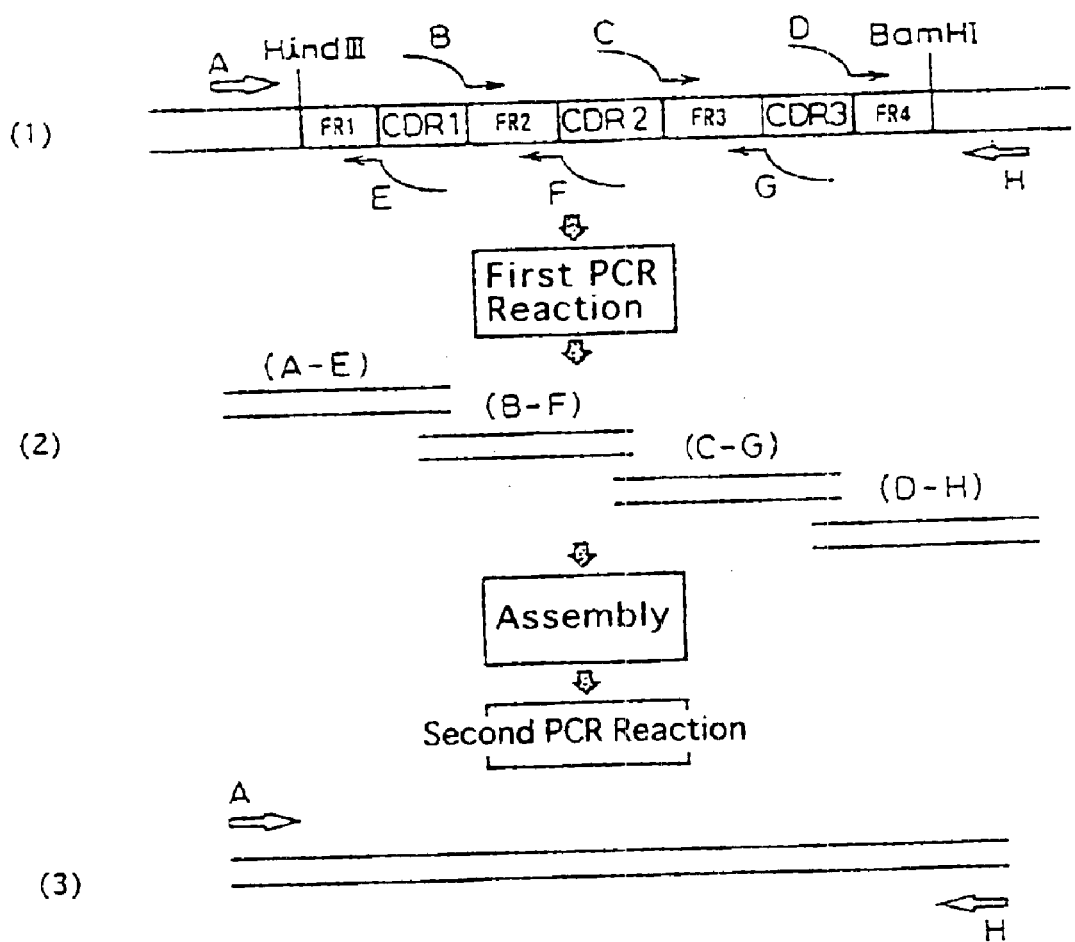
FIG. 2 is a schematic illustration of the CDR-grafting.
Figure 3:
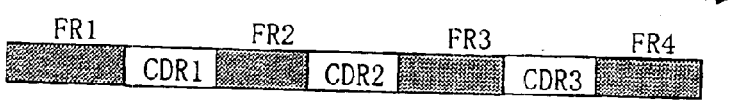
FIG. 3 is an illustration of the determination of the FRs and the CDRs of the V region.

Hereinbelow, the present invention will be described in more detail with reference to the following Examples, which should not be construed as limiting the scope of the invention.

Reference Example 1

Preparation of Anti-PTHrP (1–34) Mouse Monoclonal Antibody Producing Hybridoma

Hybridomas capable of producing a monoclonal antibody against human PTHrP (1–34), #23-57-154 and #23-57-137-1, were prepared in accordance with the method reported by Kanji Sato et al. (Sato, K. et al., J. Bone Miner. Res. 8, 849–860, 1993).

The immunogen used was PTHrP (1–34) (Peninsula), to which a carrier protein, thyroglobulin, was conjugated using carbodiimide (Dojinn). The thycloglobulin-conjugated PTHrP (1–34) was dialyzed to obtain a solution having a protein concentration of 2 μg/ml. The resultant solution was mixed with Freund's adjuvant (Difco) in a mixing ratio of 1:1 to obtain an emulsion. This emulsion was injected to each of 16 female BALB/C mice dorsal-subcutaneously or intraperitoneally in a dose amount of 100 μg/mouse to immunize the mice. The injection was conducted 11 times. With respect to the adjuvant, Freund's complete adjuvant was used in the injection for the first immunization, and Freund's incomplete adjuvant was used in the injection for subsequent immunizations.

Each of the mice immunized was determined for its antibody titers in the sera in the following manner:

Each of the mice was blood-drawn from its tail vein and the blood was then subjected to centrifugation to obtain a serum. The serum was diluted with a RIA buffer, mixed with $^{125}$I-labeled PTHrP (1–34), and subjected to determination of its binding activity. The mice which have been confirmed to have a satisfactorily high antibody titer were injected with PTHrP (1–34) without the carrier protein intraperitoneally in a dose amount of 50 μg/mouse for the final immunization.

Three days after the final immunization, the mice were sacrificed and excised their spleens. Thereafter, spleen cells were subjected to cell fusion with mouse myeloma cell line P3×63Ag8U. 1 in accordance with a conventional known method using 50% polyethylene glycol 4000. The fused cells thus prepared were inoculated into each well of 85 of 96-well plates in an amount of 2×10$^4$/well. The screening of hybridomas of interest was conducted using a HAT medium as follows.

The screening of the hybridomas was conducted by determining for the presence of PTHrP-recognition antibodies in the culture supernatant with respect to the wells in which cell growth had been observed in the HAT medium by a solid phase RIA method. The hybridomas were collected from the wells in which the binding ability to the PTHrP-recognition antibody was confirmed. The hybridomas thus obtained was suspended into a RPMI-1640 medium containing 15% FCS and supplemented with OPI-supplement (Sigma), followed by unification of the hybridomas by a limiting dilution method, thereby obtaining two types of hybridoma clones, #23-57-154 and #23-57-137-1 both exhibiting a strong binding ability to PTHrP (1–34).

Hybridoma clone #23-57-137-1, which was designated "mouse—mouse hybridoma #23-57-137-1", has been deposited under the terms of the Budapest Treaty on Aug. 15, 1996 at the National Institute of Bioscience and Human-technology, Agency of Industrial Science and Technology, Japan (1–3, Higashi 1-chome, Tsukuba-shi, Ibaragi-ken, Japan) under the accession No. FERM BP-5631.

EXAMPLE 1

Cloning of DNA Coding for V Region of Mouse Monoclonal Antibody Against Human PTHrP (1–34)

Cloning of the DNA coding for the V region of the mouse monoclonal antibody against human PTHrP (1–34) obtained above, #23-57-137-1, was conducted in the following manner.
(1) Preparation of mRNA mRNA was prepared from hybridoma #23-57-137-1 using Quick Prep mRNA Purification Kit (Pharmacia Biotech) as follows.

The cells of hybridoma #23-57-137-1 obtained above were fully homogenized with an extraction buffer, and mRNA was extracted therefrom using an oligo(dT)-Cellulose Spun Column in accordance with the procedure by the manufacturer of the kit. The extraction solution was subjected to ethanol precipitation to obtain the mRNA as precipitates. The mRNA precipitates were dissolved in an elution buffer.
(2) Preparation and Amplification of cDNA of the Gene Coding for Mouse H Chain V Region
(i) Cloning of cDNA for H Chain V Region of #23-57-137-1 Antibody A DNA coding for the H chain V region of the mouse monoclonal antibody against human PTHrP was cloned by a 5'RACE method (Frohman, M. A. et al., Proc. Natl. Acad. Sci. USA, 85, 8998–9002, 1988; Belyavsky, A. et al., Nucleic Acids Res. 17, 2919–2932, 1989). This method was conducted using 5'-Ampli FINDER RACE Kit (CLONETECH) in accordance with the procedure by the manufacturer. In this method, the primer used for synthesis of cDNA was MHC2 primer (SEQ ID NO: 1) which is hybridizable with mouse H chain C region. About 2 μg of the above-obtained mRNA, which was a template for cDNA synthesis, was mixed with 10 pmoles of MHC2 primer. The resultant mixture was reacted with a reverse transcriptase at 52° C. for 30 min to prepare a cDNA which was complementary to the mRNA.

The resultant was mixed with 6N NaOH to hydrolyze the mRNA therein (at 65° C. for 30 min.) and then subjected to ethanol precipitation to isolate the cDNA as precipitates. The cDNA thus isolated was ligated to Ampli FINDER Anchor (SEQ ID NO: 42) on its 5'-end by reacting with T4 RNA ligase at 37° C. for 6 hours and additionally at room temperature for 16 hours. As the primers for amplification of the cDNA by a PCR method, Anchor primer (SEQ ID NO: 2) and MHC-G1 primer (SEQ ID NO: 3) (S. T. Jones, et al., Biotechnology, 9, 88, 1991) were used.

The PCR solution (50 μl) used in this method comprised 10 mM Tris-HCl (pH 8.3), 50 mM KC1, 0.25 mM dNTPs (dATP, dGTP, dCTP, dTTP), 1.5 mM MgCl$_2$, 2.5 units of TaKaRa Taq (Takara Shuzo), 10 pmoles Anchor primer, and 1 μl of the reaction mixture of the cDNA to which MHC-G1 primer and Ampli FINDER Anchor primer had been ligated, over which 50 μl of mineral oil was layered. Thirty cycles of the PCR reaction was conducted using Thermal Cycler Model 480J (Perkin Elmer) and a temperature cycle of 94° C. for 45 sec.; 60° C. for 45 sec.; and 72° C. for 2 min.
(ii) Cloning of cDNA for #23-57-137-1 Antibody L Chain V Region A DNA coding for L chain V region of the mouse monoclonal antibody against human PTHrP was cloned by the 5'-RACE method (Frohman, M. A. et al., Proc. Natl. Acad. Sci. USA, 85, 8998–9002, 1988; Belyavsky, A. et al., Nucleic Acids Res. 17, 2919–2932, 1989). This method was conducted using 5'-Ampli Finder RACE Kit (Clonetech) in accordance with the procedure by the manufacturer. In this method, oligo-dT primer was used as the primer for synthesizing a cDNA. About 2 μg of the above-mentioned mRNA (which was a template for cDNA synthesis) was mixed with oligo-dT primer. The resultant mixture was reacted with a reverse transcriptase at 52° C. for 30 min. to prepare a cDNA. The resultant was mixed with 6N NaOH to hydrolyze the RNA therein (at 65° C. for 30 min.). The resultant mixture was subjected to ethanol precipitation to isolate the cDNA as precipitates. The cDNA thus synthesized was ligated to the Ampli FINDER Anchor on its 5'-end by reacting with T4 RNA ligase at 37° C. for 6 hours and additionally at room temperature for 16 hours.

PCR primer MLC (SEQ ID NO: 4) was designed based on the conserved sequence of a mouse L chain λ chain C region and then synthesized using 394 DNA/RNA Synthesizer (ABI). The PCR solution (100 μl) used for the synthesis of the primer comprised 10 mM Tris-HCl (pH 8.3), 50 mM KCl, 0.25 mM dNTPs (dATP, dGTP, dCTP, dTTP), 1.5 mM MgCl$_2$, 2.5 units of AmpliTaq (PERKIN ELMER), 50 pmoles of Anchor primer (SEQ ID NO: 2), and 1 μl of the reaction mixture of the cDNA to which MLC (SEQ ID NO: 4) and Ampli FINDER Anchor were ligated, over 50 μl of mineral oil was layered. Thirty-five cycles of the PCR reaction was conducted using Thermal Cycler Model 480J (Perkin Elmer) and a temperature cycle of 94° C. for 45 sec.; 60° C. for 45 sec.; and 72° C. for 2 min.
(3) Purification and Fragmentation of the PCR Product Each of the DNA fragments amplified by the PCR methods described above was separated by agarose gel electrophoresis using 3% Nu Sieve GTG agarose (FMC Bio. Products). For each of the H chain V region and the L chain V region, agarose gel fraction containing a DNA fragment of about 550 bp in length was excised from the gel, respectively. Each of the gel fractions obtained was subjected to purification of the DNA therefrom using GENECLEAN II Kit (BIO101) in accordance with the procedure by the manufacturer. The purified DNA was precipitated from the solution with ethanol and then dissolved in 20 µl of a solution containing 10 mM Tris-HCl (pH 7.4) and 1 mM EDTA. One µl of the DNA solution thus prepared was digested with restriction enzyme XmaI (New England Biolabs) at 37° C. for 1 hour and additionally with restriction enzyme EcoRI (Takara Shuzo) at 37° C. for 1 hour. The digestion mixture was subjected to extraction with phenol and chloroform and then precipitation with ethanol to collect the DNA.

In this manner, obtained a DNA coding for the mouse H chain V region and a DNA coding for the mouse L chain V region, both which had an EcoRI recognition sequence on the 5'-end and an XmaI recognition sequence on the 3'-end thereof were obtained.

Each of the EcoRI-XmaI DNA fragments containing a DNA coding for the mouse H chain V region and a DNA coding for the mouse L chain V region, respectively, was reacted with pUC19 vector, which had been digested with EcoRI and XmaI, at 16° C. for 1 hour using DNA Ligation Kit ver.2 (Takara Shuzo) in accordance with the procedure by the manufacturer to ligate to each other. The ligation mixture (10 µl) thus obtained was added to 100 µl of a solution containing competent cells of *E. coli*, JM 109 (Nippon Gene). The cell mixture was allowed to stand for 15 min. on ice, at 42° C. for 1 min. and further for 1 min. on ice. The resultant was mixed with 300 µl of SOC culture medium (Molecular Cloning: A Laboratory Manual, Sambrook, et al., Cold Spring Harbor Laboratory Press, 1989) and then incubated at 37° C. for 30 min. The resultant cell solution was spread on a LB or 2×YT agar medium (Molecular Cloning: A Laboratory Manual, Sambrook, et al., Cold Spring Harbor Laboratory Press, 1989) supplemented with 100 or 50 µg/ml of ampicillin, 0.1 mM of IPTG and 20 µg/ml of X-gal and then incubated at 37° C. overnight. In this manner, *E. coli* transformants were prepared.

The transformants were cultured overnight in 2 ml of a LB or 2×YT medium containing 100 or 50 µg/ml of ampicillin at 37° C. and then plasmid DNA was prepared from the cell fraction using Plasmid Extracter PI-100Σ (Kurabou) or QIAprep Spin Plasmid Kit (QIAGEN). The plasmid DNAs thus obtained were determined for their DNA sequences.

(4) Sequencing of cDNA Coding for V Region of Mouse Antibody

The sequence of the cDNA coding region carried on the plasmid was determined by DNA Sequencer 373A (ABI; Perkin-Elmer) using Dye Terminator Cycle Sequencing Kit (Perkin-Elmer). This DNA sequence was determined by confirming the base sequence in the both orientations using primers, M13 Primer M4 (Takara Shuzo) (SEQ ID NO: 5) and M13 Primer RV (Takara Shuzo) (SEQ ID NO: 6).

The plasmids thus obtained, which contained a cDNA coding for the mouse H chain V region and a cDNA coding for the mouse L chain V region derived from hybridoma #23-57-137-1, were designated "MBC1HO4" and "MBC1L24", respectively. The sequences (including the corresponding amino acids sequences) of the DNA coding for the H chain V region and the DNA coding for the L chain V region of mouse #23-57-137-1 antibody (respectively carried on plasmid MBC1H04 and plasmid MBC1H24) were shown in SEQ. ID NOs: 57 and 65, respectively. Both of the polypeptides for the H chain V region fragment and for the L chain V region fragment were translated starting from the 58th base (which coding for glutamine) in the DNA sequences shown in SEQ ID NOs: 57 and 65. The amino acid sequences for the H chain V region and the L chain V region were shown in SEQ. ID NOs: 46 and 45, respectively.

The *E. coli* having plasmid MBC1HO4 and the *E. coli* having plasmid MBC1L24 were designated "*Escherichia coli* JM109 (MBC1H04)" and "*Escherichia coli* JM109 (MBC1L24)", respectively. These *E. coli* strains have been deposited under the terms of the Budapest Treaty at the National Institute of Bioscience and Human-Technology, Agency of Industrial Science and Technology, Japan (1–3, Higashi 1-chome, Tsukuba-shi, Ibaragi-ken, Japan) on Aug. 15, 1996 under the Accession No. FERM BP-5628 for *Escherichia coli* JM109 (MBC1H04) and FERM BP-5627 for *Escherichia coli* JM109 (MBC1L24), respectively.

(5) Determination of CDR of Mouse Monoclonal Antibody #23-57-137-1 Against Human PTHrP The general structures of the H chain V region and the L chain V region are similar to each other. That is, both structures have four framework regions ligated through three hypervariable regions [i.e., complementarity determining regions (CDRs)]. The amino acid sequences of the framework regions are relatively well conserved, while the amino acid sequences of the CDR regions exhibit an extremely high mutagenicity (Kabat, E. A. et al., "Sequence of Proteins of Immunological Interest", US Dept. Health and Human Services, 1983).

On the basis of the above-mentioned facts, the CDRs were determined by searching the homology of amino acid sequences of the mouse monoclonal antibody V region by reference to the Date Base of amino acid sequences for antibodies established by Kabat et al.

The amino acid sequences of CDRs 1–3 in the L chain V region are shown in SEQ ID Nos: 59–61, respectively, and the amino acid sequences of DCRs 1–3 in the H chain V region are shown in SEQ ID Nos: 62–64, respectively.

TABLE 2

| V region | SEQ ID NO. | CDR1 | CDR2 | CDR3 |
| --- | --- | --- | --- | --- |
| H chain V region | 57 | 31–35 | 50–66 | 99–107 |
| L chain V region | 65 | 23–34 | 50–60 | 93–105 |

EXAMPLE 2

Construction of Chimeric Antibody (1) Construction of Chimeric Antibody H Chain (i) Construction of H Chain V Region The cloned cDNA coding for mouse H chain V region was modified by a PCR method to ligate it to an expression vector carrying the genomic DNA for the human H chain C region Cγ1. The downstream-side primer MBC1-S1 (SEQ ID NO: 7) used was designed so as to be hybridizable to the DNA coding for the 51'-end region of the leader sequence of the V region and to have both a Kozak consensus sequence (Kozak, M. et al., J. Mol. Biol., 196, 947–950, 1987) and a HindIII-recognition sequence. The upstream-side primer, MBC1-a (SEQ ID NO: 8), used was designed so as to be hybridizable to the DNA coding for the 3'-end region of the J region and to have both a splice donor sequence and a BamHI-recognition sequence. The PCR reaction was conducted using TaKaRa Ex Taq (Takara Shuzo) and a buffer appended thereto. The PCR solution (50 µl) used comprised 0.07 µg of plasmid MBC1H04 as a template DNA, 50 pmoles of MBC1-a and 50 pmoles of MBC1-S1 as primers, 2.5U of TaKaRa Ex Taq and 0.25 mM dNTP in the buffer, over which 50 µl of mineral oil was layered. Thirty cycles of the PCR reaction was conducted using a temperature cycle of 94° C. for 1 min.; 55° C. for 1 min.; 72° C. for 2 min. The DNA fragments thus amplified by the PCR reaction were separated by agarose gel electrophoresis using 3% Nu Sieve GTG Agarose (FMC Bio. Products).

Then, an agarose gel fragment containing a DNA fragment of 437 bp in length was excised and the DNA fragment was purified therefrom using GENECLEAN II Kit (BIO101) in accordance with an instruction included in the kit. The purified DNA was collected by ethanol precipitation, and then dissolved in 20 µl of a solution comprising 10 mM Tris-HCl (pH 7.4) and 1 mM EDTA. One µl of the resultant DNA solution was digested with restriction enzymes BamHI and HindIII (Takara Shuzo) at 37° C. for 1 hour. The digestion mixture was extracted with phenol and chloroform and then precipitated with ethanol to collect a DNA.

The obtained HindIII-BamHI DNA fragment, which contains a DNA cording for the mouse H chain V region, was subcloned into pUC19 vector which had been digested with HindIII and BamHI. The resultant plasmid was sequenced by DNA Sequencer 373A (Perkin-Elmer) using M13 Primer M4 and M13 Primer RV as primers, and Dye Terminator Cycle Sequencing Kit (Perkin-Elmer). The plasmid contained a DNA of correct base sequence coding for the mouse H chain V region derived from hybridoma #23-57-137-1 and had a HindIII-recognition sequence and a Kozak sequence on its 5'-end region and a BamHI-recognition sequence on its 3'-end region was designated "MBC1H/pUC19".

(ii) Construction of H Chain V Region to be Used for the Preparation of cDNA-Type of Mouse-Human Chimeric H Chain The DNA coding for the mouse H chain V region constructed in the above step was modified by a PCR method to ligate it to a cDNA for the human H chain C region Cγ1. The backward primer, MBC1HVS2, (SEQ ID NO: 9) used for the modification of H chain V region was designed so as to replace the second amino acid (i.e., asparagine) of the sequence coding for the front portion of the leader sequence of the V region with glycine and to have a Kozak consensus sequence (Kozak, M. et al., J. Mol. Biol., 196, 947–950, 1987) and the HindIII- and EcoRI-recognition sequences. The forward primer MBC1HVR2 (SEQ ID NO: 10) used for the modification of H chain V region was designed so as to be hybridizable to the DNA sequence coding for the 3'-end region of the J region, to coding for the 5'-end region of the C region and to have ApaI- and SmaI-recognition sequences.

The PCR reaction was conducted using TaKaRa Ex Taq (Takara Shuzo) and a buffer appended thereto. The PCR solution (50 µl) used comprised 0.6 µg of plasmid MBC1H/pUC19 as a template DNA, 50 pmoles of MBC1HVS2 and 50 pmoles of MBC1HVR2 as primers, 2.5U of TaKaRa Ex Taq and 0.25 mM of dNTP in the buffer, over which 50 µl of mineral oil was layered. Thirty cycles of the PCR reaction was conducted using a temperature cycle of 94° C. for 1 min.; 55° C. for 1 min.; 72° C. for 1 min. The DNA fragments amplified by the PCR reaction were separated by agarose gel electrophoresis using 1% Sea Kem GTG Agarose (FMC Bio. Products) Then, an agarose gel fragment containing a DNA fragment of 456 bp in length was excised and the DNA fragment was purified therefrom using GENECLEAN II Kit (BIO101) in accordance with the procedure by the manufacturer. The purified DNA fragments were precipitated with ethanol and then dissolved in 20 µl of a solution comprising 10 mM Tris-HCl (pH 7.4) and 1 mM EDTA.

One µl of the resultant DNA solution was digested with restriction enzymes EcoRI and SmaI (Takara Shuzo) at 37° C. for 1 hour. The digestion mixture solution was extracted with phenol and chloroform and then precipitated with ethanol to collect the DNA. The obtained EcoRI-SmaI DNA fragments, which contains a DNA coding for the mouse H chain V region, was subcloned into pUC19 vector which had been prepared by digesting the plasmid with EcoRI and SmaI. The resultant plasmid was sequenced by DNA Sequencer 373A (Perkin-Elmer) using M13 Primer M4 and M13 Primer RV as primers, and Dye Terminator Cycle Sequencing Kit (Perkin-Elmer). The plasmid which contained a DNA of correct base sequence coding for the mouse H chain V region derived from hybridoma #23-57-137-1 and had a HindIII-recognition sequence and a Kozak sequence on its 5'-end region and ApaI- and SmaI-recognition sequences on its 3'-end region was designated "MBC1Hv/pUC19".

(iii) Construction of Expression Vector for Chimeric Antibody H Chain cDNA containing human antibody H chain C region Cyl was prepared as follows.

mRNA was prepared from a CHO cell into which both an expression vector DHFR-ΔE-RVh-PM-1-f (see WO92/19759) coding for the genomic DNAs of the humanized PM1 antibody H chain V region and the human antibody H chain C region IgG1 and an expression vector RV1-PM1a (see WO92/19759) coding for the genomic DNAs of the humanized PM1 antibody L chain V region and the human antibody L chain κ chain C region had been introduced. Using the mRNA obtained, was cloned a cDNA containing the humanized PM1 antibody H chain V region and the human antibody C region Cγ1 by a RT-PCR method, and then subcloned into plasmid pUC19 on the HindIII-BamHI site. The plasmid subcloned was determined for its DNA sequence and the plasmid which had a correct base sequence was designated "pRVh-PM1f-cDNA".

Expression vector DHFR-ΔE-RVh-PM-1-f which had deletions of in the HindIII site between SV40 promoter and DHFR gene and the EcoRI site between EF-1α promoter and the humanized PM1 antibody H chain V region was prepared for the construction of an expression vector for cDNA containing the humanized PM1 antibody H chain V region and the human antibody C region Cyl.

The plasmid pRVh-PM1f-cDNA obtained was digested with BamHI, blunt-ended with Klenow fragment, and further digested with Hind-III, to thereby obtain a blunt-ended HindIII-BamHI fragment. This blunt-ended HindIII-BamHI fragment was ligated to the above-mentioned HindIII site- and EcoRI site-deleted expression vector DHFR-ΔE-RVh-PM1-f which had been digested with HindIII and BamHI to construct expression vector RVh-PM1f-cDNA containing cDNAs coding for the humanized PM1 antibody H chain V region and the human antibody C region Cγ1, respectively.

The expression vector RVh-PM1f-cDNA containing cDNAs coding for the humanized PM1 antibody H chain V region and the human antibody C region Cγ1 was digested with ApaI and BamHI, and the DNA fragment containing the H chain C region was collected therefrom. The resultant DNA fragment was introduced into the above-mentioned plasmid MBC1Hv/pUC19 which had been digested with ApaI and BamHI. The plasmid thus prepared was designated "MBC1HcDNA/pUC19". This plasmid is a plasmid contained cDNAs coding for the mouse antibody H chain V region and the human antibody C region Cyl, respectively, and having EcoRI- and HindIII-recognition sequences on its 5'-end and a BamHI-recognition sequence on its 3'-end.

The plasmid MBC1HcDNA/pUC19 was digested with EcoRI and BamHI to obtain a DNA coding for the chimeric antibody H chain. The resultant DNA fragment was introduced into expression vector pCOS1 which had been digested with EcoRI and BamHI. The expression vector for the chimeric antibody thus obtained was designated "MBC1HcDNA/pCOS1". Here, the expression vector pCOS1 was constructed using HEF-PMh-gγ1 (see WO92/19759) by deleting therefrom the antibody gene by means of the digestion with EcoRI and SmaI, and then ligating it to EcoRI-NotI-BamHI Adaptor (Takara Shuzo).

For preparing a plasmid for the expression in a CHO cell, the plasmid MBC1HcDNA/pUC19 was digested with EcoRI and BamHI to obtain a DNA coding for the chimeric antibody H chain, which was then introduced into expression plasmid pCHO1 which had been digested with EcoRI and BamHI. The expression plasmid for the chimeric antibody thus obtained was designated "MBC1HcDNA/pCHO1". Here, the expression vector pCHO1 was constructed using DHFR-ΔE-rvH-PM1-f (see WO92/19759) by deleting therefrom the antibody gene by means of the digestion with EcoRI and SmaI, and then ligating it to EcoRI-NotI-BamHI Adaptor (Takara Shuzo).

(2) Construction of Human L Chain C Region (i) Preparation of Cloning Vector

To construct pUC19 vector containing the human L chain C region, a HindIII site-deleted pUC19 vector was prepared. Two μg of pUC19 vector was digested in 20 μl of a reaction solution comprising 20 mM Tris-HCl (pH 8.5), 10 mM MgCl$_2$, 1 mM DTT, 100 mM KCl, 8 U of HindIII (Takara Shuzo) at 37° C. for 1 hour. The resultant digestion mixture solution was extracted with phenol and chloroform and then was subjected to ethanol precipitation to collect the DNA of interest.

The DNA thus collected was reacted in 50 μl of a reaction solution comprising 50 μM Tris-HCl (pH 7.5), 10 mM MgCl$_2$, 1 mM DTT, 100 mM NaCl, 0.5 mM dNTP and 6U of Klenow fragment (GIBCO BRL) at room temperature for 20 min. to thereby render the ends of the DNA blunt. This reaction mixture was extracted with phenol and chloroform and then subjected to ethanol precipitation to collect the vector DNA.

The vector DNA thus collected was reacted in 10 μl of a reaction solution comprising 50 mM Tris-HCl (pH 7.6), 10 mM MgCl$_2$, 1 mM ATP, 1 mM DTT, 5% (v/v) polyethylene glycol-8000 and 0.5 U of T4 DNA ligase (GIBCO BRL) at 16° C. for 2 hours to cause self-legation of the vector DNA. 5 μl of the reaction solution was added to 100 μl of a solution containing competent cells of *E. coli* strain JM109 (Nippon Gene) and the resultant solution was allowed to stand on ice for 30 min., at 42° C. for 1 min. and further on ice for 1 min. 500 ml of SOC culture medium was added to the reaction solution, and then incubated at 37° C. for 1 hour. The resultant solution was plated on a 2×YT agar medium (containing 50 μg/ml of ampicillin) which had been applied with X-gal and IPTG on its surface (Molecular Cloning: A Laboratory Manual, Sambrook, et al., Cold Spring Harbor Laboratory Press, 1989), and then cultured at 37° C. overnight, thereby obtaining a transformant.

The transformant was cultured on a 2×YT medium containing 50 μg/ml of ampicillin at 37° C. overnight. From the cell fraction of the culture medium, was purified a plasmid DNA using Plasmid Mini Kit (QIAGEN) in accordance with an instruction included in the kit. The purified plasmid was digested with HindIII. The plasmid which was confirmed to have a HindIII site-deletion was designated "pUC19 ΔHindIII".

(ii) Construction of DNA Coding for Human L Chain λ Chain C Region

The human antibody L chain λ chain C region has been known to have at least four isotypes including Mcg$^+$Ke$^+$Oz$^-$, Mcg$^-$Ke$^+$Oz$^-$, Mcg$^+$Ke$^+$Oz$^+$ and Mcg$^+$Ke$^+$Oz$^+$ (P. Dariavach, et al., Proc. Natl. Acad. Sci. USA, 84, 9074–9078, 1987). The search was made for a human antibody L chain λchain C region homologous to the #23-57-137-1 mouse L chain λ chain C region based on the EMBL data base. As a result, it was found that the isotype Mcg$^+$Ke$^+$Oz$^-$ (Accession No. X57819) (P. Dariavach, et al., Proc. Natl. Acad. Sci. USA, 84, 9074–9078, 1987) of the human antibody L chain λ chain λ chain exhibited the highest homology with the #23-57-137-1 mouse L chain λ chain C region and showed 64.4% homology in terms of amino acid sequence and 73.4% homology in terms of DNA sequence.

Then, the construction of the DNA coding for the human antibody L chain λ chain C region was conducted by a PCR method. Each of the following primers used was synthesized using 394 DNA/RNA Synthesizer (ABI). The primers synthesized were HLAMB1 (SEQ ID NO: 11) and HLAMB3 (SEQ ID NO: 13) both having a sense DNA sequence and HLAMB2 (SEQ ID NO: 12) and HLAMB4 (SEQ ID NO: 14) both having an antisense DNA sequence, each primer containing a complementary sequence of 20–23 bp in length on the both ends.

External primers HLAMBS (SEQ ID NO: 15) and HLAMBR (SEQ ID NO: 16) have a sequence complementary to the primers HLAMB1 and HLAMB4, respectively, and contain the EcoRI-, HindIII- and B1nI-recognition sequences and the EcoRI-recognition sequence, respectively. In the first PCR reaction, the HLAMB1-HLAMB2 and HLAMB3-HLAMB4 reactions were conducted. After the reactions were completed, both of the resultants were mixed with each other in equivalent quantities, and then assembled in the second PCR reaction. To the resultant reactant, were added the external primers HLAMBS and HLAMBR. This reaction mixture was subjected to the third PCR reaction for amplifying the full length DNA.

The PCR reactions were conducted using TaKaRa Ex Taq (Takara Shuzo) in accordance with the procedure by the manufacturer. In the first PCR reaction, was used 100 μl of either a reaction solution comprising 5 pmoles of HLAMB1, 0.5 pmole of HLAMB2 and 5U of TaKaRa Ex Taq (Takara Shuzo) or a reaction solution comprising 0.5 pmole of HLAMB3, 5 pmoles of HLAMB4 and 5U of TaKaRa Ex Taq (Takara Shuzo), over which 50 μl of mineral oil was layered, and five cycles of the PCR reaction was conducted using a temperature cycle program of 94° C. for 1 min., 60° C. for 1 min. and 72° C. for 1 min. In the second PCR reaction, was used a mixture of 50 μl of each of the reaction solutions, over which 50 μl of mineral oil was layered, and three cycles of the PCR reaction was conducted using a temperature cycle program of 94° C. for 1 min., 60° C. for 1 min. and 72° C. for 1 min. In the third PCR reaction, the reaction solution to which 50 pmoles of each of the external primers HLAMBS and HLAMBR were added was used, and thirty cycles of the PCR reaction was conducted using a temperature cycle program of 94° C. for 1 min., 60° C. for 1 min. and 72° C. for 1 min.

The DNA fragment obtained by the third PCR reaction was subjected to electrophoresis using 3% low melting agarose gel (NuSieve GTG Agarose, FMC), and collected and purified from the gel using GENECLEAN II Kit (BIO101) in accordance with the procedure included in the kit.

The DNA fragment thus obtained was digested in 20 μl of a reaction solution comprising 50 mM Tris-HCl (pH 7.5), 10 mM MgCl$_2$, 1 mM DTT, 100 mM NaCl and 8U of EcoRI (Takara Shuzo) at 37° C. for 1 hour. The digestion solution was extracted with phenol and chloroform and then precipitated with ethanol to thereby obtain the DNA. The DNA was collected and dissolved in 8 µl of a solution comprising 10 mM Tris-HCl (pH 7.4) and 1 mM EDTA.

0.8 µg of the plasmid pUC19 ΔHindIII was digested with EcoRI in the same manner as mentioned above. The digestion solution was extracted with phenol and chloroform, followed by ethanol precipitation, obtaining a digested plasmid pUC19 ΔHindIII. The digested plasmid thus obtained was reacted in 50 µl of a reaction solution comprising 50 mM Tris-HCl (pH 9.0), 1 mM MgCl$_2$ and alkaline phosphatase (E. coli C75; Takara Shuzo) at 37° C. for 30 min. to dephosphorylate the plasmid (i.e., BAP-treatment). The reaction solution was subjected to phenol and chloroform extraction and ethanol precipitation to obtain the DNA. The DNA thus obtained was dissolved in 10 µl of a solution comprising 10 mM Tris-HCl (pH 7.4) and 1 mM EDTA.

One µl of the BAP-treated plasmid pUC19 ΔHindIII thus prepared was mixed with 4 µl of the DNA obtained by the above-mentioned PCR reaction to ligate to each other using DNA Ligation Kit Ver.2 (Takara Shuzo). The resultant plasmid was introduced into a competent cell of E. coli, JM109, to form a transformant. The transformant was cultured overnight in 2 ml of a 2×YT medium containing 50 µg/ml of ampicillin. From the cell, the plasmid was purified using QIAprep Spin Plasmid Kit (QIAGEN).

With respect to the plasmid described above, the cloned DNA was confirmed on its sequence. For determination the DNA sequence, 373A DNA Sequencer (ABI) and primers "M13 Primer M4" and "M13 Primer RV" (Takara Shuzo) were used. As a result, it was found that the cloned DNA had a deleted portion of 12 bp in length therein. The plasmid containing the DNA was designated "cλΔ/pUC19". Then, for making up for the portion, primers, HCLMS (SEQ ID NO: 17) and HCLMR (SEQ ID NO: 18), were newly synthesized and a correct DNA was reconstructed by a PCR method.

The first PCR reaction was conducted, using the plasmid cλΔ/pUC19 containing the deleted DNA as a template, and the primers HLAMBS and HCLMS or primers HCLMS and HLAMB4. Each of the PCR reaction products was purified respectively. In the second PCR reaction, the PCR products were assembled with each. To the resultant, were added external primers HLAMBS and HLAMB4, followed by the third PCR reaction for amplifying the full length DNA.

In the first PCR reaction, 100 µl of a reaction solutions comprising 0.1 µg CλΔ/pUC19 as a template, either 50 pmoles of each of the primers HLAMBS and HCLMR or 50 pmoles of each of the primers HCLMS and HLAMB4, and 5 U of TaKaRa Ex Taq (Takara Shuzo) was used, over which 50 µl of mineral oil was layered, and thirty cycles of the PCR reaction was conducted using a temperature cycle of 94° C. for 1 min., 60° C. for 1 min. and 72° C. R1 for 1 min.

The PCR products, HLAMBS-HCLMR (236 bp) and HCLMS-HLAMB4 (147 bp) were subjected to electrophoresis using 3% low melting agarose gel to isolate the DNA fragment. The DNA fragment was then collected and purified from the gel using GENECLEAN II Kit (BIO101). In the second PCR reaction, 20 µl of a reaction solution comprising 40 ng of the purified DNA fragments and 1U of TaKaRa Ex Taq (Takara Shuzo) were used, over which 25 µl of mineral oil was layered, and five cycles of a temperature cycle of 94° C. for 1 min., 60° C. for 1 min. and 72° C. for 1 min. was executed.

In the third PCR reaction, 100 µl of a reaction solution comprising 2 µl of the reaction solution obtained by the second PCR reaction, 50 pmoles of each of external primers HLAMBS and HLAMB4 and 5U of TaKaRa Ex Taq (Takara Shuzo) were used, over which 50 µl of mineral oil was layered, and thirty cycles of the PCR reaction was conducted using a temperature cycle of 94° C. for 1 min., 60° C. for 1 min. and 72° C. for 1 min., thereby obtaining a DNA fragment of 357 bp in length (third PCR product). The DNA fragment was subjected to electrophoresis using 3% low melting agarose gel to isolate the DNA fragment. The resultant DNA fragment was collected and purified using GENECLEAN Kit (BIO101).

An amount of 0.1 µg of the DNA fragment thus obtained was digested with EcoRI, and then subcloned into a plasmid pUC19 ΔHindIII which had been treated with BAP. The resultant plasmid was introduced into a competent cell of E. coli, JM109, to form a transformant. The transformant thus prepared was cultured overnight in 2 ml of a 2×YT medium containing 50 µg/ml of ampicillin. From the cell fraction, the plasmid was purified using QIAprep Spin Plasmid Kit (QIAGEN).

The DNA sequence of the plasmid thus obtained was confirmed by using M13 Primer M4 and M13 Primer RV (Takara Shuzo) and determined 373A DNA Sequencer (ABI). The plasmid confirmed to have the correct DNA sequence without any deletion was designated "Cλ/pUC19".

(iii) Construction of DNA Coding for Human L Chain, K Chain C Region

A DNA fragment coding for the L chain K chain C region was cloned from plasmid HEF-PM1k-gk (WO92/19759) by a PCR method. The forward primer HKAPS (SEQ ID NO: 19) was designed so as to contain the EcoRI- and HindIII and B1nI-recognition sequences and the backward primer HKAPA (SEQ ID NO: 20) was designed so as to contain the EcoRI-recognition sequence, and both of them were synthesized using 394 DNA/RNA Synthesizer (ABI).

A PCR reaction was conducted using 100 µl of a reaction solution comprising 0.1 µg of plasmid HEF-PM1k-gk as a template, 50 pmoles of each of primers HKAPS and HKAPA and 5U of TaKaRa Ex Taq (Takara Shuzo), over which 50 µl of mineral oil was layered. Thirty cycles of the PCR reaction was conducted using a temperature cycle of 94° C. for 1 min., 60° C. for 1 min. and 72° C. for 1 min., thereby obtaining a DNA fragment of 360 bp in length. The DNA fragment was isolated by electrophoresis using 3% low melting agarose, and then collected and purified using GENECLEAN II Kit (BIO101).

The DNA fragment thus obtained was digested with EcoRI and then cloned into plasmid pUC19 ΔHindIII which had been treated with BAP. The resultant plasmid was introduced into a competent cell of E. coli, JM109, to obtain a transformant. The transformant thus obtained was cultured overnight in 2 ml of 2×YT medium containing 50 µg/ml of ampicillin. From the cell fraction, the plasmid was purified using QIAprep Spin Plasmid Kit (QIAGEN).

The purified plasmid DNA was sequenced using M13 Primer M4 and M13 Primer RV (Takara Shuzo) by means of 373A DNA Sequencer (ABI). The plasmid which was confirmed to have a correct base sequence was designated "Cκ/pUC19".

(3) Construction of Chimeric Antibody L Chain Expression Vector

Chimeric #23-57-137-1 antibody L chain expression vector was constructed. The DNA coding for #23-57-137-1 L chain V region was ligated to the HindIII and B1nI sites, present just front of the human antibody C region, of each of the plasmid Cλ/pUC19 and Cκ/pUC19, thereby obtaining pUC19 vectors each containing DNA coding for the chimeric #23-57-137-1 antibody L chain V region and L chain λ or κ chain C region. Each of the resultant vectors was then digested with EcoRI to excise the DNA coding for the chimeric antibody L chain and the DNA was subcloned into HEF expression vector.

The DNA coding for #23-57-137-1 antibody L chain V region was cloned from plasmid MBC1L24 by a PCR method. The primers were individually synthesized using 394 DNA/RNA Synthesizer (ABI). The backward primer MBCCHL1 used (SEQ ID NO: 21) was designed to contain a HindIII-recognition sequence and a Kozak sequence (Kozak, M. et al., J. Mol. Biol. 196, 947–950, 1987) and the forward primer MBCCHL3 (SEQ ID NO: 22) was designed to contain BglII- and RcoRI-recognition sequences.

The PCR reaction was conducted using 100 μl of a reaction solution comprising 10 mM Tris-HCl (pH 8.3), 50 mM KC1, 1.5 mM $MgCl_2$, 0.2 mM dNTP, 0.1 μg MBC1L24, 50 pmoles of each of primers MBCCHL1 and MBCCHL3 as primers and 1 μl of AmpliTaq (PERKIN ELMER), over which 50 μl of mineral oil was layered. Thirty cycles of the PCR reaction was conducted using a temperature cycle of 94° C. for 45 sec., 60° C. for 45 sec. and 72° C. for 2 min.

The DNA fragment of 444 bp was electrophoresed using 3% low melting agarose gel, and collected and purified using GENECLEAN Kit (BIO101). The purified DNA fragment was dissolved in 20 μl of a solution containing 10 mM Tris-HCl (pH 7.4) and 1 mM EDTA. One μl of the PCR product was digested in 20 μl of a reaction solution comprising 10 mM Tris-HCl (pH 7.5), 10 mM $MgCl_2$, 1 mM DTT, 50 mM NaCl, 8U of HindIII (Takara Shuzo) and 8U of EcoRI (Takara Shuzo) at 37° C. for 1 hour. The digestion solution was extracted with phenol and chloroform, followed by ethanol precipitation to collect the DNA as precipitates. The DNA thus obtained was dissolved in 8 μl of a solution comprising 10 mM Tris-HCl (pH 7.4) and 1 mM EDTA.

One μg of plasmid pUC19 was digested with HindIII and EcoRI in the same manner as mentioned above, and then extracted with phenol and chloroform, followed by ethanol precipitation to collect the digested plasmid. The resultant was treated with BAP [i.e., an alkaline phosphatase (E. coli C75; Takara Shuzo)]and then extracted with phenol and chloroform, followed by ethanol precipitation, thereby obtain the DNA. The resultant DNA was dissolved in 10 μl of a solution comprising 10 mM Tris-HCl (pH 7.4) and 1 mM EDTA.

One μl of the BAP treated plasmid pUC19 was mixed with 4 μl of the above-mentioned PCR product to ligate each other using DNA Ligation Kit Ver. 2 (Takara Shuzo). The resultant plasmid was introduced into a competent cell of E. coli, JM109 (Nippon Gene), in the same manner as described above to form a transformant. The transformant was inoculated overnight on a 2×YT agar medium containing 50 μg/ml of ampicillin at 37° C. The resultant transformant was then cultured overnight in 2 ml of a 2×YT medium containing 50 μg/ml of ampicillin at 37° C. From the cell fraction, the plasmid was purified using QIAprep Spin Plasmid Kit (QIAGEN). After determining the DNA sequence, the plasmid confirming to have a correct DNA sequence was designated "CHL/pUC19".

One μg of each of plasmids Cλ/pUC19 and Cλ/pUC19 was respectively digested in 20 μl of a reaction solution comprising 20 mM Tris-HCl (pH 8.5), 10 mM $MgCl_2$, 1 mM DTT, 100 mM KC1, 8 U of HindIII (Takara Shuzo) and 2U of B1nI (Takara Shuzo) at 37° C. for 1 hour. The digestion solution was extracted with phenol and chloroform, followed by ethanol precipitation, thereby obtaining a DNA.

The DNA was treated with BAP at 37° C. for 30 min. and then extracted with phenol and chloroform, followed by ethanol precipitation. The resultant was dissolved in 10 μl of a solution comprising 10 mM Tris-HCl (pH 7.4) and 1 mM EDTA.

Eight μg of the plasmid CHL/pUC19 which contained a DNA coding for #23-57-137-1 L chain V region was digested with HindIII and B1nI in the same manner as mentioned above. The DNA fragment of 409 bp in length thus obtained was electrophoresed using 3% low melting agarose gel and then collected and purified using GENECLEAN II Kit (BIO101) from the gel. The DNA fragment was dissolved in 10 μl of a solution comprising 10 mM Tris-HCl (pH 7.4) and 1 mM EDTA.

Four μl of the L chain V region DNA was subcloned into 1 μl of each of the BAP-treated plasmids Cλ/pUC19 or Cκ/pUC19, and then introduced into a competent cell of E. coli, JM109, to format a transformant. The transformant was cultured overnight in 3 ml of a 2×YT medium containing 50 μg/ml of ampicillin. From the cell fraction, the plasmid was isolated and purified using QIAprep Spin Plasmid Kit (QIAGEN). The plasmids thus prepared were designated "MBC1L(λ)/pUC19" and "MBC1L(κ)/pUC19", respectively.

Each of plasmids MBC1L(λ)/pUC19 and MBC1L(κ)/pUC19 was digested with EcoRI and then subjected to electrophoresis using 3% low melting agarose gel. A DNA fragment of 743 bp in length was isolated and purified from the gel using GENECLEANII Kit (BIO101) and dissolved in 10 μl of a solution comprising 10 mM Tris-HCl (pH 7.4) and 1 mM EDTA.

An amount of 2.7 μg of expression vector, plasmid HEF-PM1k-gk, was digested with EcoRI and then extracted with phenol and chloroform, followed by ethanol precipitation, thereby obtaining a DNA fragment. The DNA fragment was treated with BAP, and then subjected to electrophoresis using 1% low melting agarose gel. From the gel, a DNA fragment of 6561 bp in length was isolated and purified therefrom using GENECLEANII Kit (BIO101). The DNA fragment was dissolved in 10 μl of a solution comprising 10 mM Tris-HCl (pH 7.4) and 1 mM EDTA.

The HEF vector thus prepared was treated with BAP, and 2 μl of the BAP-treated HEF vector was mixed with 3 μl of the EcoRI fragments of plasmids MBC1L(λ)/pUC19 or MBC1L(κ)/pUC19, to ligate to each other. The ligation product was introduced into a competent cell of E. coli, JM109, to form a transformant. The transformant was cultured in 2 ml of a 2×YT medium containing 50 μg/ml of ampicillin. From the cell fraction, the plasmid was purified using QIAprep Spin Plasmid Kit (QIAGEN).

The plasmid DNA thus purified was digested in 20 μl of a reaction solution comprising 20 mM Tris-HCl (pH 8.5), 10 mM $MgCl_2$, 1 mM DTT, 100 mM KCl, 8 U of HindIII (Takara Shuzo) and 2 U of PvuI (Takara Shuzo) at 37° C. for 1 hour. In this digestion reaction, it was assumed that if the above-mentioned DNA fragment was inserted into the vector in the correct orientation, a digestion fragment of 5104/2195 bp would be obtained, whereas if the above-mentioned DNA fragment was inserted into the vector in the reverse orientation, a digestion fragment of 4387/2926 bp would be obtained. Based on this assumption, the plasmids in which the fragment was inserted in a correct orientation were designated "MBC1L(λ)/neo" and "MBC1L(κ)/neo", respectively.

(4) Transfection of COS-7 Cells

The expression plasmids prepared above were each expressed transiently using COS-7 cells in order to evaluate the chimeric antibody on its binding with and neutralizing activities against antigen.

The transient expression of the chimeric antibody was conducted using a combination of either plasmids MBC1HcDNA/pCOS1 and MBC1L (λ)/neo or plasmids MBC1HcDNA/pCOS1 and MBC1L(κ)/neo by means of electroporation using Gene Pulser (Bio Rad) to co-transfect each of these plasmid DNA combinations into COS-7 cells. That is, into 0.8 ml of a cell suspension in which COS-7 cells were suspended in PBS(−) in a concentration of $1 \times 10^7$ cells/ml, 10 μg of each of the plasmid DNAs was added. The resultant solution was applied with pulses at an electrostatic capacity of 1,500V and 2 μF to cause electroporation. After 10 min. of recovery period at room temperature, the cells were suspended in a DMEM medium containing. 2% Ultra Low IgG fetal calf serum (GIBCO) and then cultured using a 10 cm culture dish in a $CO_2$ incubator. After culturing for 72 hours, a culture supernatant was collected and centrifuged to remove cell debris and was provided as a sample for the ELISA assay.

In this procedure, the purification of the chimeric antibodies from the culture supernatant of COS-7 cells was conducted using AffiGel Protein A MAPSII Kit (Bio Rad) in accordance with an instruction included in kit.

(5) ELISA Assay (i) Determination of Antibody Concentration

An ELISA plate for determining antibody concentration was prepared as follows. Each of the wells of a 96-well plate for ELISA (Maxisorp, NUNC) was coated with 100 μl of a solution comprising goat anti-human IgG antibody (TAGO) prepared in a coating buffer (0.1 M $NaHCO_3$, 0.02% $NaN_3$) of a concentration of 1 μg/ml and then blocked with 200 μl of a dilution buffer (50 mM Tris-HCl, 1 mM $MgCl_2$, 0.1 M NaCl, 0.05% Tween20, 0.02% $NaN_3$, 1% bovine serum albumin (BSA); pH 7.2). Into each well was added, a culture supernatant of the COS-7 cells in which the chimeric antibodies had been expressed or the purified chimeric antibodies at stepwise dilution. After incubating at room temperature for 1 hour and washing with PBS-Tween20, each well was added with 100 μl a solution of alkaline phosphatase-conjugated goat anti-human IgG antibodies (TAGO). After incubating at room temperature for 1 hour and washing with PBS-Tween20, each well was added with 1 mg/ml of a substrate solution ("Sigma104", p-nitrophenylphosphoric acid, SIGMA). The solution was measured for absorbance at 405 nm using Microplate Reader (Bio Rad). As a standard for this determination, Hu IgG1λ Purified (The Binding Site) was used.

(ii) Determination of antigen binding ability An ELISA plate for the determination of antigen binding ability was prepared as follows. Each of the wells of a 96-well plate for ELISA was coated with 100 μl of a solution comprising human PTHrP (1–34) (Peptide Research Institute) prepared in a coating buffer of a concentration of 1 μg/ml and then blocked with 200 μl of a dilution buffer. Into each well was added, the culture supernatant of the COS-7 cells in which the chimeric antibodies had been expressed or the purified chimeric antibodies at stepwise dilution. After incubating at room temperature and washing with PBS-Tween20, each well was added with 100 μl of a solution of alkaline phosphatase-conjugated goat anti-human IgG antibodies (TAGO). After incubating at room temperature and washing with PBS-Tween20, each well was added with 1 mg/ml of a substrate solution ("Sigma104", p-nitrophenylphosphoric acid, SIGMA). The solution was measured for absorbance at 405 nm using Microplate Reader (Bio Rad).

Figure 4:
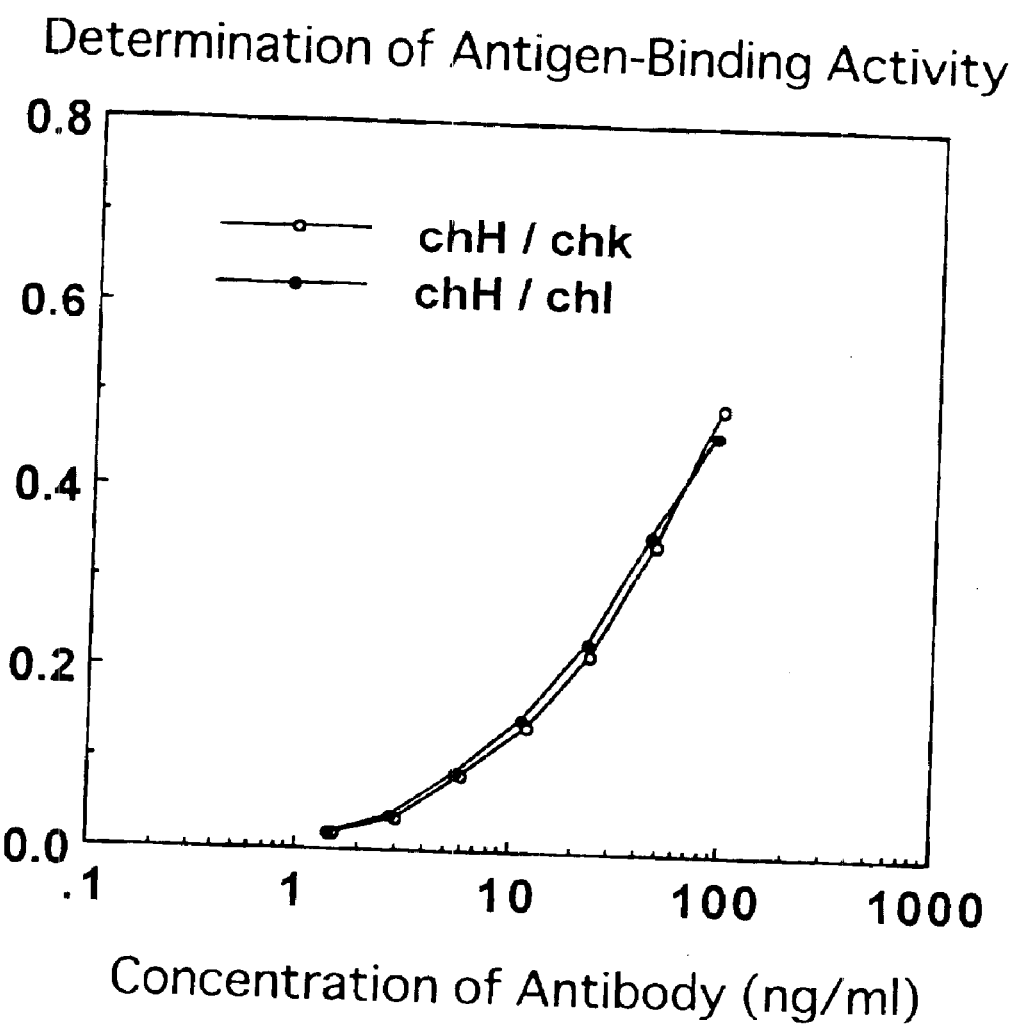
FIG. 4 is a graph showing the measurement result of the antigen-binding activity of the antibodies.

As a result, it was found that the chimeric antibody had a binding ability against human PTHrP (1–34) and also had a correct structure of the cloned mouse antibody V region (FIG. 4). It was also found that there was no difference in the binding ability against PTHrP (1–34) between the chimeric antibody in which the L chain C region has λ chain and those in which the L chain C region has κ chain. Therefore, the L chain C region of the humanized antibody was constructed using the humanized antibody L chain λ chain.

(6) Establishment of CHO Stable Transformed Cell Line

For establishing a stable transformant for the chimeric antibody, the above-mentioned expression plasmid was introduced into a CHO cell (DXB11).

Establishment of a stable transformant for the chimeric antibody was conducted using combinations of expression plasmids for CHO cell, MBC1HcDNA/pCHO1 and MBC1L (λ)/neo or expression plasmids for CHO cell, MBC1HcDNA/pCHO1 and MBC1L (κ)/neo. These combinations of plasmids were individually co-transfected into CHO cells by electroporation using Gene Pulser (Bio Rad). Each of the expression vectors was cleaved with restriction enzyme PvuI to obtain a lenear DNA. The resultant DNA was collected by extraction with phenol and chloroform and subsequent precipitation with ethanol. The plasmid DNAs thus prepared were respectively subjected to electroporation. Ten μg of each of the plasmid DNAs was added to 0.8 ml of a cell suspension containing CHO cells in PBS(−) in a concentration of $\times 10^7$ cells/ml. The resultant mixture was applied with pulses at an electrostatic capacity of 1,500V and 25 μF. After 10 min. of recovery period at room temperature, the electroporated cells were suspended in a MEM-α medium (GIBCO) supplemented with 10% fetal calf serum (GIBCO). The resultant suspension was cultured using three 96-well plates (Falcon) in a $CO_2$ incubator. On the day after starting the cultivation, the medium was replaced by a selective medium [a MEM-α medium supplemented with 10% fetal calf serum (GIBCO) and 500 mg/ml of GENETICIN (G418Sulfate; GIBCO) without ribonucleoside or deoxyribonucleoside]. From the culture medium, cells into which the antibody gene was introduced were selected. After replacing the selective medium by a fresh one, before and after two weeks of cultivation, the cells were observed under a microscope. When a cell growth was observed, the cells were determined for the amount of antibodies produced by the above-mentioned ELISA assay. Among the cells, those which produced a larger amount of antibodies were selectively collected.

The scale up of the culture of the stable transformant for the established antibodies was conducted in a roller bottle using a MEM medium supplemented with 2% Ultra Low IgG fetal calf serum without ribonucleoside or deoxyribonucleoside. On day 3 and day 4 of the cultivation, the culture supernatant was collected and then filtered using a filter having a pore size of 0.2 μm (Millipore) to remove cell debris therefrom.

Subsequently, the purification of the chimeric antibodies from the culture supernatant of the CHO cells was conducted using POROS Protein A Column (PerSeptive Biosystems) on ConSep LC100 (Millipore) in accordance with an instruction included within. The purified chimeric antibodies were provided as samples for the determination of neutralizing activity and for the examination of efficacy on hypercalcemic model animals. The concentration and the binding activity of the purified chimeric antibodies against antigen were determined by the same ELISA system.

EXAMPLE 3

Construction of Humanized Antibody (1) Construction of Humanized Antibody H Chain (i) Construction of Humanized H Chain V Region Humanized #23-57-137-1 antibody H chain was prepared by CDR-grafting technique by means of PCR method. For preparing a humanized #23-57-137-1 antibody H chain (version "a") having a FR derived from human antibody S31679 (NMRF-PDB; Cuisinier, A. M. et al., Eur. J. Immunol., 23, 110–118, 1993), the following six types of PCR primers were used: CDR-grafting primers: MBC1HGP1 (SEQ ID NO: 23) and MBC1HGP3 (SEQ ID NO: 24) (both containing a sense DNA sequence) and MBC1HGP2 (SEQ ID NO: 25) and MBC1HGP4 (SEQ ID NO: 26) (both containing an antisense DNA sequence), all of which containing a complementary sequence of 15–21 bp in length on both ends thereof; and external primers: MBC1HVS1 (SEQ ID NO: 27) and MBC1HVR1 (SEQ ID NO: 28), both having a homology with the CDR-grafting primers MBC1HGP1 and MBC1HGP4, respectively.

The CDR-grafting primers MBC1HGP1, MBC1HGP2, MBC1HGP3 and MBC1HGP4 were isolated using an urea-denatured polyacrylamide gel (Molecular Cloning: A Laboratory Manual, Sambrook, et al., Cold Spring Harbor Laboratory Press, 1989) and extracted from the gel fraction by a crush-and-soak method (Molecular Cloning: A Laboratory Manual, Sambrook, et al., Cold Spring Harbor Laboratory Press, 1989) in the following manner.

One nmole of each of the CDR-grafting primers was isolated with 6% denatured polyacrylamide gel to obtain DNA fragments. From the resultant DNA fragments, those having a desired length was identified on a silica gel thin plate by irradiation of UV ray and then collected therefrom by a crush-and-soak method. The resultant was dissolved in 20 µl of a solution comprising 10 mM Tris-HCl (pH 7.4) and 1 mM EDTA. The PCR reaction was conducted using TaKaRa Ex Taq (Takara Shuzo). The reaction solution (100 µl) used in the PCR reaction comprised 1 µl of each of the above-mentioned CDR-grafting primers MBC1HGP1, MBC1HGP2, MBC1HGP3 and MBC1HGP4, 0.25 mM dNTP and 2.5U of TaKaRa Ex Taq in the buffer. Five cycles of the PCR reaction was conducted using a temperature cycle of 94° C. for 1 min., 55° C. for 1 min. and 72° C. for 1 min. Into the resultant reaction mixture were added, both of the external primers MBC1HVS1 and MBC1HVR1 each in an amount of 50 pmoles. Using this reaction mixture, additional 30 cycles of the PCR reaction was conducted using the same temperature cycle. The DNA fragment thus amplified was isolated by agarose gel electrophoresis using 4% Nu Sieve GTG agarose (FMC Bio. Products).

An agarose fragment containing a DNA fragment of 421 bp in length was excised and the DNA fragment was purified therefrom using GENECLEANII Kit (BIO101) in accordance with an instruction included in the kit. The DNA fragment thus purified was precipitated with ethanol and then dissolved in 20 µl of a solution comprising 10 mM Tris-HCl (pH 7.4) and 1 mM EDTA. The PCR reaction mixture obtained was used for subcloning of the DNA fragment into plasmid pUC19 which had been prepared by digesting the plasmid with BamHI and HindIII; thereafter the base sequence of the resultant plasmid was determined. A plasmid having a correct sequence was designated "hMBCHv/pUC19".

(ii) Construction of H Chain V Region for Humanized H Chain cDNA

For the ligation to the cDNA of humanized H chain C region Cγ1, the DNA of the humanized H chain V region constructed in the above step was modified by a PCR method. In this method, the backward primer MBC1HVS2 used was designed so as to be hybridizable to the sequence coding for the 5'-end region of the leader sequence of the V region and to carry a Kozak consensus sequence (Kozak et al., J. Mol. Biol. 196, 947–950, 1987) and HindIII- and EcoRI-recognition sequences. The forward primer MBC1HVR2 used for the modification of the DNA for the H chain V region was designed so as to be hybridizable to both the DNA sequence coding for the 3'-end region of the J region and the DNA sequence coding for the 5'-end region of the C region and to carry ApaI- and SamI-recognition sequences.

The PCR reaction was conducted using TaKaRa Ex Taq (Takara Shuzo) and a buffer was used therewith. The reaction solution used for the PCR reaction comprised 0.4 µg of hMBCHv/pUC19 as a DNA template, 50 pmoles of each of MBC1HVS2 and MBC1HVR2 as primers, 2.5U of TaKaRa Ex Taq and 0.25 mM dNTP in the buffer. Thirty cycles of the PCR reaction was conducted using a temperature cycle of 94° C. for 1 min., 55° C. for 1 min. and 72° C. for 1 min. The DNA fragment thus amplified by the PCR method was isolated by agarose gel electrophoresis using 3% Nu Sieve GTG agarose (FMC Bio. Products).

A DNA fragment of 456 bp in length was excised and the DNA fragment was purified therefrom using GENECLEA-NII Kit (BIO101) in accordance with an instruction included within. The DNA fragment thus purified was precipitated with ethanol and then dissolved in 20 µl of a solution comprising 10 mM Tris-HCl (pH 7.4) and 1 mM EDTA. The PCR reaction mixture thus obtained was used for subcloning of the DNA fragment into plasmid pUC19 which had been prepared by digesting the plasmid with EcoRI and SmaI; thereafter the DNA sequence of the resultant plasmid was determined. The plasmid DNA thus prepared which contains a DNA coding for the mouse H chain V region derived from the hybridoma #23-57-137-1 and also contains the EcoRI- and HindIII-recognition sequences and a Kozak sequence on the 5'-end and the ApaI- and SmaI-recognition sequences on the 3'-end was designated "hMBC1 Hv/pUC19".

(2). Construction of Expression Vector for Humanized Antibody H Chain

Plasmid RVh-PM1f-cDNA containing a cDNA sequence of hPM1 antibody H chain was digested with ApaI and BamHI to obtain a DNA fragment containing a base sequence of the H chain C region. The DNA fragment was introduced into plasmid hMBC1 Hv/pUC19 which had been prepared by digesting the plasmid with ApaI and BamHI. The plasmid thus prepared was designated "hMBC1HcDNA/pUC19". This plasmid was a plasmid containing both a DNA coding for the humanized #23-57-137-1 antibody H chain V region and a DNA coding for the human H chain C region Cγ1 and to have EcoRI- and HindIII-recognition sequences on the 5'-end region and a BamHI-recognition sequence on the 3'-end region. The base sequence and the corresponding amino acid sequence of the humanized H chain version "a" contained in the plasmid hMBC1HcDNA/pUC19 are shown in SEQ ID NO: 58 and SEQ ID NO: 56, respectively.

The plasmid hMBC1HcDNA/pUC19 was digested with EcoRI and BamHI to obtain a DNA fragment containing a base sequence coding for the H chain. The DNA fragment was introduced into expression plasmid pCOS1 which had been prepared by digesting the plasmid with EcoRI and BamHI. The expression plasmid for a humanized antibody thus obtained was designated "hMBC1HcDNA/pCOS1".

To prepare a plasmid for expression in a CHO cell, plasmid hMBC1 HcDNA/pUC19 was digested with EcoRI and BamHI to obtain a DNA fragment containing a DNA coding for the H chain. The DNA fragment was introduced into expression vector pCHO1 which had been prepared by digesting the plasmid with EcoRI and BamHI. The expression plasmid for the humanized antibody thus obtained was designated "hMBC1 HcDNA/pCHO1".

(3) Construction of L Chain Hybrid Variable Region (i) Preparation of FR1, 2/FR3, 4 Hybrid Antibody A DNA coding for the L chain in which the FR regions were recombined with those from a humanized antibody and a mouse (chimeric) antibody was constructed and evaluated the regions on their suitability for humanization. In this step, a hybrid antibody comprising FR1 and FR2 both derived from a human antibody and FR3 and FR4 both derived from a mouse antibody was prepared by utilizing the AflII restriction site present in CDR 2.

Ten µg of each of plasmids MBC1L (λ)/neo and hMBC1L (λ))/neo was digested in 100 µl of a reaction solution comprising 10 mM Tris-HCl (pH 7.5), 10 mM MgCl$_2$, 1 mM DTT, 50 mM NaCl, 0.01% (w/v) of BSA and 10 U of AflII (Takara Shuzo) at 37° C. for 1 hour. The reaction solution was subjected to electrophoresis using 2% low melting agarose gel, and DNA fragments of 6282 bp in length (referred to as "c1") and 1022 bp in length (referred to as h1) were collected and purified from the gel using GENECLEA-NII Kit (BIO101).

One µg of each of the c1 and h1 fragments obtained was subjected to treatment with BAP. The DNA fragment was extracted with phenol and ethanol, collected by ethanol precipitation, dissolved in 10 µl of a solution comprising 10 mM Tris-HCl (pH 7.4) and 1 mM EDTA.

One µl of each of the BAP-treated c1 and h1 DNA fragments were mixed with 4 µl of the h2 and c2 DNA fragments, respectively, to ligate to each other (at 4° C. overnight). The ligation product was introduced into a competent cell of E. coli, JM109, to form a transformant. The transformant was cultured in 2 ml of a 2×YT medium containing 50 µg/ml of ampicillin. From the cell fraction, the plasmid was purified using QIAprep Spin Plasmid Kit (QIAGEN).

The plasmid DNA purified was digested in 20 µl of a reaction solution comprising 10 mM Tris-HCl (pH 7.5), 10 mM MgCl$_2$, 1 mM DTT, 2U of ApaLI (Takara Shuzo), and 8U of BamHI (Takara Shuzo) or HindIII (Takara Shuzo) at 37° C. for 1 hour. In this step, the plasmid was identified based on the expectation that if the c1-h2 fragment was correctly ligated in the plasmid, this ligation would give an ApaLI-digestion fragment of 5560/1246/498 bp or a BamHI/HindIII-digestion fragment of 7134/269 bp.

The expression vector coding for the human FR1, 2/mouse FR3, 4 hybrid antibody L chain was designated "h/mMBC1L(λ)/neo". On the other hand, a clone for the h1-c1 could not be obtained. Therefore, recombination on a pUC vector was conducted, followed by cloning to a HEF vector. Here, used as templates were plasmid hMBC1 Laλ/pUC19, which contained a DNA coding for a humanized antibody L chain V region having no amino acid replacements and plasmid hMBC1 Ldλ/pUC19, which contained a DNA coding for a humanized antibody L chain V region having an amino acid replacement at the 91-position amino acid in FR3 (i.e., amino acid number 87 according to the definition by Kabat), of tyrosine, by isoleucine.

Ten µl of each of plasmids MBC1L (λ)/pUC19, hMBC1Laλ/pUC19 and hMBC1 Ldλ/pUC19 was digested in 30 µl of a reaction solution comprising 10 mM Tris-HCl (pH 7.5), 10 mM MgCl$_2$, 1 mM DTT, 50 mM NaCl, 0.01% (w/v) of BSA, 16U of HindIII and 4U of AflII at 37° C. for 1 hour. The reaction solution was subjected to electrophoresis using 2% low melting agarose gel, and then collected and purified the following DNA fragments using GENECLEA-NII Kit (BIO101): a DNA fragment of 215 bp in length from plasmid MBC1L(λ)/pUC19 (referred to as "c2'") or a DNA fragment of 3218 bp in length from each of plasmids hMBC1 Laλ/pUC19 and hMBC1 Ldλ/pUC19MBC (referred to as "ha1" and "hd1", respectively).

Each of the ha1' and hd1' fragments was individually ligated to the c2' fragment and then introduced into a competent cell of E. coli, JM109, to form a transformant. The transformant was cultured in 2 ml of a 2×YT medium containing 50 µg/ml of ampicillin. From the cell fraction, the plasmid was purified using QIAprep Spin Plasmid Kit (QIAGEN). The resultant plasmid DNAs containing the ha1' fragment and the hd1' fragment were designated "m/hMBC1 Laλ/pUC19" and "m/hMBC1 Ldλ/pUC19", respectively.

Each of the plasmids m/hMBC1 Laλ/pUC19 and m/hMBC1 Ldλ/pUC19 was digested with EcoRI. The DNA fragment of 743 bp in length was electrophoresed using 2% low melting agarose gel, and then collected and purified from the gel using GENECLEANII Kit (BIO101). The resultant was dissolved in 20 µl of a solution comprising 101 mM Tris-HCl (pH 7.4) and 1 mM EDTA.

Four µl of the DNA fragment obtained was mixed with 1 µl of the above-mentioned BAP-treated HEF vector to ligate to each other. The ligation product was introduced into a competent cell of E. coli, JM109, to form a transformant. The transformant was cultured in 2 ml of a 2×YT medium supplemented with 50 µg/ml of ampicillin. From the cell fraction, the plasmid DNA was purified using QIAprep Spin Plasmid Kit (QIAGEN).

The plasmid DNA purified was digested in 20 µl of a reaction solution comprising 20 mM Tris-HCl (pH 8.5), 10 mM MgCl$_2$, 1 mM DTT, 100 mM KCl, 8U of HindIII (Takara Shuzo) and 2U of PvuI (Takara Shuzo) at 37° C. for 1 hour. In this step, the plasmid DNA was identified based on the expectation that if the DNA fragment was inserted in the plasmid in a correct orientation, this digestion would give a digestion fragment of 5104/2195 bp, whereas if the DNA fragment is inserted in the plasmid in the reverse orientation, this digestion would give a digestion fragment of 4378/2926 bp. The plasmids thus obtained were expression vectors coding for mouse FR1, 2/human FR3, 4 hybrid antibody L-chai, which were designated expression vectors "m/hMBC1 Laλ/neo" and "m/hMBC1 Ldλ/neo", respectively.

(ii) Preparation of FR1/FR2 Hybrid Antibody

An FR1/FR2 hybrid antibody was prepared in the same manner as mentioned above using a SnaBI restriction site present in CDR1.

Ten µg of each of the plasmids MBC1L(λ)/neo and mMBC1L(λ)/neo was digested in 20 µl of a reaction solution comprising 10 mM Tris-HCl (pH 7.9), 10 mM MgCl$_2$, 1 mM DTT, 50 mM NaCl, 0.01% (w/v) of BSA and 6 U of SnaBI (Takara Shuzo) at 37° C. for 1 hour. The resultant reaction solution was further digested in 50 µl of a reaction solution comprising 20 mM Tris-HCl (pH 8.5), 10 mM MgCl$_2$, 1 mM DTT, 100 mM KCl, 0.01% (w/v) of BSA and 6U of PvuI at 37° C. for 1 hour.

The resultant reaction solution was subjected to electrophoresis using 1.5% low melting agarose gel, and then DNA fragments of 4955 bp and 2349 bp in length were collected and purified from the gel using GENECLEANII Kit (BIO101). The DNA fragments obtained from plasmid MBC1L(λ)/neo were designated "m1" (4955 bp) and "m2" (2349 bp) and the DNA fragments obtained from plasmid h/mMBC1L(λ)/neo were designated "hm1" (4955 bp) and "hm2" (2349 bp). Each of the DNA fragments obtained was dissolved in 40 µl of a solution comprising 10 mM Tris-HCl (pH 7.4) and 1 mM EDTA.

One µl of each of the m1 and hm1 fragments was ligated to 4 µl of each of the hm2 and m2 fragments, respectively, and then introduced into a competent cell of E. coli, JM109, to form a transformant. The transformant obtained was cultured in 2 ml of a 2×YT medium containing 50 µg/ml of ampicillin. From the cell fraction, the plasmid DNA was purified using QIAprep Spin Plasmid Kit QIAGEN).

The plasmid DNA purified was digested in 20 µl of a reaction solution comprising 10 mM Tris-HCl (pH 7.5), 10 mM $MgCl_{21}$ 1 mM DTT and either 8U of ApaI (Takara Shuzo) or 2U of ApaII (Takara Shuzo) at 37° C. for 1 hour.

The plasmids (m1-hm2 and hm1-m2) thus prepared were identified based on the expectation that if each of the DNA fragments is ligated in the plasmid in a correct orientation, the digestion of the plasmid (m 1-hm2) with ApaI and ApaLI would give a fragment of 7304 bp and fragments of 5560/1246/498 bp, respectively, and the digestion of the plasmid (hm1-m2) with ApaI and ApaLI would give fragments of 6538/766 bp and a fragment of 3535/2025/1246/498 bp, respectively.

As expression vector coding for a human FR1/mouse FR2, 3, 4 hybrid antibody L chain was designated "hmmMBC1L(λ)/neo" and a expression vector cording for a mouse FR1/human FR2/mouse FR3, 4 hybrid antibody L chain was designated "mhmMBC1L(λ)/neo".

(4) Construction of Humanized Antibody L Chain

A humanized #23-57-137-1 antibody L chain was prepared by CDR-grafting technique by means of PCR method. That is, a humanized #23-57-137-1 antibody L chain (version "a") was prepared which contained FR1, FR2 and FR3 drived from human antibody HSU03868 (GEN-BANK, Deftos M. et al., Scand. J. Immunol., 39, 95–103, 1994) and FR4 drived from human antibody S25755 (NBRF-PDB) using the six types of PCR primers:

CDR-grafting primers, MBC1LGP1 (SEQ ID NO: 29) and MBC1LGP3 (SEQ ID NO: 30), both having a sense DNA sequence, CDR-grafting primers, MBC1LGP2 (SEQ ID NO: 31) and MBC1LGP4 (SEQ ID NO: 32), both having an antisense DNA sequence, all of which CDR-grafting primers having a complementary sequence of 15–21 bp on the both ends thereof; and external primers, MBC1LVS1 (SEQ ID NO: 33) and MBC1LVR1 (SEQ ID NO: 34), both having a homology with the CDR-grafting primers MBC1LGP1 and MBC1LGP4, respectively.

The CDR-grafting primers MBC1LGP1, MBC1LGP2, MBC1LGP3 and MBC1LGP4 were isolated using a urea-denatured polyacrylamide gel (Molecular Cloning: A Laboratory Manual, Sambrook et al., Cold Spring Harbor Laboratory Press, 1989) and extracted from the gel fraction by a crush-and-soak method (Molecular Cloning: A Laboratory Manual, Sambrook et al., Cold Spring Harbor Laboratory Press, 1989).

One nmole of each of the CDR-grafting primers was isolated with 6% denatured polyacrylamide gel. From the resultant, a DNA fragment having a desired length was identified on a silica gel thin plate by irradiation of UV ray and then collected therefrom by a crush-and-soak method. The resultant was dissolved in 20 µl of a solution comprising 10 mM Tris-HCl (pH 7.4) and 1 mM EDTA.

The PCR reaction was conducted using TaKaRa Ex Taq (Takara Shuzo) with a buffer. The reaction solution (100 µl) used in the PCR reaction comprised 1 µl of each of the CDR-grafting primers MBC1LGP1, MBC1LGP2, MBC1LGP3 and MBC1LGP4, 0.25 mM dNTP, 2.5 U of TaKaRa Ex Taq in the buffer. Five cycles of the PCR reaction was conducted using a temperature cycle of 94° C. for 1 min., 55° C. for 1 min. and 72° C. for 1 min. Into the resultant reaction mixture were added 50 pmoles of each of the external primers MBC1LVS1 and MBC1LVR1. Using this reaction mixture, additional thirty cycles of the PCR reaction was conducted using the same temperature cycle. The DNA fragment thus amplified was isolated by agarose gel electrophoresis using 3% Nu Sieve GTG agarose (FMC Bio. Products).

An agarose fragment containing a DNA fragment of 421 bp in length was excised and the DNA fragment was purified from the gel using GENECLEANII Kit (BIO101) in accordance with the instruction included with the kit. The PCR reaction mixture thus prepared was used for subcloning of the DNA fragment into plasmid pUC19 which had been prepared by digesting the plasmid with BamHI and HindIII. The resultant plasmid was determined of its DNA sequence. The plasmid thus prepared was designated "hMBCL/pUC19". In this plasmid, however, it was found that the 104-position amino acid (amino acid number 96 according to the determining by Kabat) of CDR4 was replaced with arginine. To correct this amino acid to tyrosine, primer MBC1LGP10R (SEQ ID NO: 35) was designed and synthesized. Then the PCR reaction was conducted using TaKaRa Ex Taq (Takara Shuzo) with a buffer. The reaction solution (100 µl) used in the PCR reaction comprised 0.6 µg of the plasmid hMBCL/pUC19 as a template DNA, 50 pmoles of each of the primers MBC1LVS1 and MBC1LGP10R, 2.5U of TaKaRa Ex Taq (Takara Shuzo) and 0.25 mM dNTP in the buffer, over which mineral oil was layered. Thirty cycles of the PCR reaction was conducted using a temperature cycle of 94° C. for 1 min., 55° C. for 1 min. and 72° C. for 1 min. The DNA fragment thus amplified by PCR method was isolated by agarose gel electrophoresis using 3% Nu Sieve GTG agarose (FMC Bio. Products).

A DNA fragment of 421 bp in length was excised and the DNA fragment was purified therefrom using GENECLEANII Kit (BIO101) in accordance with an instruction included with the kit. The PCR reaction mixture thus prepared was used for subcloning of the DNA fragment into plasmid pUC19 which had been prepared by digesting the plasmid with BamHI and HindIII.

The plasmid was determined of its DNA sequence using M13 Primer M4 and M13 Primer RV. As a result, it was confirmed that the plasmid had a correct sequence. The plasmid was then digested with HindIII and B1nI and a DNA fragment of 416 bp was isolated there from by electrophoresis using 1% agarose gel. The DNA fragment was purified using GENECLEANII Kit (BIO101) in accordance with an instruction included with the kit and then introduced into plasmid Cλ/pUC which had been prepared by digesting the plasmid with HindIII and B1nI. The resultant plasmid was designated "hMBC1 Laλ/pUC19". This plasmid was digested with EcoRI to obtain a DNA fragment coding for humanized L chain. The DNA fragment was introduced into plasmid pCOS1 so that the initiation codon for the humanized L chain was located downstream from the EF1α promoter. The plasmid thus obtained was designated "hMBC1 Laλ/pCOS1". The DNA sequence (including the corresponding amino acid sequence) of the humanized L chain version "a" is shown in SEQ ID NO: 66. The amino acid sequence of the version "a" is shown in SEQ ID NO: 47.

Version "b" was prepared using mutagenic introduction technique by a PCR method. The version "b" was designed so as to replace the 43-position amino acid, glycine, (amino acid number 43 according to the definition by Kabat) with proline and to replace the 49-position amino acid, lysine, (amino acid number 49 according to the definition by Kabat) with aspartic acid. The PCR reaction was conducted using plasmid hMBC1 Laλ/pUC19 as a template with a mutagenic primer MBC1LGP5R (SEQ ID NO: 36) and primer MBC1LVS1. The DNA fragment obtained was digested with BamHI and HindIII, and the digestion fragment was subcloned into the BamHI-HindIII site of pUC19. After sequencing, the plasmid DNA obtained was digested with HindIII and Af1II, and the resultant digestion fragment was ligated to plasmid hMBC1 Laλ/pUC19 which had been prepared by digesting the plasmid with HindIII and Af1II.

The plasmid thus obtained was designated "hMBC1 Lbλ/pUC19". This plasmid DNA was digested with EcoRI to obtain a DNA fragment containing a DNA coding for the humanized L chain. The DNA fragment was introduced into plasmid pCOS1 so that the initiation codon for the humanized L chain was located downstream from the EF1α promoter. The plasmid thus obtained was designated "hMBC1Lbλ/pCOS1".

Version "c" was prepared using mutagenic introduction technique by a PCR method. The version "c" was designed so as to replace the 84-position amino acid, serine, (amino acid number 80 according to the definition by Kabat) with proline. The PCR reaction was conducted using plasmid hMBC1 Laλ/pUC19 as a template with a mutagenic primer MBC1LGP6S (SEQ ID NO: 37) and primer M13 Primer RV. The DNA fragment obtained was digested with BamHI and HindIII and then subcloned into pUC19 which had been prepared by digesting the plasmid with BamHI and HindIII. After sequencing, the plasmid DNA obtained was digested with BstPI and Aor51HI, and the resultant DNA fragment was ligated to plasmid hMBC1Laλ/pUC19 which had been prepared by digesting the plasmid with BstPI and Aor51HI. The plasmid thus obtained was designated "hMBC1 Lcλ/pUC19". This plasmid DNA was digested with EcoRI to obtain a sequence containing a sequence coding for the humanized L chain. The sequence was introduced into the EcoRI site of plasmid pCOS1 so that the initiation codon for the humanized L chain was located downstream from the EF1α promoter. The plasmid thus obtained was designated "hMBC1 Lcλ/pCOS1".

Versions "d", "e" and "f" were also prepared using mutagenic introduction technique by a PCR method. Each of the versions "d", "e" and "f" was designed so as to replace the 91-position amino acid, tyrosine, (amino acid number 87 according to the definition by Kabat) with isoleucine in the versions "a", "b" and "c", respectively. For each of the versions "d", "e" and "f", a PCR reaction was conducted using each of plasmid hMBC1 Laλ/pCOS1 (for version "d"), hMBC1Lb λ/pCOS1 (for version "e") and hMBC1 Lcλ/pCOS1 (for version "f") as a template with a mutagenic primer MBC1LGP11R (SEQ ID NO: 38) and primer M-S1 (SEQ ID NO: 44). The DNA fragment thus obtained was digested with BamHI and HindIII and then subcloned into pUC19 which had been prepared by digesting pUC19 with BamHI and HindIII. After sequencing, the plasmid was digested with HindIII and B1nI, and the resultant digestion fragment was ligated to plasmid Cλ/pUC19 which had been prepared by digesting the plasmid with HindIII and B1nI.

The plasmids thus obtained were respectively designated "hMBC1 Ldλ/pUC19", "hMBC1 Leλ/pUC19" and "hMBC1 Lfλ/pUC19". Each of these plasmids was digested with EcoRI to obtain a DNA fragment containing a DNA coding for the humanized L chain. The DNA fragment was introduced into the EcoRI site of plasmid pCOS1 so that the initiation codon for the humanized L chain was located downstream from the EF1α promoter of the plasmid. The plasmids thus obtained were respectively designated "hMBC1 Ldλ/pCOS1", "hMBC1eλ/pCOS1" and "hMBC1 Lfλ/pCOS1".

Versions "g" and "h" were also prepared using mutagenic introduction technique by a PCR method. Each of the versions "g" and "h" was designed so as to replace the 36-position amino acid, histidine, (amino acid number 36 according to the definition by Kabat) with tyrosine in the versions "a" and "d", respectively. The PCR reaction was conducted with mutagenic primer MBC1LGP9R (SEQ ID NO: 39) and M13 Primer RV using plasmid hMBC1 Laλ/pUC19 as a template. The PCR product was subjected to an additional PCR reaction using M13 Primer M4 as a primer and plasmid hMBC1 Laλ/pUC19as a template. The DNA fragment obtained was digested with HindIII and B1nI and then subcloned into plasmid Cλ/pUC19 which had been prepared by digesting the plasmid with HindIII and B1nI. Using this plasmid as a template, a PCR reaction was conducted using primers MBC1LGP13R (SEQ ID NO: 40) and MBC1LVS1. The PCR fragment obtained was digested with ApaI and HindIII and then introduced into each of plasmids hMBC1 Laλ/pUC19 and hMBC1 Ldλ/pUC19 which had been prepared by digesting both plasmids with ApaI and HindIII. The plasmids obtained were determined of their DNA sequences. Plasmids which were confirmed to contain a correct sequence were designated "hMBC1 Lgλ/pUC19" and "hMBC1 Lhλ/pUC19", respectively. Each of these plasmids was digested with EcoRI to obtain a sequence containing a sequence coding for the humanized L chain. The sequence was introduced into the EcoRI site of plasmid pCOS1 so that the initiation codon for the humanized L chain was located downstream from the EF1α promoter. The plasmids thus obtained were respectively designated "hMBC1Lgλ/pCOS1" and "hMBC1 Lhλ/pCOS1".

Versions "i", "j", "k", "l" "m", "n" and "o" were also prepared using mutagenic introduction technique by a PCR method. The PCR reaction was conducted using a mutagenic primer MBC1LGP14S (SEQ ID NO: 41) and primer V1RV (λ) (SEQ ID NO: 43) using plasmid hMBC1 Laλ/pUC19 as a template. The resultant DNA fragment was digested with ApaI and B1nI and then subcloned into plasmid hMBC1 Lgλ/pUC19 which had been prepared by digesting the plasmid with ApaI and B1nI. The plasmid obtained was determined of its base sequence, and the clone into which the mutation corresponding to each of the versions was introduced, was selected. The plasmid thus obtained was designated "hMBC1 Lxλ/pUC19 (x=i, j, k, l, m, n or o)". This plasmid was digested with EcoRI to obtain a sequence containing a sequence coding for the humanized L chain. The sequence was introduced into the EcoRI site of plasmid pCOS1 so that the initiation codon for the humanized L chain was located downstream from the EF1α promoter. The plasmid thus obtained was designated "hMBC1 Lxλ/pCOS1" (x=i, j, k, l, m, n or o). The DNA sequences (including the corresponding amino acid sequences) of the versions "j", "l", "m" and "o" are shown in SEQ ID NOs: 67, 68, 69 and 70, respectively. The amino acid sequences of these versions are shown in SEQ ID Nos: 48, 49, 50 and 51, respectively.

Versions "p", "q", "r", "s" and "t" are modified form of the versions "i", "j", "m", "l" and "o", respectively, in which the 87-position amino acid, tyrosine, is replaced with isoleucine. These versions were prepared by using the Aor51MI restriction site of FR3 for replacement of the version "h" with the version "i", "j", "m", "l" or "o" in the following manner. From expression plasmid hMBC1 Lxλ/pCOS1 (x=i, j, m, l or o), an Aor51HI restriction fragment (514 bp)

containing CDR3, a portion of FR3 and entire FR4 were deleted. To the deleted portion of the expression plasmid was ligated an Aor51HI restriction fragment (514 bp) containing CDR3 and a portion of FR3 and entire FR4 so that the 91-position amino acid, tyrosine, (the amino acid number 87 according to the definition by Kabat) is replaced with isoleucine. The resultant plasmids were determined of their DNA sequence and the clone of each of the versions "i", "j", "m", "l" and "o" in which 91-position amino acid, tyrosine, (the amino acid number 87 according to the definition by Kabat) was replaced with isoleucine was selected. The versions corresponding to the versions "i", "j", "m", "l" and "o" were designated versions "p", "q", "s", "r", and "t", respectively, and the plasmids for these versions were designated "hMBC1 Lxλ/pCOS1 (x=p, q, s, r or t). The DNA sequences (including the corresponding amino acids) of the versions "q", "r", "s" and "t" are shown in SEQ ID Nos: 71, 72, 73 and 74, respectively. The amino acid sequences of these versions are shown in SEQ ID Nos: 52, 53, 54 and 55, respectively.

Plasmid hMBC1 Lqλ/pCOS1 was digested with HindIII and EcoRI and then subcloned into plasmid pUC19 by digesting the plasmid with HindIII and EcoRI. The plasmid thus obtained was designated "hMBC1 Lqλ/pUC19.

The position of the replaced amino acids in each version of the humanized L chain is shown in Table 3 below.

TABLE 3

Position of replaced amino acid in sequence lists
(amino acid number according to the definition by Kabat)

| Version | 36 | 43 | 45 | 47 | 49 | 80 | 87 |
|---|---|---|---|---|---|---|---|
| a | | | | | | | |
| b | | P | | | D | | |
| c | | | | | | P | |
| d | | | | | | | I |
| e | | P | | | D | | I |
| f | | | | | | P | I |
| g | Y | | | | | | |
| h | Y | | | | | | I |
| i | Y | | K | | | | |
| j | Y | | K | | D | | |
| k | Y | | K | V | | | |
| l | Y | | K | V | D | | |
| m | Y | | V | | D | | |
| n | Y | | V | | | | |
| o | Y | | V | D | | | |
| p | Y | | K | | | | I |
| q | Y | | K | | D | | I |
| r | Y | | | | D | | I |
| s | Y | | K | V | D | | I |
| t | Y | | | V | D | | I |

In Table 3 above, capital letters represent the following amino acids: Y: tyrosine; P: proline; K: lysine, V: valine; D: aspartic acid; and I: isoleucine.

E. coli strain containing plasmid hMBC1HcDNA/pUC19 and E. coli strain containing plasmid hMBC1 Lqλ/pUC19 were designated "Escherichia coli JM109 (hMBC1 HcDNA/pUC19)" and "Escherichia coli JM109 (hMBC1 Lqλ/pUC19) respectively, which have been deposited under the terms of Budapest Treaty at the National Institute of Bioscience and Human-Technology, Agency of Industrial Science and Technology, Japan, (1–3, Higashi 1-chome, Tsukuba-shi, Ibaragi-ken, Japan) on Aug. 15, 1996 under the accession No. FERM BP-5629 for Escherichia coli JM109 (hMBC1 HcDNA/pUC19) and FERM BP-5630 for Escherichia coli JM109 (hMBC1 Lqλ/pUC19).

(5) Transfection into COS-7 Cell

For determining the antigen-binding activity and the neutralizing activity of the hybrid antibody and the humanized #23-57-137-1 antibody, the above-mentioned expression plasmids were expressed transiently in COS-7 cells. For the transient expression of the L chain hybrid antibody, each of the following combinations of plasmids was co-transfected into a COS-7 cell by electroporation using Gene Pulser (Bio Rad): hMBC1 HcDNA/pCOS1 and h/mMBC1L(λ)/neo; hMBC1 HcDNA/pCOS1 and m/hMBC1 Laλ/neo; hMBC1 HcDNA/pCOS1 and m/hMBC1 Ldλ/neo; hMBC1 HcDNA/pCOS1 and hmmMBC1L(λ)/neo; and hMBC1 HcDNA/pCOS1 and mhmMBC1L(λ)/neo. That is, into 0.8 ml of a cell suspension in which COS-7 cells were suspended in PBS(−) in a concentration of $1 \times 10^7$ cells/ml, 10 μg of each of the plasmid DNAs was added. The resultant solution was applied with pulses at an electrostatic capacity of 1,500V and 25 pF. After 10 min. of recovery period at room temperature, the cells treated by electroporation were suspended in a DMEM medium supplemented with 2% Ultra Low IgG fetal calf serum (GIBCO) and then cultured using a 10 cm culture dish in a $CO_2$ incubator. After culturing for 72 hours, a culture supernatant was collected and centrifuged to remove cell debris. The resultant was provided as a sample for the ELISA assay.

For the transient expression of the humanized #23-57-137-1 antibody, the plasmid combination of either hMBC1 HcDNA/pCOS1 or hMBC1 Lxλ/pCOS1 (x=a−t) was transfected into a COS-7 cell using Gene Pulser (Bio Rad) in the same manner as described for the hybrid antibody above. The culture supernatant obtained was provided as a sample for the ELISA assay.

Here, the purification of the hybrid antibody or the humanized antibody from the culture supernatant of COS-7 cell was conducted using AffiGel Protein A MAPSII Kit (Bio Rad) in accordance with an instruction included in the kit.

(6) ELISA Assay (i) Determination of Antibody Concentration

An ELISA plate for determining antibody concentration was prepared as follows. Each of the wells of a 96-well plate for ELISA (Maxisorp, NUNC) was coated with 100 μl of a coating buffer (0.1 M $NaHCO_3$, 0.02% $NaN_3$) supplemented with 1 μg/ml of goat anti-human IgG antibody (TAGO) and then blocked with 200 μl of a dilution buffer [50 mM Tris-HCl, 1 mM $MgCl_2$, 0.1 M NaCl, 0.05% Tween20, 0.02% $NaN_3$, 1% bovine serum albumin (BSA); pH 7.2]. Into each of the wells was added a culture supernatant of the COS cells in which the hybrid antibody or the humanized antibody was expressed or a solution of the purified hybrid antibody or humanized antibody in stepwise dilution. After incubating at room temperature for 1 hour and washing with PBS-Tween20, 100 μl of alkaline phosphatase-conjugated goat anti-human IgG antibody (TAGO) was added to each of the wells. After incubating at room temperature for 1 hour and washing with PBS-Tween20, 1 mg/ml of a substrate solution ("Sigma104", p-nitrophenylphosphoric acid, SIGMA) was added to each of the wells. The solution was measured for absorbance at 405 nm using Microplate Reader (Bio Rad). As the standard for this determination of antibody concentration, Hu IgG1λ Purified (The Binding Site) was used.

(ii) Determination of Antigen Binding Ability

An ELISA plate for determining antigen binding ability was prepared as follows. Each of the wells of a 96-well plate for ELISA (Maxisorp, NUNC) was coated with 100 μl of a coating buffer supplemented with 1 μg/ml of human PTHrP (1–34) and then blocked with 200 μl of a dilution buffer. Thereafter, into each of the wells, was added a culture supernatant of the COS-7 cells in which the hybrid antibody or humanized antibody was expressed or a solution of the purified hybrid antibody or the purified humanized antibody in stepwise dilution. After incubating at room temperature and washing with PBS-Tween20, 100 μl of alkaline phosphatase-conjugated goat anti-human IgG antibody (TAGO) was added to each of the wells. After incubating at room temperature and washing with PBS-Tween20, 1 mg/ml of a substrate solution ("Sigma 104", p-nitrophenylphosphoric acid, SIGMA) was added to each of the wells. The solution was measured for absorbance at 405 nm using Microplate Reader (Bio Rad).

(7) Confirmation of Activities (i) Evaluation of Humanized H Chain

Figure 5:
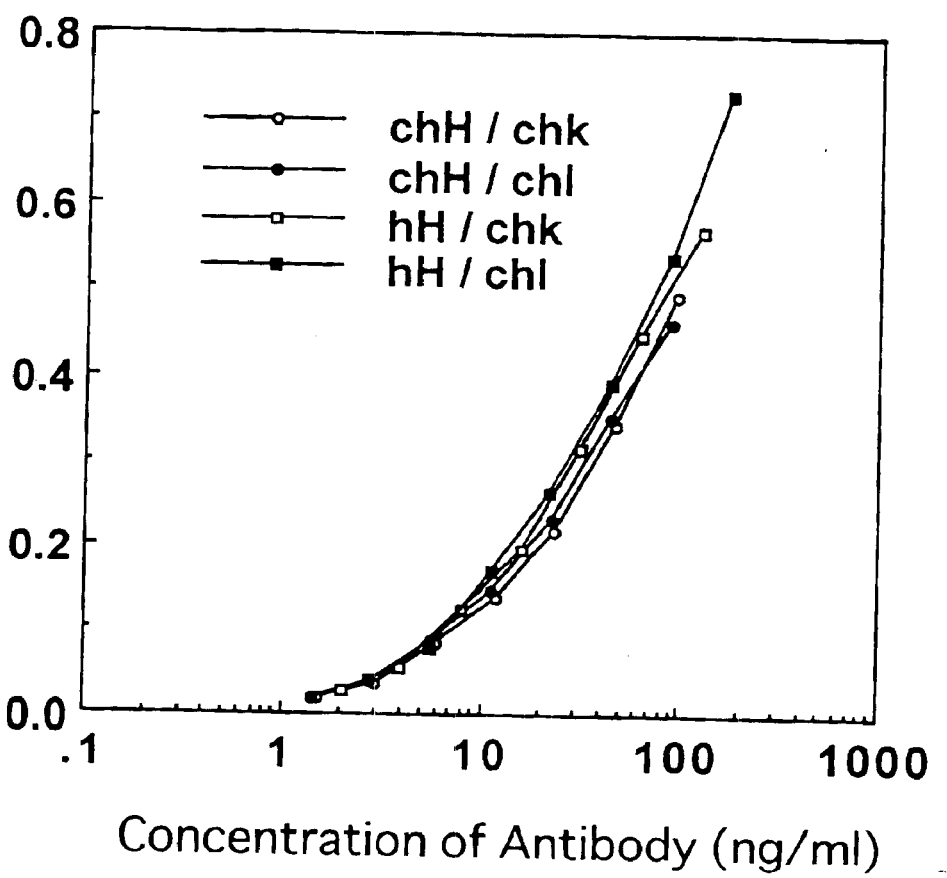
FIG. 5 is a graph showing the measurement result of the antigen-binding activity of the antibodies.

It was found that an antibody comprising the humanized H chain version "a" and the chimeric L chain exhibited the same level of PTHrP-binding activity as that of the chimeric antibody (see FIG. 5). This result suggests that the humanization of the H chain V region is satisfactorily achieved by the version "a". Therefore, the humanized H chain version "a" was provided as a humanized antibody H chain in the following experiments.

(ii) Activity of Hybrid Antibody (ii-a) FR1, 2/FR3, 4 Hybrid Antibody

Figure 6:
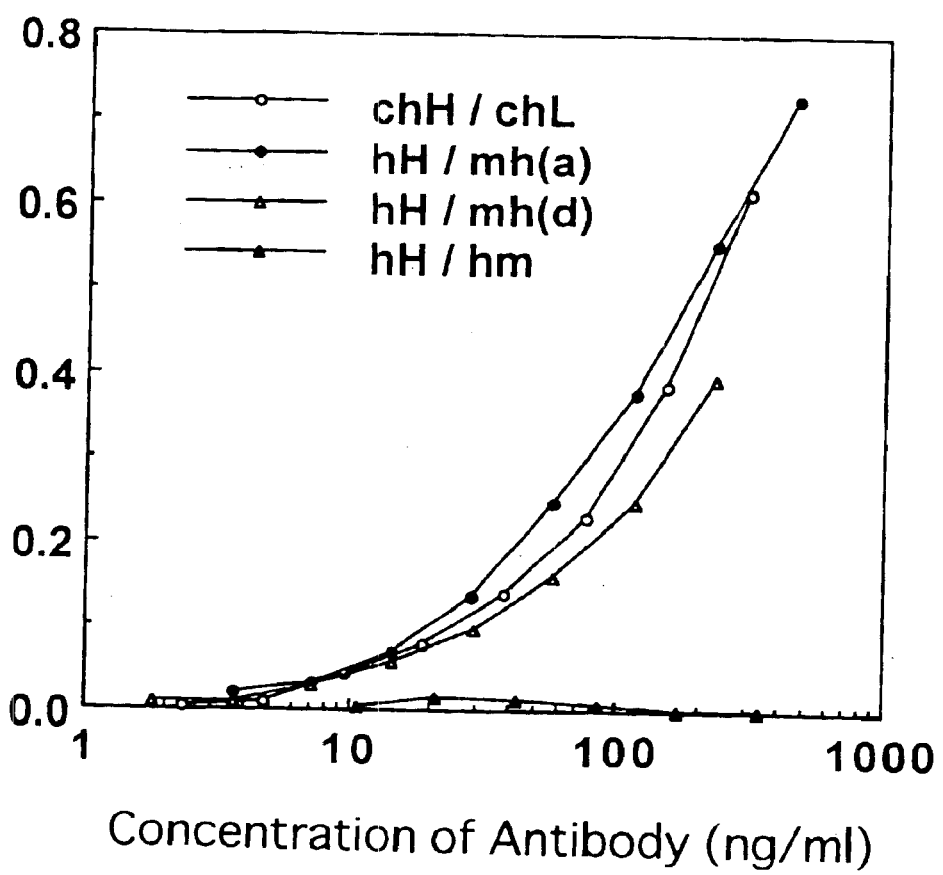
FIG. 6 is a graph showing the measurement result of the antigen-binding activity of the antibodies.

When the L chain was h/mMBC1Ld(λ), the antibody showed no antigen binding activity. However, when the L chain of the hybrid antibody was either m/hMBC1 Laλ or m/hMBC1 Ldλ, the antibody showed the same level of antigen binding activity as that of the chimeric #23-57-137-1 antibody (FIG. 6). These results suggest that FR3 and FR4 are suitable for a humanized antibody but there exist amino acid residue(s) that need to be replaced in FR1 and FR2.

(ii-b) FR1/FR2 Hybrid Antibody

Figure 7:
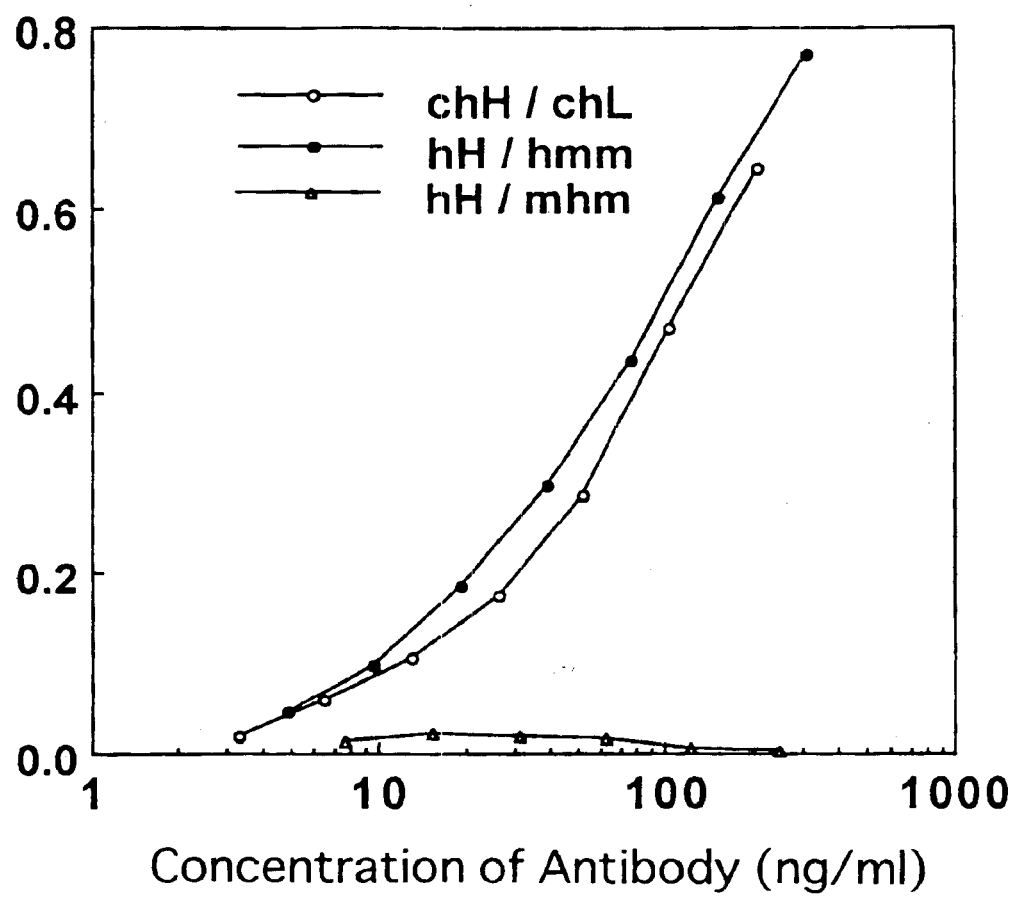
FIG. 7 is a graph showing the measurement result of the antigen-binding activity of the antibodies.
Figure 8:
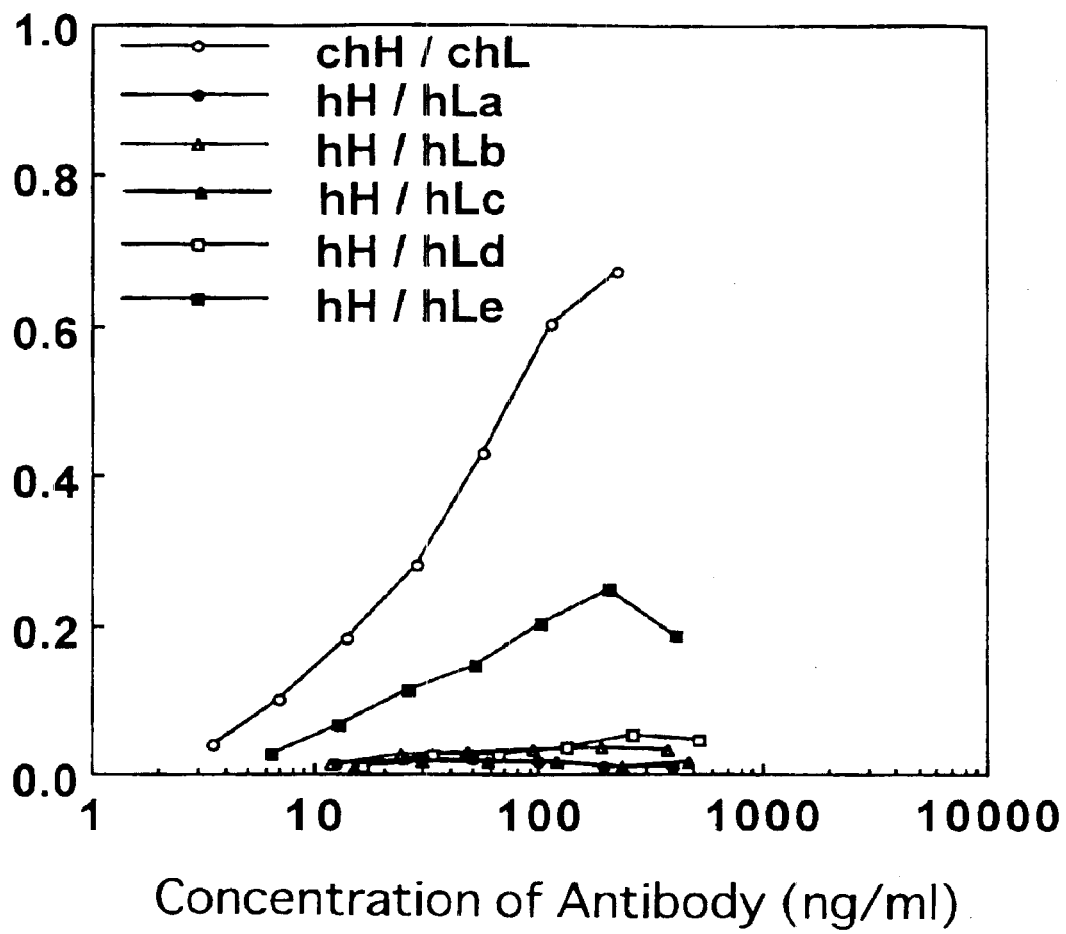
FIG. 8 is a graph showing the measurement result of the antigen-binding activity of the antibodies.
Figure 9:
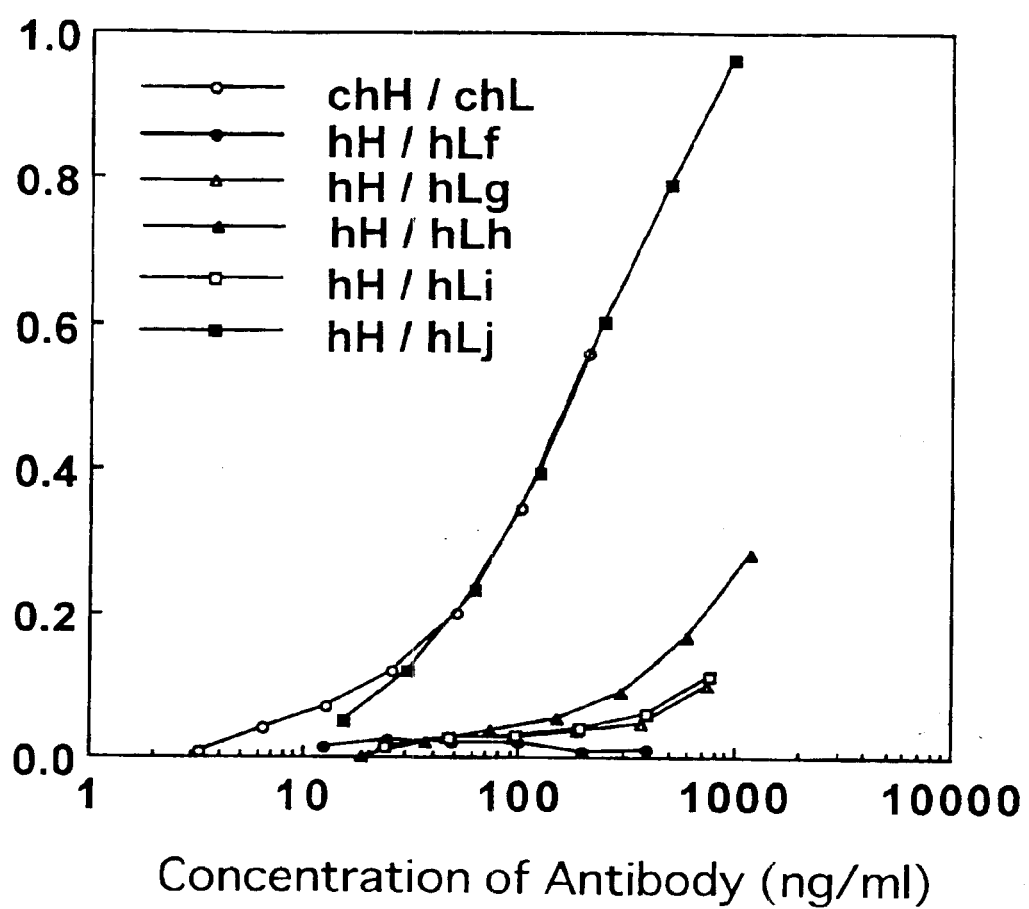
FIG. 9 is a graph showing the measurement result of the antigen-binding activity of the antibodies.
Figure 10:
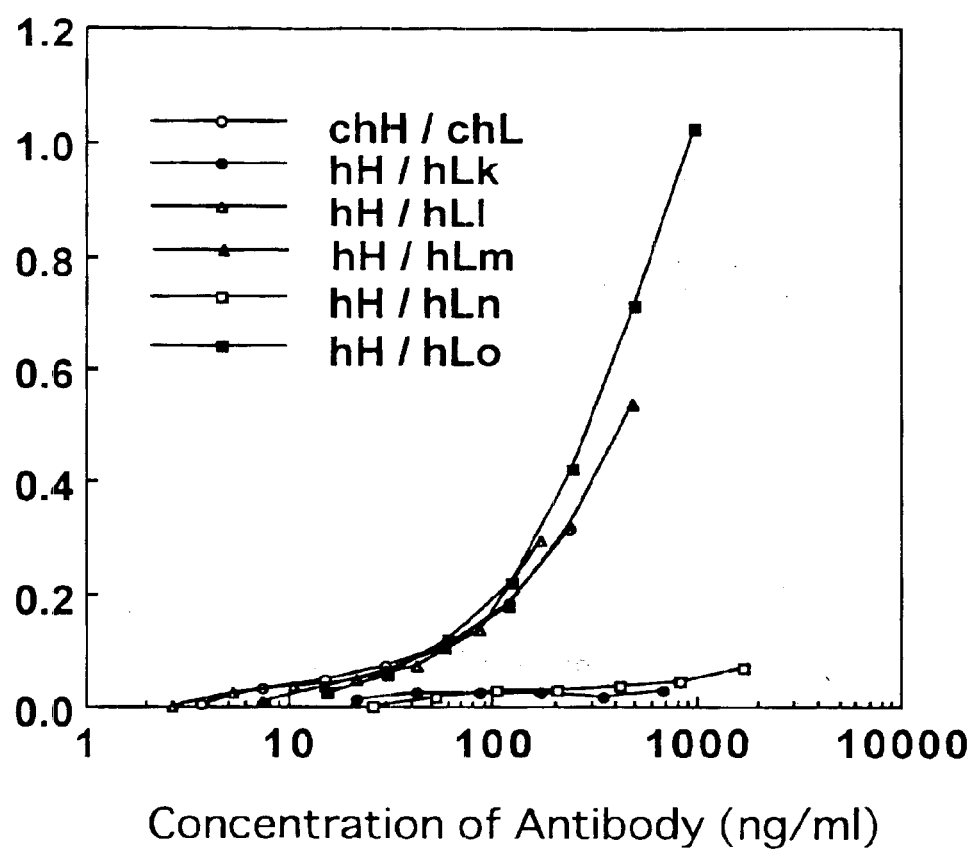
FIG. 10 is a graph showing the measurement result of the antigen-binding activity of the antibodies.
Figure 11:
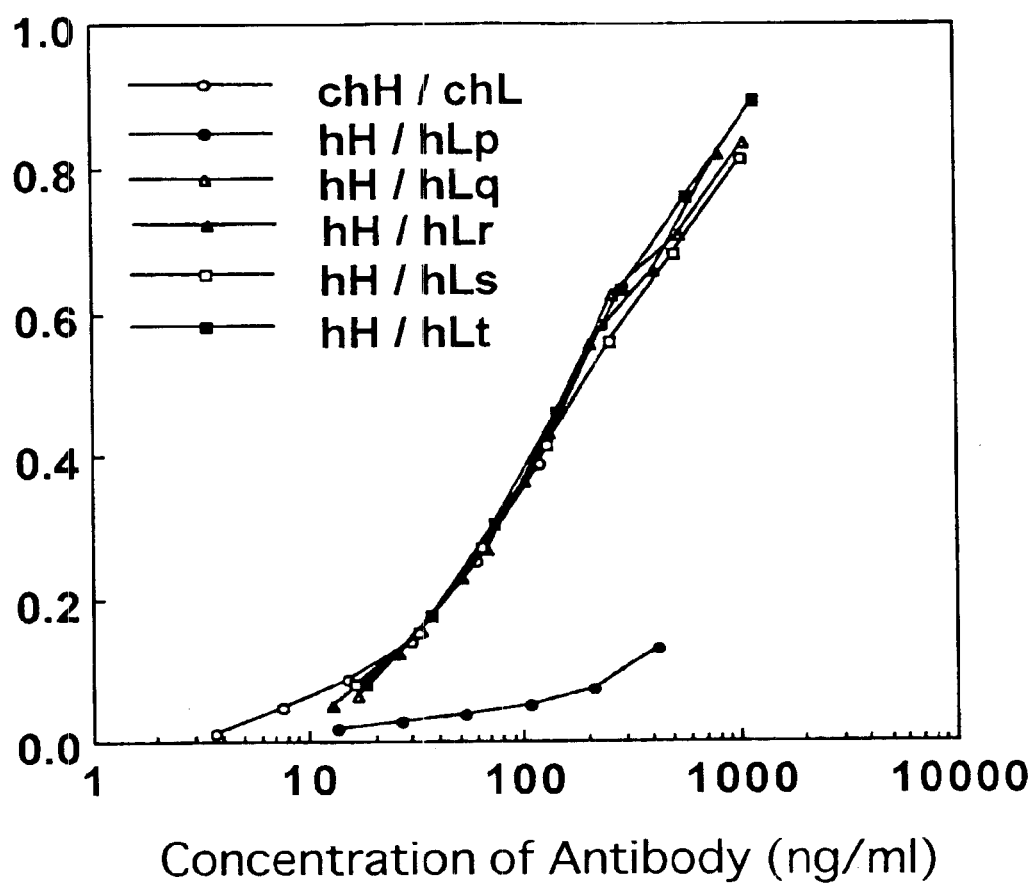
FIG. 11 is a graph showing the measurement result of the antigen-binding activity of the antibodies.

When the L chain of the hybrid antibody was mhmMBC1L (λ), the antibody showed no antigen binding activity. However, when the L chain of the hybrid antibody was hmmMBC1L(λ), the antibody showed the same level of antigen binding activity as that of the chimeric #23-57-137-1 antibody (FIG. 7). These results suggest that FR1 is suitable for a humanized antibody but there exist amino acid residue (s) that need to be replaced in FR2.

(iii) Activity of Humanized Antibody

The humanized antibody in which each of the versions "a" to "t" was used as the L chain was determined of its antigen-binding activity. As a result, it was found that the humanized antibodies having the L chain versions "j", "1" "m", "o", "q", "r", "s" and "t" exhibited the same level of PTHrP-binding activity as that of the chimeric antibody (FIGS. 8 to 11).

(8) Establishment of CHO Stable Production Cell Line

For establishing a stable transformant for humanized antibody, the above-mentioned expression plasmids were introduced into a CHO cell (DXB11).

The establishment of a stable transformant of the humanized antibody was conducted using each of the following combinations of plasmid as an expression vector for CHO cells; hMBC1HcDNA/pCO1 and hMBC1 Lmλ/pCOS1; hMBC1 HcDNA/pCHO1 and hMBC1 Lqλ/pCOS1; and hMBC1 HcDNA/pCHO1 and hMBC1 Lrλ/pCOS1. The plasmids were co-transfected into a CHO cell by electroporation using Gene Pulser (Bio Rad). Subsequently, each of the expression vectors was cleaved with restriction enzyme PvuI to obtain a lenear DNA. The resultant DNA was extracted with phenol and chloroform and then precipitated with ethanol. The DNAs thus prepared were respectively subjected to electroporation as follows. That is, 10 μg of each of the plasmid DNAs was added to 0.8 ml of a cell suspension containing CHO cells in PBS(-) in a concentration of 1×10$^7$ cells/ml. The resultant mixture was applied with pulses at an electrostatic capacity of 1,500V and 25 μF. After 10 min. of recovery period at room temperature, the cells thus treated were suspended in a MEM-α medium (GIBCO) supplemented with 10% fetal calf serum (GIBCO) and then cultured in a $CO_2$ incubator using 96-well plates (Falcon). On the day after starting the cultivation, the medium was replaced by a MEM-α selective medium supplemented with 10% fetal calf serum (GIBCO) and 500 mg/ml of GENETICIN (G418Sulfate; GIBCO) but containing no ribonucleoside or deoxyribonucleoside. From the culture medium, cells into which the antibody gene was introduced were selected. After replacing the culture medium by a fresh one, before and after two weeks of cultivation, the cells were observed microscopically. When a satisfactory cell growth was observed, the cells were determined for the amount of antibodies produced by an ELISA assay conventionally used for determining antibody concentration as described above. Among the cells, those which produced a larger amount of antibodies were selectively collected.

The scale up of the culture of the stable transformant for the antibodies thus established was conducted in a roller bottle using a MEM-α medium supplemented with 2% Ultra Low IgG fetal calf serum without ribonucleoside or deoxyribonucleoside. On each of day 3 and day 4 after the cultivation, the culture supernatant was collected and filtered using a 0.2 μm filter having (Millipore) to remove cell debris therefrom. The purification of the humanized antibodies from the culture supernatant of the CHO cells was conducted using POROS Protein A Column (PerSeptive Biosystems) on ConSep LC100 (Millipore) in accordance with an instruction included. The humanized antibodies were provided as a sample for the determination of neutralizing activity and examination of pharmacological efficacy on hypercalcemic model animals. The concentration and the antigen-binding activity of the purified humanized antibodies were determined by the ELISA system as mentioned above.

EXAMPLE 4

Determination of Neutralizing activity

The determination of neutralizing activity of the mouse antibody, the chimeric antibody and the humanized antibody was conducted using rat myeloma cell line ROS17/2.8–5 cells. The ROS17/2.8–5 cells were cultured in Ham'S F-12 medium (GIBCO) supplemented with 10% fetal calf serum (GIBCO) using a $CO_2$ incubator. The ROS17/2.8–5 cells were inoculated in each of the wells of a 96-well plate in a concentration of 10' cells/100 μl/well and cultured for 1 day. The culture medium was replaced with Ham'S F-12 medium (GIBCO) supplemented with 4 mM Hydrocortisone and 10% fetal calf serum. After culturing for three to four days, the cultured cells were washed with 260 μl of Ham'S F-12 medium (GIBCO), and then 80 μl of Ham's F-12 medium supplemented with 1 mM isobutyl-1-methylxanthine (IBMX, SIGMA), 10% fetal calf serum and 10 mM HEPES was added thereto. The resultant mixture was incubated at 37° C. for 30 min.

Figure 12:
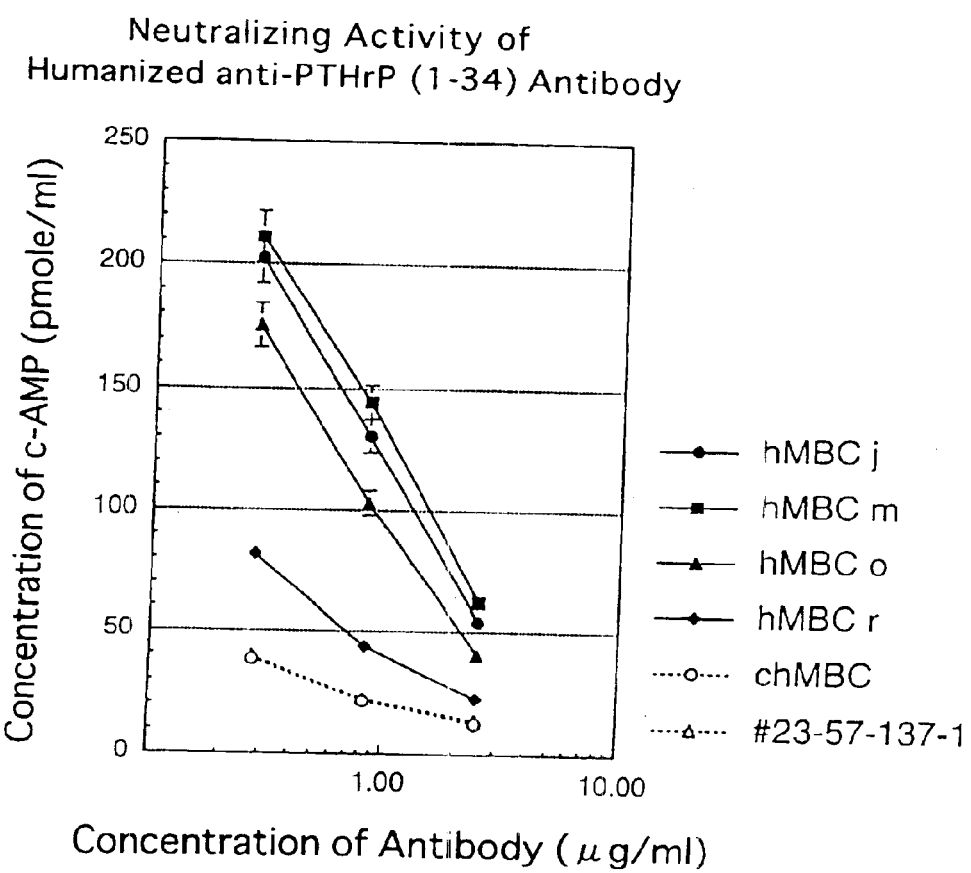
FIG. 12 is a graph showing the neutralizing activity of the humanized antibodies.
Figure 13:
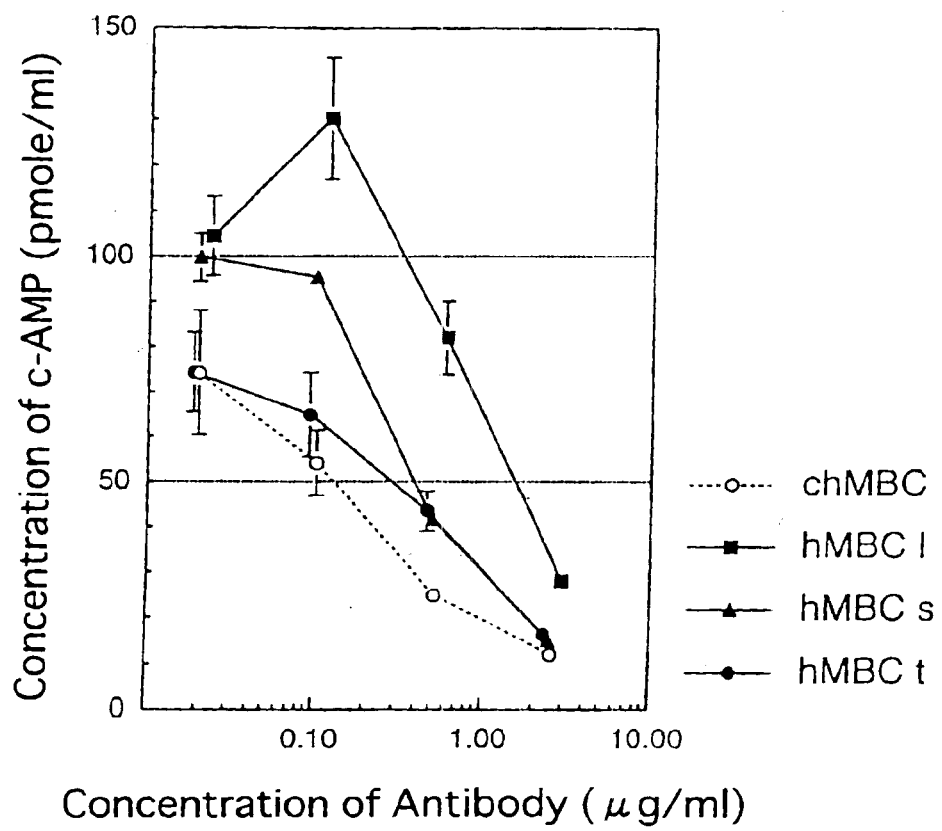
FIG. 13 is a graph showing the neutralizing activity of the humanized antibodies.
Figure 14:
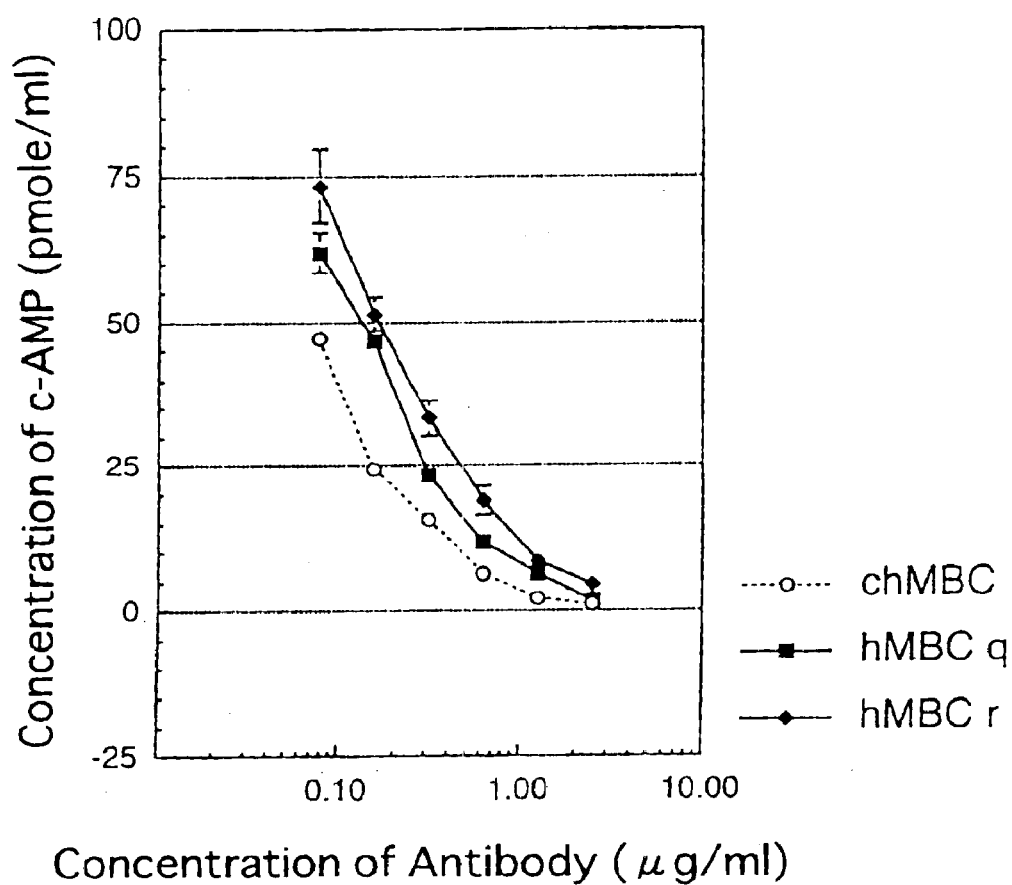
FIG. 14 is a graph showing the neutralizing activity of the humanized antibodies.

The mouse antibody, the chimeric antibody and the humanized antibody to be tested for neutralizing activity were previously diluted stepwise in the following groups: [10 μg/ml, 3.3 μg/ml, 1.1 μg/ml and 0.37 μg/ml], [–10 μg/ml, 2 μg/ml, 0.5 μg/ml and 0.01 μg/ml] and [10 μg/ml, 5 μg/ml, 1.25 μg/ml, 0.63 μg/ml and 0.31 μg/ml]. Each of the diluted antibody sample solution was mixed with an equivalent amount of 4 ng/ml of PTHrP (1–34). Eighty µl of the resultant mixture solution was added into each well. The final concentration of each antibody became a quarter of the concentration of the above-mentioned antibody, and therefore the concentration of PTHrP (1–34) became 1 ng/ml. Ten minutes after the treatment at room temperature, the culture supernatant was removed and the residue was washed with PBS three times. From the resultant, cAMP in the cells was extracted with 10 µl of a 0.3% HCl-95% ethanol and then evaporated with a water jet aspirator to remove the HCl-ethanol. The residue was dissolved in 120 µl of EIA buffer attached to cAMP EIA Kit (CAYMAN CHEMICAL'S) to extract the cAMP therefrom. The CAMP level was determined using cAMP EIA Kit (CAYMAN CHEMICAL'S) in accordance with an instruction included within. As a result, it was found that, among the humanized antibodies having L chain versions showing the same level of antigen-binding activity as that of the chimeric antibody, those having L chain versions "q", "r", "s" and "t" in which the 91-position tyrosine was replaced with isoleucine exhibited the closest neutralizing activity to that of the chimeric antibody, and especially those having a L chain version "q" exhibited the strongest neutralizing activity (FIGS. 12 to 14)

EXAMPLE 5

Examination of Pharmacological Efficacy on Hypercalcemic Model Animals (1)

Using a hypercalcemic model animal (a human tumor transplanted nude mouse), a chimeric antibody and humanized antibodies individually having L chain versions "m", "r" and "q" against PTHrP were examined for their therapeutic efficacy on hypercalcemia.

As a hypercalcemic model animal, was used a nude mouse which had been transplanted with human pancreatic cancer PAN-7 [purchased from the Central Institute for Experimental Animals]. It has been known that a nude mouse which has been transplanted with human pancreatic cancer PAN-7 exhibits an increased calcium concentration in blood as increasing the tumor volume and develops hypercalcemia which is associated with, for example, decrease in body weight and spontaneous activity. In this example, therapeutical effect of the chimeric antibody and the humanized antibody of the invention on hypercalcemia induced by the human pancreatic cancer PAN-7 was examined by the measurement of body weight and calcium concentration in blood of the test animal.

The passage of the human pancreatic cancer PAN-7 was conducted using BALB/c-nu/nu nude mice (Nippon Charles River) in vivo. For the evaluation of pharmacological efficacy, 5weeks-old male BALB/c-nu/nu nude mice (Nippon Charles River) were purchased and then acclimatized them for 1 week, and the mice of 6-weeks-old thus prepared were used for the evaluation. The hupercalcemic model mice were prepared and divided into groups in the following manner. The human pancreatic cancer PAN-7 passed was excised and then finely cut into 3 mm cube of blocks. The resultant tumor blocks were subcutaneously transplanted under the skin flap of the mice at one piece per mouse. Two or three weeks after the transplantation, when it was confirmed that the tumor volume in each of the mice became satisfactorily large, the mice were divided into groups so that tumor volume, calcium concentration in blood and body weights of the mice of the individual groups were averaged, and the mice were used as the hupercalcemic model animals.

The examination of therapeutic efficacy on hypercalcemia was conducted as follows. A single dose of the chimeric antibody or the humanized antibody having a L chain version "m" or r against PTHrP was administered to each of the above-mentioned hypercalcemic model mice via tail vein in a dose amount of 10 or 30 µg per mouse. A single dose of the humanized antibody having a L chain version "q" was administered to each of the above-mentioned hypercalcemic model mice via tail vein in a dose amount of 20 or 60 µg per mouse. On day 1, day 4, day 7 and day 11 after the administration, each of the mice was measured for the calcium concentration in blood and measured for the body weigh to evaluate the pharmacological efficacy of the antibodies. The tumor volume was determined by measuring the major diameter (a mm) and the minor diameter (b mm) of the tumor and calculating using the both measured values according to Galant's equation [$ab^2/2$]. The calcium concentration in blood was determined as ionized calcium concentration in whole blood by drawing blood from each of the mice via the orbit using a hematocrit tube and applying the blood to 643 Automatic $Ca^{++}$/pH Analyzer (CIBA-CORNING).

Figure 15:
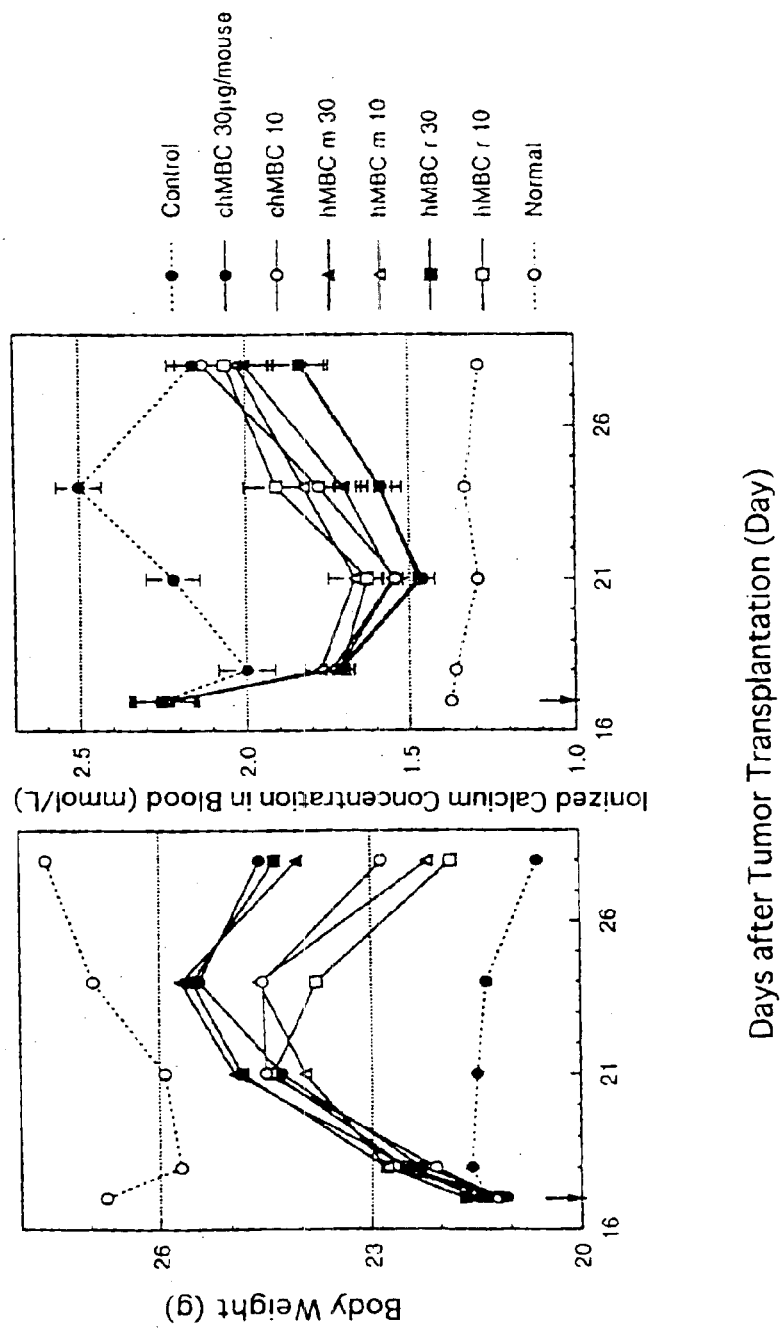
FIG. 15 are graphs illustrating the efficacy of the antibodies of the present invention against a hypercalcemic model animal.
Figure 16:
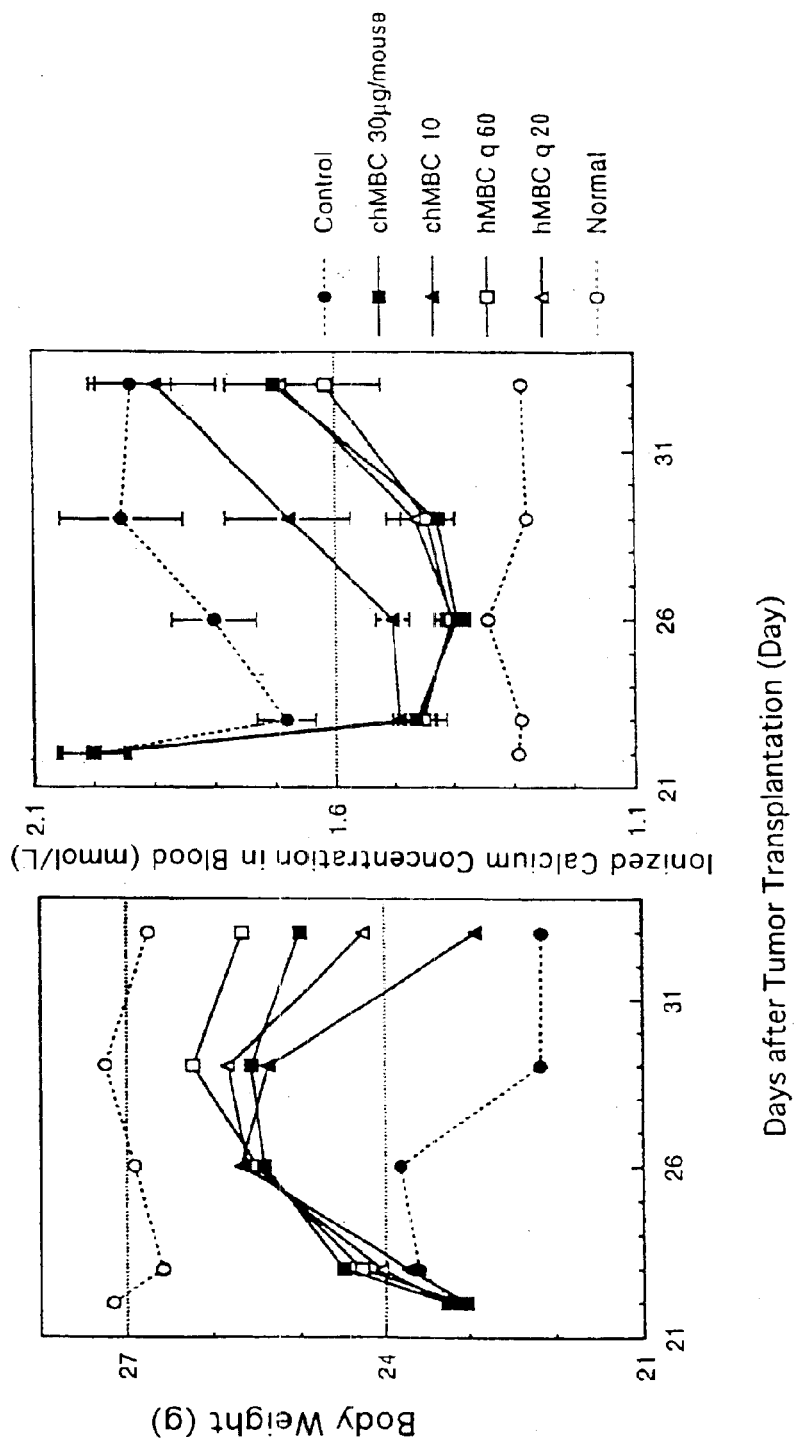
FIG. 16 are graphs illustrating the efficacy of the antibodies of the present invention on a hypercalcemic model animal.

As a result, it was found that the administration of the chimeric antibody and the humanized antibodies each having the L chain versions "m", "r" and "q" leads to a rapid improvement in change of body weight and calcium concentration in blood and a retention of improvement for a prolonged period of time for a subject. This result showed that the chimeric antibody and the humanized antibodies of the present invention are useful for treating malignant tumor-associated hypercalcemia (see FIGS. 15 and 16).

EXAMPLE 6

Examination of Pharmacological Efficacy on Hypercalcemia Model Animals (2)

Using a hypercalcemia model animal (a human tumor transplanted nude mouse), a chimeric antibody and a humanized antibody having L chain version "q" against PTHrP were examined for their therapeutic efficacy on hypercalcemia as follows.

The examination for the therapeutic efficacy on hypercalcemia was conducted as follows. A single dose of the chimeric antibody or the humanized antibody having a L chain version "q" against PTHrP was administered to each of the above-mentioned hypercalcemia model mice via tail vein in a dose amount of 10 or 30 µg per mouse. On day 1, day 3, day 7 and day 11 after the administration, each of the mice was determined for the calcium concentration in blood and measured for the body weigh to evaluate the pharmacological efficacy of the antibodies. The calcium concentration in blood was determined as ionized calcium concentration in whole blood by drawing blood from each of the mice via the orbit using a hematocrit tube and applying the blood to 643 Automatic $Ca^{++}$/pH Analyzer (CIBA-CORNING).

Figure 17:
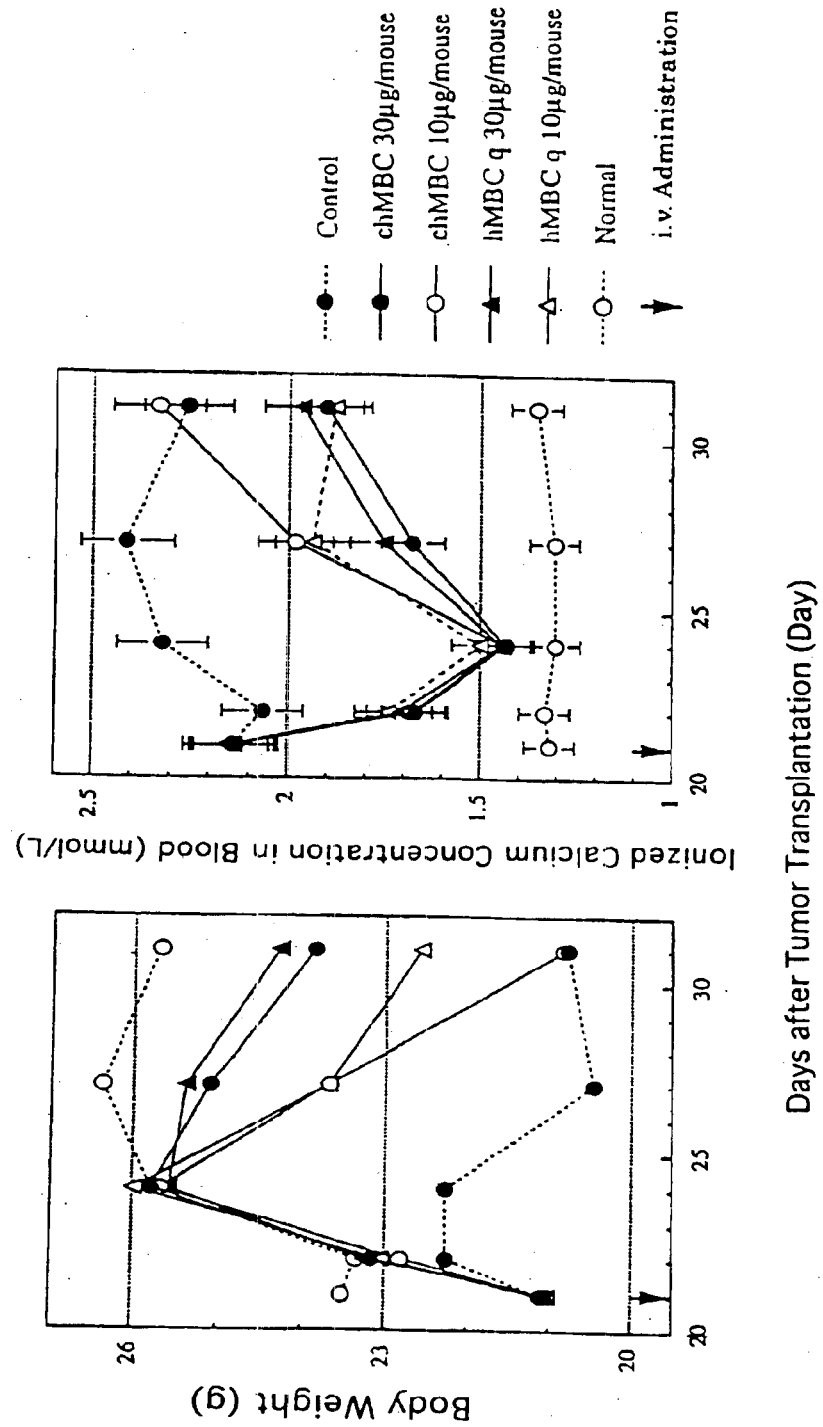
FIG. 17 are graphs illustrating the efficacy of the antibodies of the present invention on a hypercalcemic model animal.

As a result, in the hypercalcemia model animal carrying human pancreatic cancer PAN-7, the administration of the chimeric antibody and the humanized antibody having the L chain version "q" leads to a rapid improvement with respect to body weight and calcium concentration in blood and to a retention of improvement for a prolonged time period for a subject. This result suggests that the chimeric antibody and the humanized antibody of the present invention are useful agent for treating malignant tumor-associated hypercalcemia (see FIG. 17).

EXAMPLE 7

Examination of Pharmacological Efficacy on Hypercalcemia Model Animals (3)

Using a hypercalcemia model animal (a human lung cancer LC-6 transplanted nude mouse), a chimeric antibody and a humanized antibody having L chain version "q" against PTHrP were examined for their therapeutic efficacy on hypercalcemia.

In this experiment, as the hypercalcemia model animal, a nude mouse into which human lung cancer LC-6 (purchased from the Central Institute for Experimental Animals) was transplanted was used. It has been known that a nude mouse into which human lung cancer LC-6 is transplanted tends to show an increased calcium concentration in blood with increased tumor volume and develops hypercalcemia associated with decrease in body weight and spontaneous activity.

In this example, therapeutic efficacy of the chimeric antibody and the humanized antibody of the invention on hypercalcemia induced by the human lung cancer LC-6 was examined by the measurement of body weight and calcium concentration in blood of the test animal.

The passage of the human lung cancer strain LC-6 was conducted using BALB/c-nu/nu nude mice (Nippon Charles River) in vivo. For the evaluation of pharmacological efficacy, 5-weeks-old male BALB/c-nu/nu nude mice (Nippon Charles River) were purchased and then acclimatized them for 1 week, and the mice of 6-weeks-old were used.

The hypercalcemia model mice were prepared and divided into groups in the following manner. The human lung cancer LC-6 passaged was excised and then finely cut into 3 mm cube of blocks. The resultant tumor blocks were subcutaneously transplanted under the skin flap of the mice at one piece per mouse. Two or three weeks after the transplantation, when it was confirmed that the tumor volume in each of the mice had become satisfactorily large, the mice were divided into groups so that tumor volume, calcium concentration in blood and body weight of the mice of the individual groups were averaged, and the mice were used as the hypercalcemia model animals.

The examination of therapeutic efficacy on hypercalcemia was conducted as follows. A single dose of the chimeric antibody or the humanized antibody having a L chain version "q" against PTHrP was administered to each of the above-mentioned hypercalcemia model mice via tail vein in a dose amount of 10 or 30 μg per mouse. On day 1, day 3, day 6 and day 10 after the administration, each of the mice was measured for the calcium concentration in blood and measured for the body weigh to evaluate the pharmacological efficacy of the antibodies. The calcium concentration in blood was determined as ionized calcium concentration in whole blood by drawing blood from each of the mice via the orbit using a hematocrit tube and applying the blood to 643 Automatic $Ca^{++}$/pH Analyzer (CIBA-CORNING).

Figure 18:
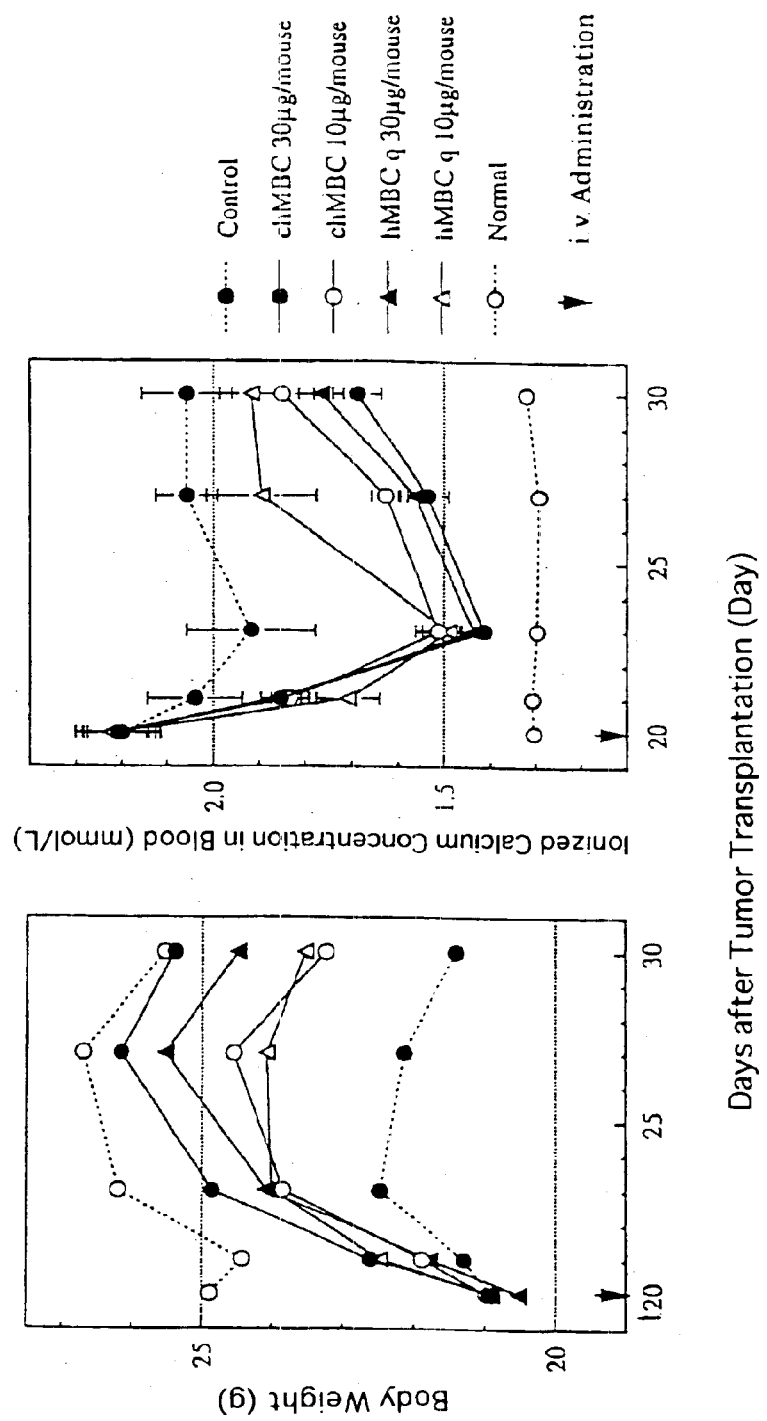
FIG. 18 are graphs illustrating the efficacy of the antibodies of the present invention on a hypercalcemic model animal.

As a result, it was found that in the hypercalcemia model animal carrying human lung cancer LC-6, the administration of the chimeric antibody and the humanized antibody having the L chain version "q" leads to a rapid improvement with respect to body weight and calcium concentration in blood and to a retention of improvement for a prolonged time period for a subject. This result suggests that the chimeric antibody and the humanized antibody of the present invention are useful agent for treating malignant tumor-associating hypercalcemia (see FIG. 18).

EXAMPLE 8

Kinetic Analysis of Interaction between PTHrP and anti-PTHrP Antibody Using BIACORE In this experiment, kinetic analysis of the antigen-antibody interaction using BIACORE was conducted. PTHrP(1–34+Cys) was used as an antigen and adsorbed onto the sensor tip specifically for C-terminals. Purified antibodies of various concentrations were used as an analyte. From the sensorgram obtained, kinetics parameters (binding rate constant "kass" and dissociation rate constant "kdiss") were calculated. With respect to the kinetic analysis, literature "Kinetic analysis of monoclonal antibody-antigen interactions with a new biosensor based analytical system", Karlsson, R. et al., (1991), J. Immunol. Methods 145, p.229–240, was used for reference.

(1) Immobilization of PTHrP (1–34+C) Onto the Sensor Tip
PTHrP (1–34+C) Was Adsorbed Onto Sensor Tip CM5 (Pharmacia).

Figure 19:
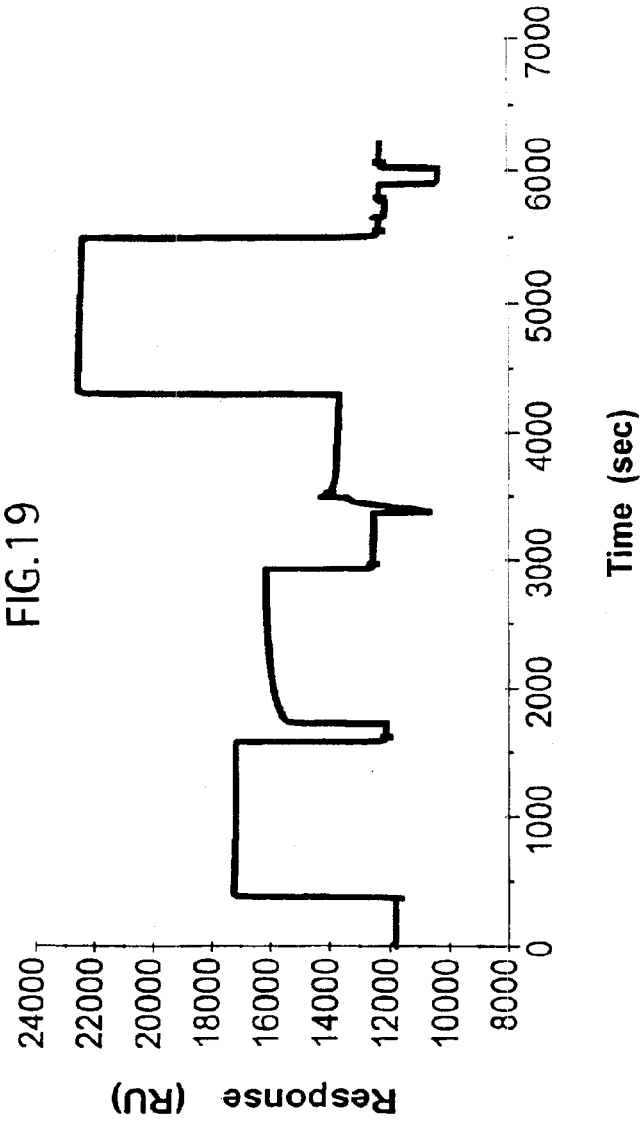
FIG. 19 is a sensorgram illustrating the immobilization of PTHrP onto sensor tip.
Figure 20:
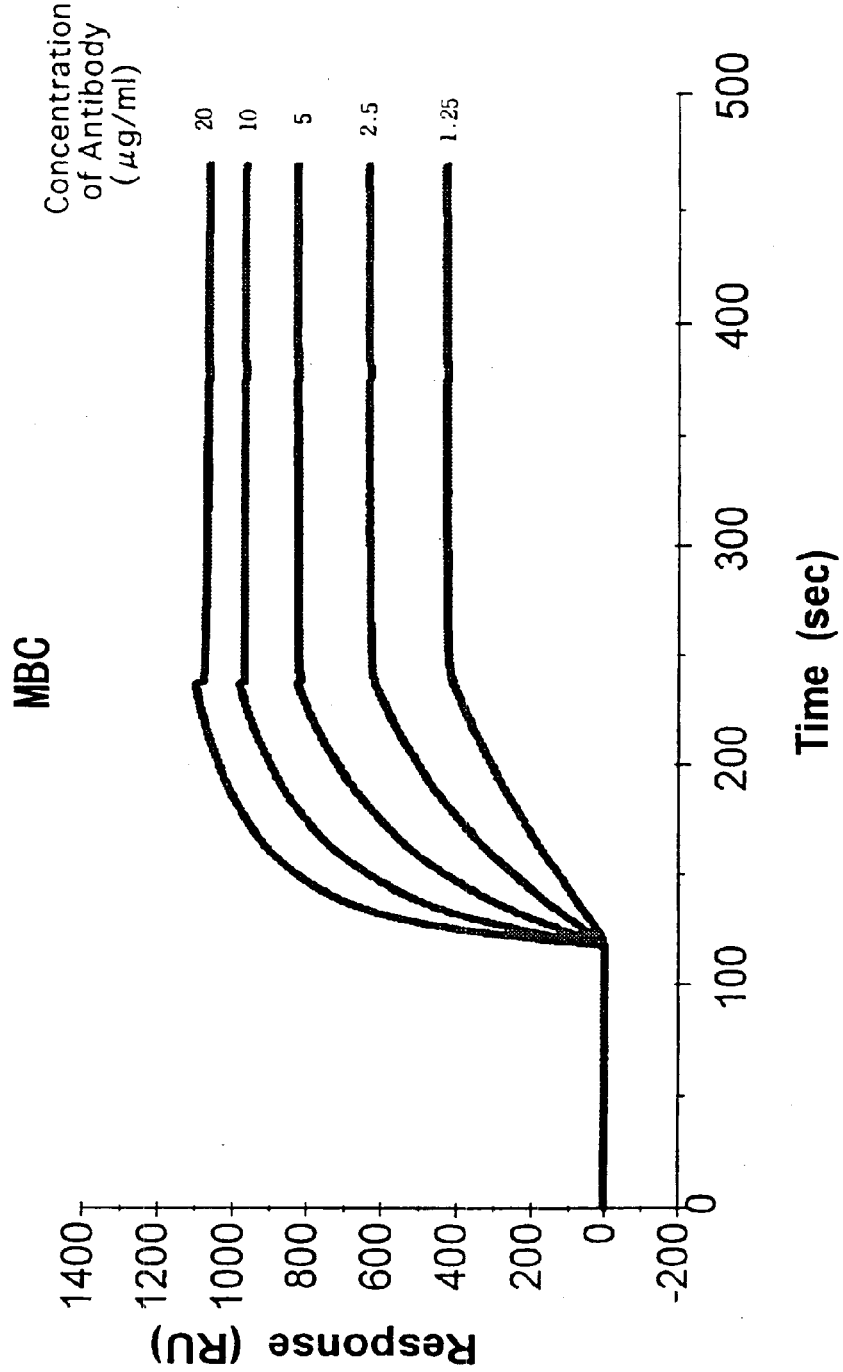
FIG. 20 is a graph showing the results of the kinetic analysis of the antibody according to the invention.
Figure 21:
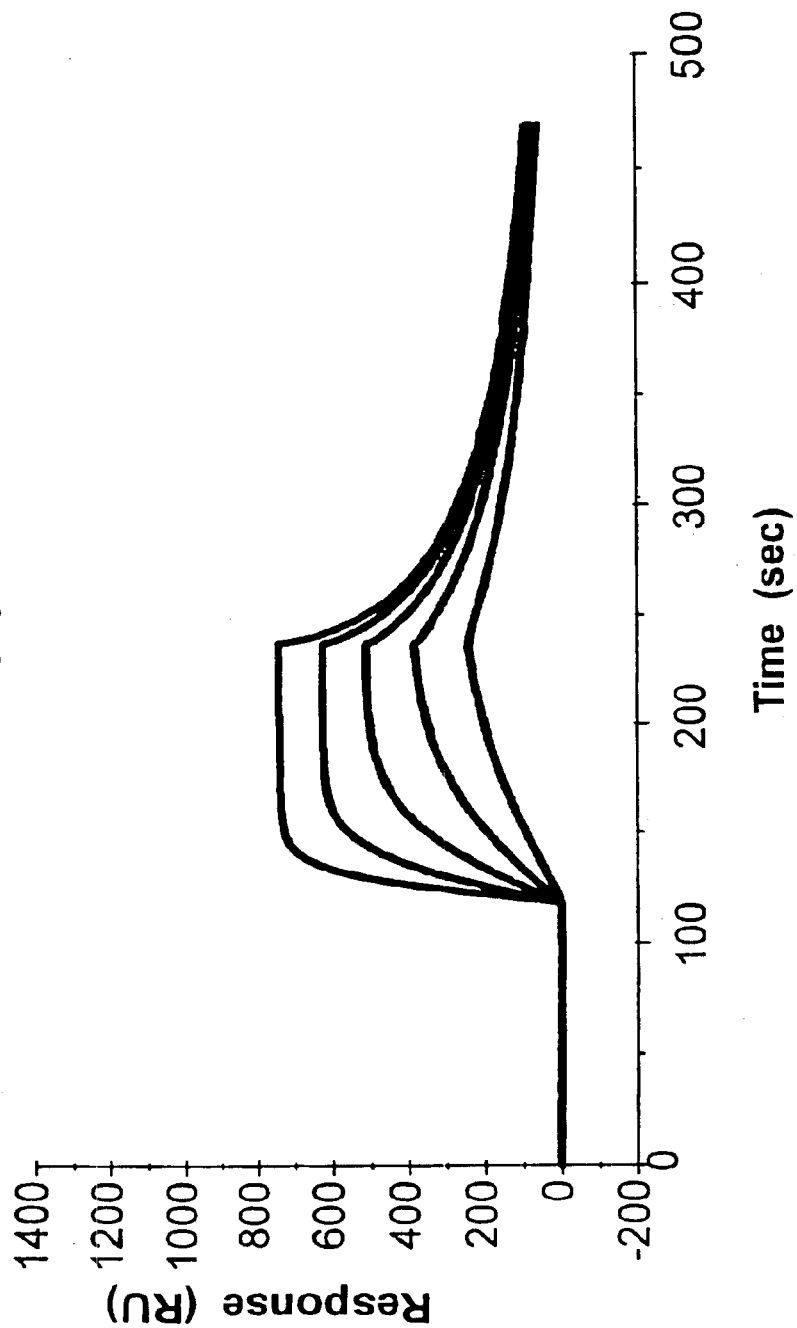
FIG. 21 is a graph showing the results of the kinetic analysis of the antibody according to the invention.
Figure 22:
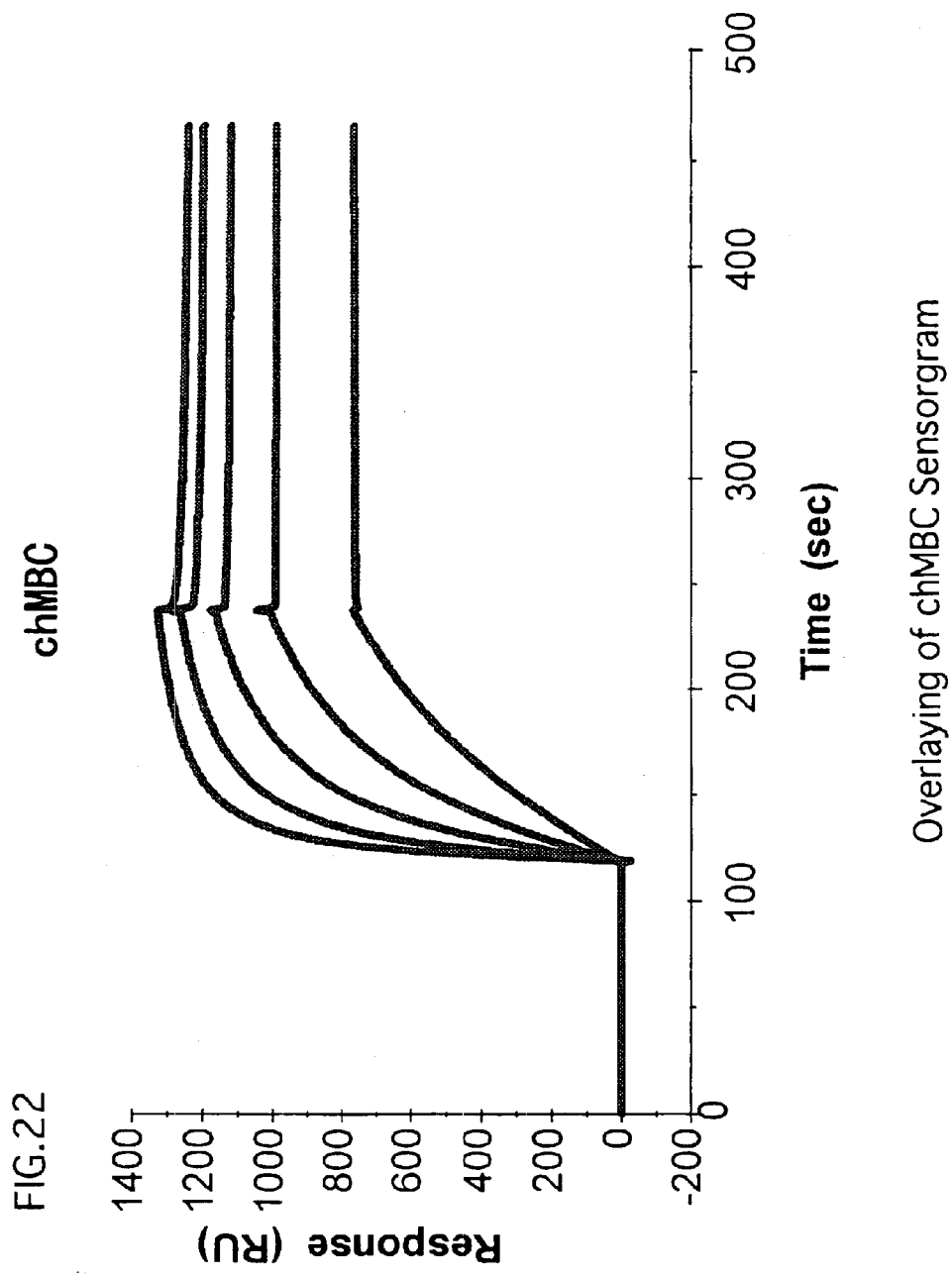
FIG. 22 is a graph showing the results of the kinetic analysis of the antibody according to the invention.
Figure 23:
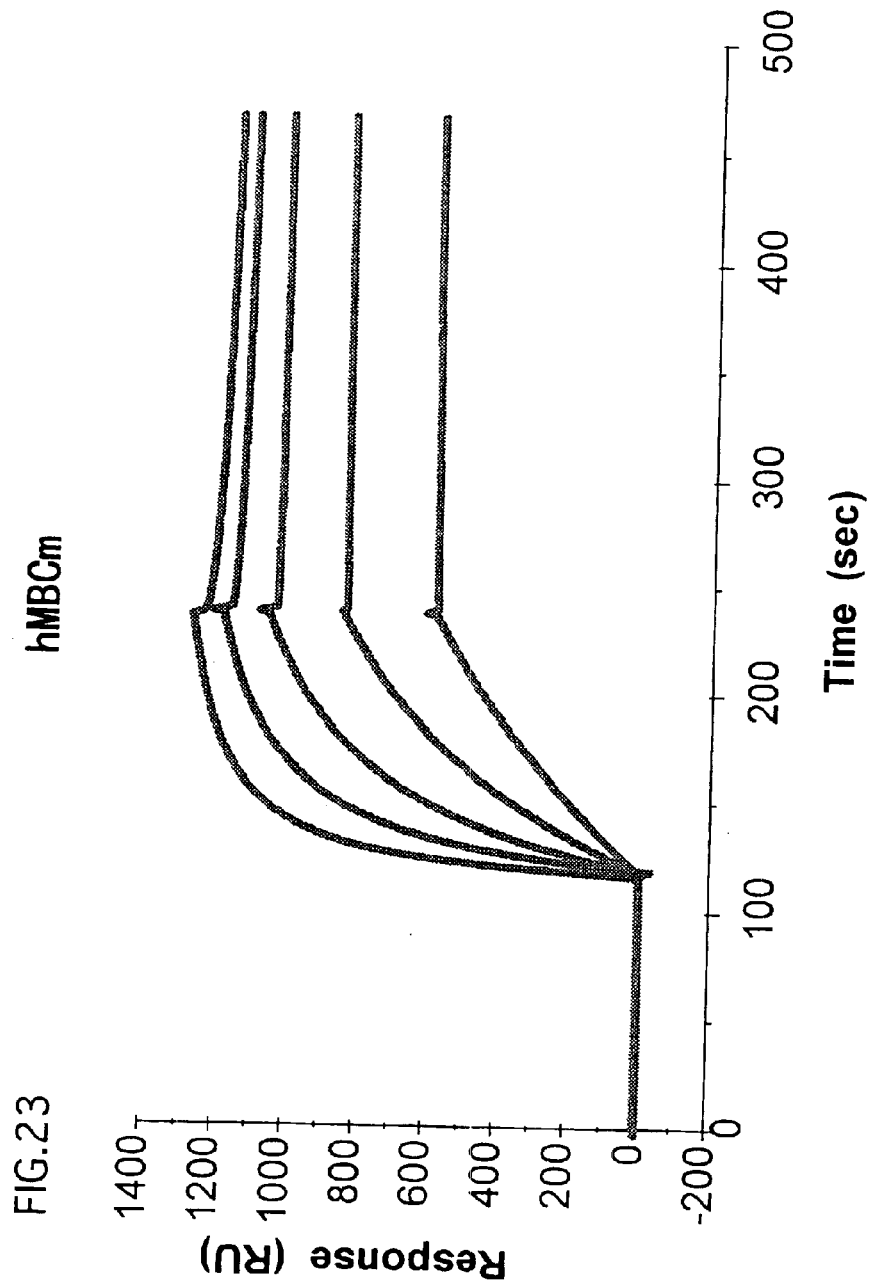
FIG. 23 is a graph showing the results of the kinetic analysis of the antibody according to the invention.
Figure 24:
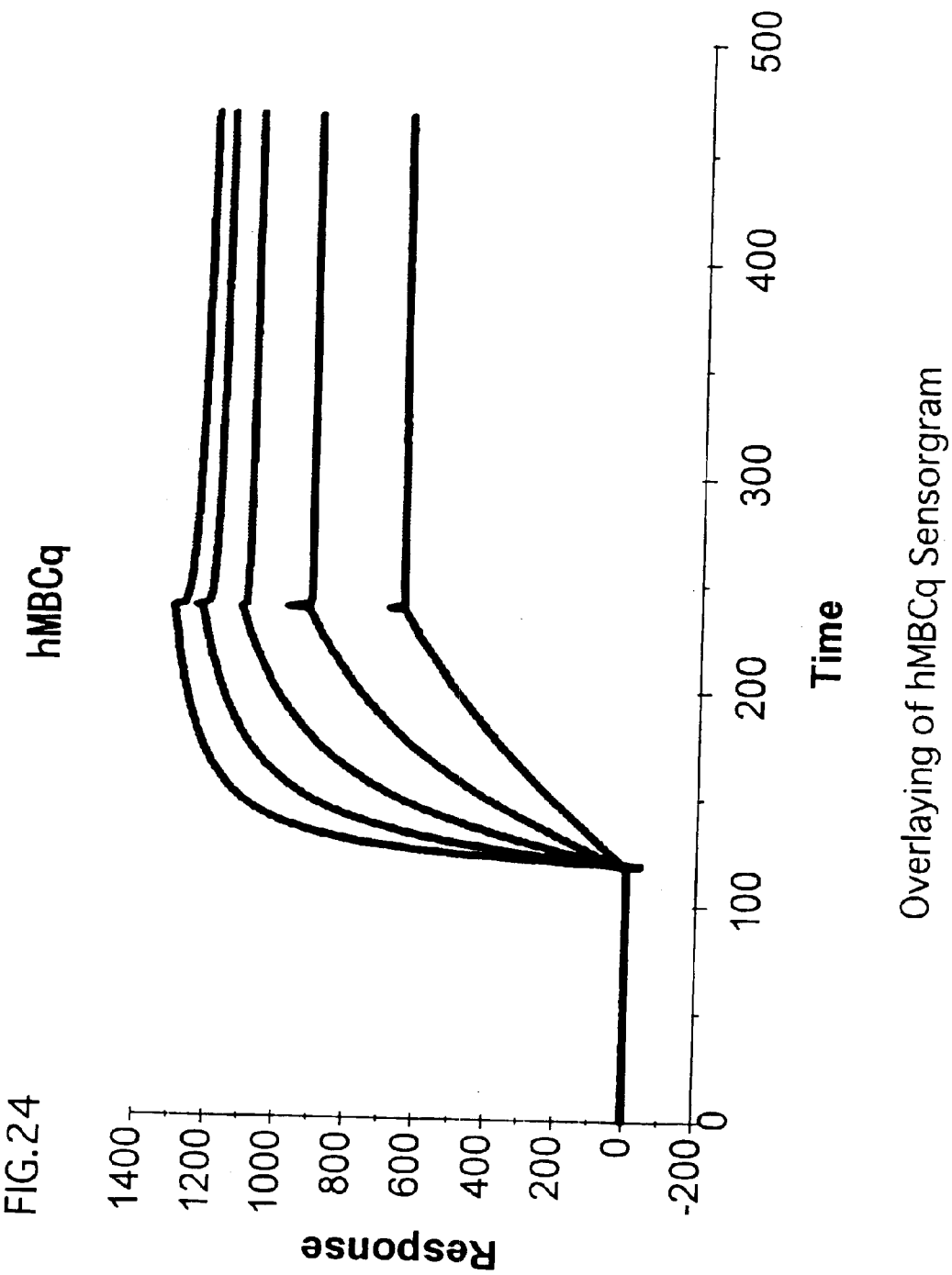
FIG. 24 is a graph showing the results of the kinetic analysis of the antibody according to the invention.

As a running buffer, HBS (10 mM HEPES, pH 7.4; 0.15 M NaCl; 3.4 mM EDTA; 0.005% Surfactant P20) at a flow rate of 5 μl/min. was employed. The calboxyl groups of calboxymethyldextran on the sensor tip CM5 were activated by an injection of 100 μl of 0.05M N-hydroxysuccinimide (NHS)/0.2M N-ethyl-N'-(3-dimethylaminopropyl) carbodiimide hydrochloride (EDC) and an injection of 100 μl of 80 mM 2-(2-pyridinyldithio)ethanamine (PDEA)/0.1 M borate buffer (pH 8.5), and an additional injection of 10 μl of 5 μg/ml PTHrP (1–34+C)/10 mM sodium acetate buffer (pH 5.0) to adsorbe onto the C-terminals of PTHrP (1–34+C) specifically for Cys residues. Subsequently, an injection of 100 μl of 50 mM (L)-cystein/1M NaCl/0.1 M sodium formate buffer (pH 4.3) was conducted to block excessively activated groups. Subsequently, an injection of 10 μl of 0.1M glycine-HCl buffer (pH 2.5) and 10 μl of 10 mM HCl was conducted to wash the substances having non-covalent bonding. The amount of the PTHrP (1–34+C) thus immunolized was 226.4 RU (resonance units) (FIG. 19).

(2) Interaction Between Immunolized PTHrP (1–34+C) and Purified Mouse Anti-PTHrP Antibody As a running buffer, HBS at a flow rate of 20 μl/min. was used. The antibody producing hybridomas were injected into the abdominal cavity of a Ba1b/c mouse and after a couple of weeks, the ascites were collected and applied on protein A column to purify antibodies. The purified #23-57-137-1 antibody was designated "MBC" and the purified 3F5 antibody was designated "3F5". These antibodies were diluted with HBS in a series of concentrations of 1.25, 2.5, 5, 10 and 20 μg/ml.

In the analysis, 40 μl of the antibody solution was injected for 2 min. to give a binding phase, and then HBS was injected for 2 min. to give a dissociation phase. After the dissociation was completed, 10 μl of 10 mM HCl was injected to recover the sensor tip. The analysis was conducted by using this binding-dissociation-recovering as one cycle and injecting various antibody solutions to obtain a sensorgram.

(3) Interaction Between Immobilized PTHrP (1–34+C) and Purified Humanized Anti-PTHrP Antibody As a running buffer, HBS at a flow rate of 20 μl/min. was used. The antibody was produced by CHO cells and purified using protein A column. The purified chimeric antibody was designated "chMBC", and the purified humanized antibodies of versions m and q were designated "hMBCm" and "hMBCq", respectively, These antibodies were diluted with HBS in a series of concentrations of 1.25, 2.5, 5, 10 and 20 μg/ml.

In the analysis, 40 μl of the antibody solution was injected for 2 min. to give a binding phase, and then HBS was injected for 2 min. to give a dissociation phase. After the dissociation was completed, 10 μl of 10 mM HCl was injected to recover the sensor tip. The analysis was conducted by using a binding-dissociation-recovering as one cycle and by injecting various antibody solutions to obtain a sensorgram.

(4) Kinetic Analysis of the Interaction

The date file of interest was read and a comparison of the reaction patterns was conducted by overlaying the reaction regions of interest (FIGS. 20–24). In each of FIGS. 20–24, lines sequentially indicate from the top the data for the antibody concentrations 1.25, 2.5, 5, 10 and 20 μg/ml. Further, kinetic analysis of the interaction was conducted using an analysis software specifically designed for BIA-CORE "BIAevaluation 2.1" (Pharmacia) which is capable of calculating the kinetics parameters (binding rate constant "kass" and dissociation rate constant "kdiss") by curve cutting (Tables 4 and 5).

TABLE 4

Kinetics parameters of MBC and 3F5

|  | MBC | 3F5 |
| --- | --- | --- |
| Kdiss [l/s] | $7.38 \times 10^{-5}$ | $1.22 \times 10^{-2}$ |
| Kass [l/Ms] | $7.23 \times 10^{5}$ | $6.55 \times 10^{5}$ |
| KD [M] | $1.02 \times 10^{-10}$ | $1.86 \times 10^{-8}$ |

TABLE 5

Kinetics parameters of chimeric and humanized antibodies

|  | chH-chλ | hMBCm | hMBCq |
| --- | --- | --- | --- |
| Kdiss [l/s] ($\times 10^{-4}$) | 1.66 | 3.16 | 2.32 |
| Kass [l/Ms] ($\times 10^{6}$) | 1.24 | 0.883 | 1.03 |
| KD [M] ($\times 10^{-10}$) | 1.34 | 3.58 | 2.25 |

In this experiment, for determining the binding rate constant, analysis model type 4 (BIAevaluation 2.1 Software Handbook, A1-A5) was used.

EXAMPLE 9

Suppression of Excretion of Phosphorus in a Model of Malignant Tumor-Associated Hypercalcemia Malignant tumor-associated hypercalcemia (HHM) is a disease caused by the presence of PTHrP and it has been known that PTHrP accelerates bone resorption and calcium resorption in kidney and riniferous tubule, resulting in the development of hypercalcemia. On the other hand, with respect to phosphorus, PTHrP suppress the resorption of phosphorus in the kidney and riniferous tubule, resulting in the development of eliminant action, and therefore clinical HHM patients often develop hypophosphatemia. Here, the effect of humanized anti-PTHrP antibody on excretion of phosphorus in the kidney was examined using malignant tumor-associated hypercalcemia model rats.

As a model animal, a nude rat into which human lung cancer LC-6 (purchased from the Central Institute for Experimental Animals) was transplanted was used. It has been known that a nude rat into which human lung cancer LC-6 was subcutaneously transplanted tends to show an increased calcium concentration in blood was the increase of the tumor volume and, as a result, the rat develops hypercalcemia which is associated with, for example, decrease in body weight and spontaneous activity. Using this model animal, the effect of the humanized anti-PTHrP antibody of the invention on phosphate excretion in the kidney was examined by a renal clearance method based on the below-mentioned fractional excretion of phosphate.

The passage of the human lung cancer LC-6 was conducted using BALB/c-nu/nu nude mice (Nippon Kurea) in vivo. For the evaluation of pharmacological efficacy, 5-weeks-old male F344N/Jcl-rnu nude rats (Nippon Kurea) were purchased and then acclimatized them for 1 week, and the rats of 6-weeks-old were used.

The malignant tumor-associated hupercalcemic model animals were prepared as follows. The human lung cancer LC-6 tumor passaged was excised and then finely cut into 3 mm cube of blocks. The resultant tumor blocks were subcutaneously transplanted under the skin flap of the rats at one piece per rat. About thirty days after the transplantation, when it was confirmed that the tumor volume in each of the rats became satisfactorily large (3000 mm³), the rats to be provided as the malignant tumor-associated hypercalcemia model animals were selected based on calcium concentration in blood and body weight.

The examination of phosphate excretion by a renal clearance method was conducted in the following manner.

(1) Renal Clearance Method

A malignant tumor-associated hypercalcemia model animal was anesthetized with pentobarbital (Nembutal, Dainippon Pharmaceutical Co., Ltd.), fixed supinely onto a incubation mat maintained at 37° C., and inserted a cannula (a polyethylene tube, PE50, Nippon Beckton Dickinson) to its bladder to collect urine. Subsequently, the model animal was inserted a cannula for infusion (a polyethylene tube, PE10, Nippon Beckton Dickinson) to its femoral vein, and then an infusion solution (0.7% inulin, 5% mannitol, 0.2% pentobarbital and 0.9% sodium chloride) was introduced into the model animal through the cannula at a flow rate of 2 ml/hr using an infusion pump (Terufusion syringe pump; STC-525; TERUMO) to infuse the model animal. After equilibrating for 50 min., urine was collected through the cannula for five times at 20 min. intervals (i.e., from period-1 to period-5) to give urine samples. At the intermediate point of time during each urine collection procedure, approximately 0.25 ml of blood samples from the right cervical vein of the model animal were collected using a heparin-treated injection syringe.

(2) Administration of Antibody

During the above-mentioned clearance test, at the point of time where the collection of urine of period-2 was just started, a humanized anti-PTHrP antibody was administered intravenously to the animal in a dose amount of 1 mg/ml/kg.

(3) Determination of Concentration of Inulin and Phosphorus in Urine and Blood

The urine samples obtained at period-1 to period-5 were measured for their volume and then determined for the inulin and phosphorus concentrations thereof. The blood samples also obtained above were subjected to cooling centrifugation to obtain a plasma sample, which was used for determining the inulin and phosphorus concentration. The determination of inulin was conducted by Anthrone-sulfate method (Roe, L. et al., J. Biol. Chem. 178, 839–845, 1949), and the determination of phosphorus was conducted using Hitachi Automatic Analyzer 7170 model with a regent for inorganic phosphorus determination, Autosera IP (Daiichi Pure Chemicals) in accordance with a manual (Physke-Sabaroh method).

(4) Calculation of Inulin Clearance, Phosphorus Clearance and Fractional Excretion of Phosphorus.

Inulin clearance (Cin), phosphorus clearance (Cp) and fractional excretion of phosphorus (FEp) were calculated according to the following equations.

Calculation of Inulin Clearance (Cin):

$$Cin = Uin \cdot V/Pin$$

Wherein Cin represents inulin clearance (ml/kg/min); Uin represents the concentration of inulin in urine (mg/ml); V represents the amount of urine per unit time (ml/kg/min); and Pin represents the concentration of inulin in blood (mg/ml).

Calculation of phosphorus clearance (Cp):

$$Cp=Up\ V/Pp$$

Wherein Cp represents phosphorus clearance (ml/kg/min); Up represents the concentration of phosphorus in urine (mg/ml); V represents the amount of urine per unit time (ml/kg/min); and Pp represents the concentration of phosphorus in blood (mg/ml)

Calculation of fractional excretion of phosphorus (FEp):

$$FEp=Cp/Cin$$

Wherein FEp represents fractional excretion of phosphorus; Cin represents inulin clearance; and Cp represents phosphorus clearance. The examination was conducted using four animals.

The results were determined as the average value±standard error.

Figure 25:
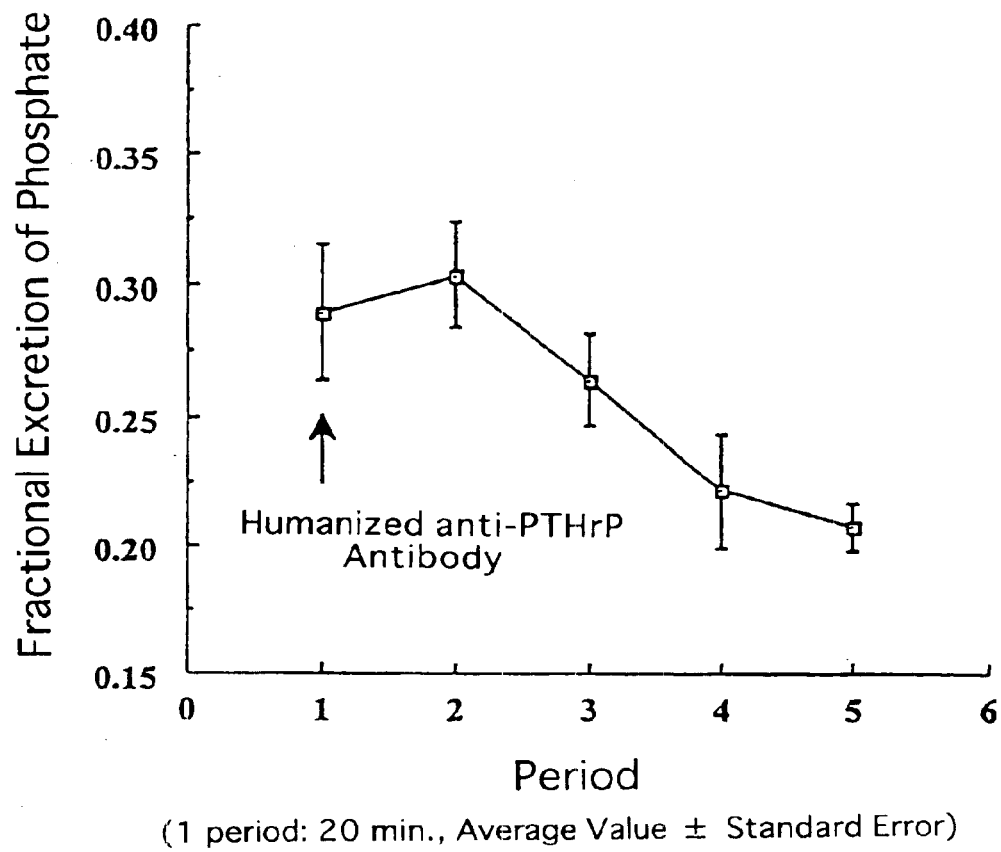
FIG. 25 is a graph showing the test results of the effect of the humanized antibody according to the invention on fractional excretion of phosphate.
Figure 26:
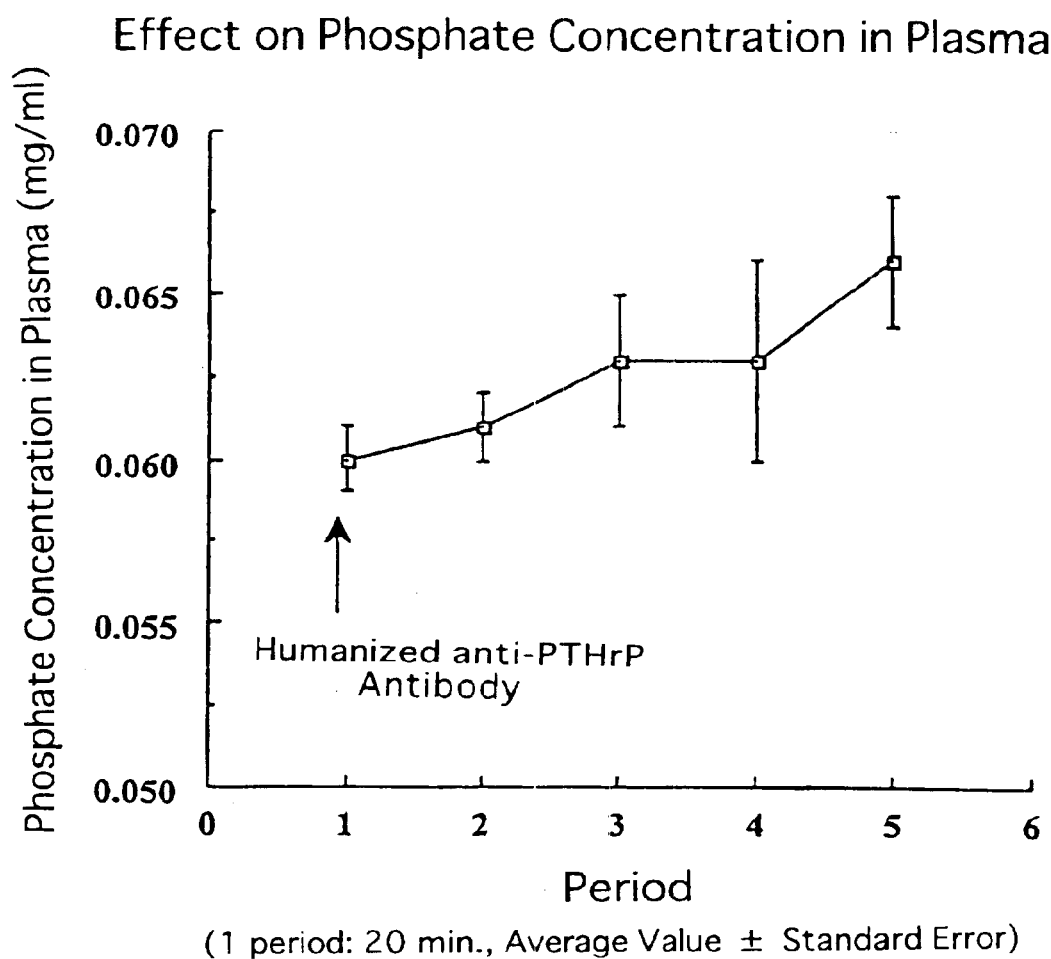
FIG. 26 is a graph showing the test result of the effect of the humanized antibody according to the invention on phosphorus concentration in plasma.

The results of fractional excretion of phosphorus and phosphorus concentration in blood are shown in FIGS. 25 and 26.

FIG. 25 is a graph illustrating the relationship of fractional excretion of phosphorus (=phosphorus clearance/inulin clearance) vs. periods of clearance (1 period=20 min.). The humanized anti-PTHrP antibody (1 mg/kg) was administered (i.v.) at the time of the starting of period-2.

FIG. 26 is a graph illustrating the relationship of phosphorus concentration in plasma vs. periods of clearance (1 period=20 min.). The humanized anti-PTHrP antibody (1 mg/kg) was administered (i.v.) at the time of starting of period-2.

From these results, it was found that the fractional excretion of phosphorus given after administering the antibody (i.e., from period-2 and period-5) was obviously suppressed compared with that given before administering the antibody (i.e., period-1). In other words, it was found that the administration of the neutralizing antibody to a subject developing hypophosphatemia, which causes acceleration of excretion of phosphorus (FEp>0.2) recovered the phosphorus resorption in the subject to approximately the normal level (fractional resorption of phosphate=1-FEp>0.8%) and, as a result, trend to normalcy of the phosphorus concentration in blood of the subject was observed. These results suggest the usefulness of the antibodies of the present invention as agents treating the accelerated excretion of phosphorus and hypophosphatemia caused by the presence of PTHrP.

Since PTHrP is a substrate causing malignant tumor-associated hypercalcemia, the possibility of increase in phosphorus excretion and decrease in high energy organic phosphorus in tissue caused by PTHrP is predicted. Accordingly, various diseases associated with hypophosphatemia, such as hypophosphatemic rickets and hypophosphatemic vitamine D-resistant rickets, are considered to be mainly caused by the increase in phosphorus excreted through urine and, therefore, the antibodies of the present invention would also be useful for treating these diseases.

EXAMPLE 10

Improvement of Various Clinical Symptoms of Malignant Tumor-associated Hypercalcemia It has been known that the malignant tumor-associated hypercalcemia is caused by the presence of PTHrP which is produced by the tumor and that PTHrP accelerates bone resorption and calcium resorption in the kidney and the uriniferous tubule, leading to hypercalcemia. Further, in a patient suffering from hypercalcemia, worsening of clinical symptoms, such as poor performance status, loss of consciousness, systemic malaise, hydrodipsia, nausea and emesis (anorexia) are observed. The effect of the anti-PTHrP antibody on such clinical symptoms was examined using hypercalcemia model animals of human tumor nude mouse transplantation system and human tumor-nude rat transplantation system.

As the hypercalcemia model animal, nude mice and nude rats into which human lung cancer LC-6 (purchased from the Central Institute for Experimental Animals) had been transplanted were used. Nude mice and nude rats into which human lung cancer LC-6 is transplanted tend to show increased calcium concentration in blood with increase in the tumor volume, leading hypercalcemia associated with decrease in body temperature and body weight.

The improvement effect of mouse anti-PTHrP antibody on general clinical symptoms of malignant tumor-associated hypercalcemia was examined using a human lung cancer LC-6-nude mouse transplantation system and its result is shown photographically. The effect of the antibody on improvement of decrease in spontaneous activity, body temperature and anorexia was examined using a human lung cancer LC-6-nude mouse transplantation system.

1. Improvement of Apparent Clinical Symptoms Associated With Hypercalcemia

The passage of the human lung cancer strain LC-6 was conducted using BALB/c-nu/nu nude mice (Nippon Kurea) in vivo. For the evaluation of pharmacological efficacy, 5-weeks-old male BALB/c-nu/nu nude mice (Nippon Krea) were purchased and then acclimatized for 1 week, and the mice of 6-weeks-old were used.

The hypercalcemia model mice were prepared and divided into groups in the following manner. The human lung cancer LC-6 passaged was excised and then finely cut into 3 mm cube of blocks. The resultant tumor blocks were subcutaneously transplanted under the skin flap of the mice at one piece per mouse. Twenty-seven days after the transplantation, when it was confirmed that the tumor volume in each of the mice became satisfactorily large, the mice were divided into groups so that the tumor volume, the calcium concentration in blood and the body weights of the mice of the individual groups were averaged, and the mice were provided as the hypercalcemia model animals.

The tumor volume was determined by measuring the major diameter (a mm) and the minor diameter (b mm) of the tumor and calculating using the both measured values according to Galant's equation [ab$^2$/2].

The calcium concentration in blood was determined as ionized calcium concentration in whole blood by drawing blood from each of the mice via the orbit using a hematocrit tube and applying the blood to 643 Automatic Ca$^{++}$/pH Analyzer (CIBA-CORNING).

The examination of therapeutic efficacy of the antibody on hypercalcemia was conducted in the following manner. The mouse antibody against PTHrP was administered to each of the above-mentioned hypercalcemia model animal via the tail vein on day 27, 30, 34 and 37 after transplanting the tumor in a dose amount of 100 μg per mouse. For preparation of controls, a phosphate buffered-physiological saline was administered instead of the antibody in the same manner. On 41 days after transplanting the tumor, from each of the antibody-administered group and the control group, a typical mouse was selected and a picture was taken thereof along with a normal mouse.

Figure 27:
FIG. 27 is a photograph showing the apparent clinical symptoms of hypercalcemia model mice developed after administration of the anti-PTHrP antibody according to the invention (morphology of living animal)
Figure 28:
FIG. 28 is a photograph showing the apparent clinical symptoms of hypercalcemia model mice developed after administration of the anti-PTHrP antibody according to the invention (morphology of living animal)

As a result, in the hypercalcemia model animal transplanted with human lung cancer LC-6, although the antibody-administered mice (shown in center of each of FIGS. 27 and 28) bore the same level of tumor mass as the control mouse (shown in the right of each of FIGS. 27 and 28), they exhibited the same level of appearance as the normal mouse (shown in the left of FIGS. 27 and 28). This result suggest that the administration of the anti-PTHrP antibody exerts an improvement in apparent-clinical symptoms (FIGS. 27 and 28).

2. Improvement of Spontaneous Activity Decrease Associated With Hypercalcemia

The passage of the human lung cancer LC-6 was conducted using BALB/c-nu/nu nude mice (Nippon Kurea) in vivo. For the evaluation of pharmacological efficacy, 5-weeks-old male F344/N Jcl-run nude rats (Nippon Krea) were purchased and then acclimatized for 1 week, and the rats of 6-weeks-old were used.

The hypercalcemia model animals were prepared in the following manner. The human lung cancer LC-6 passaged was excised and then finely cut into 3 mm cube of blocks. The resultant tumor blocks were subcutaneously transplanted under the skin flap of the mice at one piece per mouse. About thirty days after the transplantation, when it was confirmed that the tumor volume in each of the mice had become satisfactorily large, the mice were divided into groups so that the tumor volume, the calcium concentration in blood and the body weights of the mice of the individual groups were averaged, and the mice were provided as the hypercalcemia model animals.

The calcium concentration in blood was determined as ionized calcium concentration in whole blood by drawing blood from each of the mice via the orbit using a hematocrit tube and applying the blood to 643 Automatic $Ca^{++}$/pH Analyzer (CIBA-CORNING).

(1) Method for Determination Of Spontaneous Activity

The determination of spontaneous activity was conducted using ANIMEX activity meter type SE (FARAD, Electronics, Sweden), which was placed in predetermined position in the polyethylene cage in which each of the model animals was individually nurtured (watering and feeding). This apparatus was designed to measure the amount of movement of each rat. Using this apparatus, the amount of movement was recorded as the count per a definite time of period. The measurement was conducted for 13 hours (from 7:00 p.m. of a certain day to 8:00 a.m. of next day) and the results were given as count per hour.

(2) Administration of Antibody

The humanized anti-PTHrP antibody was administered each of the above-prepared rats which developed hypercalcemia via its tail vein as a control in a dose amount of 5 mg/0.5 ml/kg. Saline was administered to another group of the rats in the same manner. The measurement was conducted with alternation of an antibody-administrated rat and a control rat.

The measurement was conducted on day 0 (i.e., the day before administration), 2, 4, 7 and 14 for the antibody-administered rats and on day 1, 3, 5, 8 and 15 for the control rats.

Figure 29:
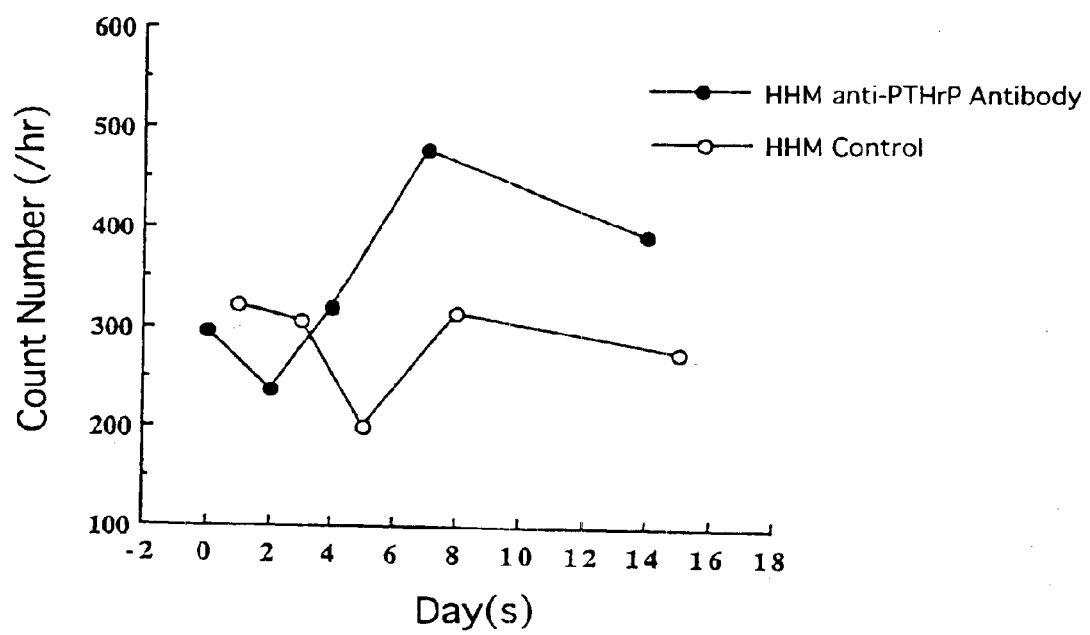
FIG. 29 is a graph showing the change in spontaneous activity of a hypercalcemia model animal over time after administering the anti-PHTHrP antibody according to the invention in comparison with that of a control model animal administered with physiological saline.

As a result, the control rats showed no change or a decrease in spontaneous activity during the test period, whereas the antibody-administered rats showed an increase in spontaneous activity on and after day 4 of the administration (FIG. 29).

3. Improvement in Body Temperature Decrease Associated With Hypercalcemia

The passage of human lung cancer LC-6 and the preparation of the malignant tumor-associated hypercalcemia model animals were conducted in the same manner as in step 2 above.

(1) Method for Measuring Body Temperature

The measurement of body temperature was conducted using a digital thermometer by anesthetizing the animal with pentobarbital (Nembutal, Dainippon Pharmaceutical Co., Ltd.) and inserting a temperature sensor into the rectum thereof.

(2) Administration of Antibody

The humanized anti-PTHrP antibody was administered to each of the above-mentioned hypercalcemia model rats via the tail vein in a dose amount of 1 mg/ml/kg. For a control, saline was administered to another model rat via the tail vein. Further, a normal rat to which no antibody was administered was also measured for its body temperature. The measurement of body temperature of the rats was conducted on day 0 (i.e., the day of the administration), 1, 2 and 3 after the administration with respect to all of the antibody-administered rats, the control rat and the normal rat.

Figure 30:
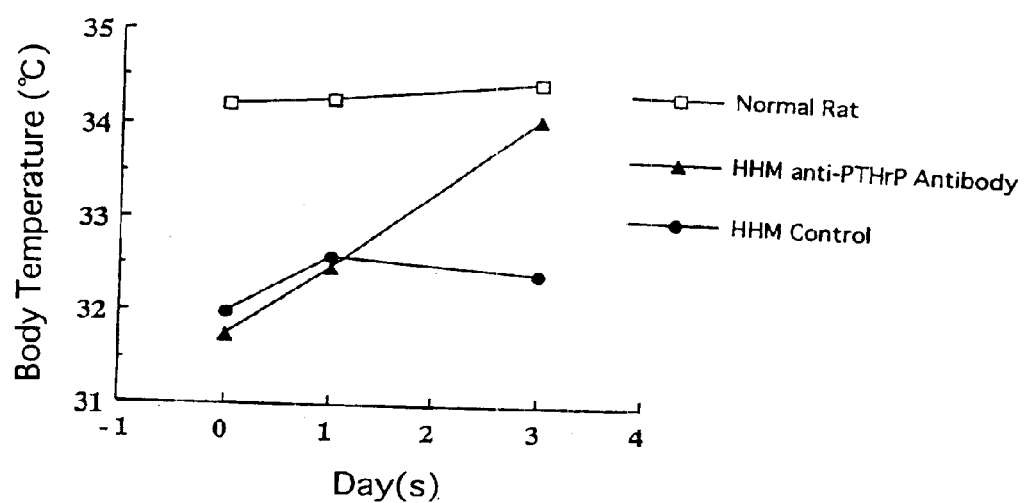
FIG. 30 is a graph showing the change in body temperature of a hypercalcemia model animal over time after administering the anti-PHTHrP antibody according to the invention in comparison with that of a control model animal administered with physiological saline.

As a result, the normal rat showed no change in body temperature (34.2–34.4° C.) throughout the test period, whereas the malignant tumor-associated hypercalcemia model rats showed a decrease in body temperature by about 2° C. compared with the normal rats. When the humanized anti-PTHrP antibody was administered to the model rats, it was confirmed that the malignant tumor-associated hypercalcemia model rats recover their decreased body temperatures to the same level as that of the normal rats three days after administration. These results suggests that the humanized anti-PTHrP antibody of the present invention is effective for improving the body temperature decrease of the malignant tumor-associated hypercalcemia model animal (FIG. 30).

4. Improvement in Food Intake Decrease Induced

The passage of the human lung cancer LC-6 and the preparation of the hypercalcemia model animals were conducted in the same manner as described in above section 2. The model animals prepared were divided into groups so that the calcium concentration in blood and the body weights of the mice of the individual groups were averaged, and the mice were used in the experiments below.

(1) Measurement of Amount of Feed Intake

During the test period, the rats were individually placed into a metabolic cage and nurtured with water and feed. With respect to each of the rats, the amount ingested was determined as the amount (g) per 24 hours (starting from 9:00 a.m. of a certain day to 9:00 a.m. of the next day). The determination was conducted by measuring the total weight of the feedstock container both at 9:00 a.m. of the day (i.e., tare) and at 9:00 a.m. of the next day and calculating the weight difference therebetween.

(2) Administration of Antibody

The humanized anti-PTHrP antibody was administered to each of the hypercalcemia model rats (HHM rats) described above via its tail vein in a dose amount of 5 mg/0.5 ml/kg. Saline was administered to each of control group via its tail vein in the same manner. Saline was also administered to each of normal rats via tail vein in the same manner. With respect to all of the antibody-administered rats, the control rats and the normal rats, the determination of the amount of food intake was conducted on day 0 (i.e., previous day of the administration to the day of the administration), day 1 (i.e., period from the day of the administration to the next day), day 3 (i.e., period from three days after the administration to the next day) and day 5 (i.e., period from five days after the administration to the next day).

As a result, before administering the antibody, the amount ingested by the hypercalcemia model rats (5–9 rats) was 8.11 g in average, whereas that of the normal rats was 12.06 g in average, which demonstrates an obvious decrease in the amount of ingestion by hypercalcemia model rats. When the humanized ante-PTHrP antibody was administered to the model rats, on and after the day after administering the antibody, although almost no change was observed in the amount of ingestion by the control rats, the amount of ingested by the antibody-administered rats recovered to the same level of that in the normal rats. These results suggest that the humanized anti-PTHrP antibody of the present invention is effective in improving the decrease in the amount ingested for the malignant tumor-associated hypercalcemia model (Table 6).

TABLE 6

Effect on ingestion

| Individual | | | Eating amount of individual (g) | | | |
|---|---|---|---|---|---|---|
| Animal | No. | Administration* | day 0 | day 1 | day 3 | day 5 |
| Normal rat | 1 | Saline | 13.7 | 16.7 | 18.63 | 18.71 |
| | 2 | Saline | 14.27 | 15.3 | 19.55 | 19.39 |
| | 3 | Saline | 9.83 | 15.5 | 20.72 | 19.88 |
| | 4 | Saline | 10.42 | 15.04 | 20.28 | 22.03 |
| HHM rat | 5 | Saline | 10.77 | 14.24 | 12.66 | 11.82 |
| | 6 | Saline | 6.99 | 8.92 | 2.59 | 14.8 |
| HHM rat | 7 | Anti-PTHrP antibody | 7.46 | 17.65 | 22.52 | 17.99 |
| | 8 | Anti-PTHrP antibody | 12 | 12.38 | 20.94 | 23.1 |
| | 9 | Anti-PTHrP antibody | 3.35 | 16.65 | 20.36 | 21.89 |

*Administration of saline (Saline): 0.5 ml/kg, via tail vein; and Administration of antibody: 5 mg/0.5 ml/kg, via tail vein.

From the above-mentioned results, it was demonstrated that the chimeric antibodies and the humanized antibodies of the present invention are useful as agents for improving the various clinical symptoms of malignant tumor-associated hypercalcemia.

5. Improvement of Decrease in Blood pH Induced by Hypercalcemia

The passage of human lung cancer LC-6 and the preparation of the malignant tumor-associated hypercalcemia model animals were conducted in the same manner as in step 2 above. The model animals were divided into groups so that the calcium concentration in blood and the body weight of the mice of the individual groups were averaged.

(1) Determination of Blood pH

Blood was collected from each test animal using a heparin-treated injection syringe by cardiac blood drawing technique and then applying the resultant blood sample to 643 Automatic $Ca^{++}$/pH Analyzer (CIBA-CORNING) to determine pH of the blood sample.

(2) Administration of Antibody

The humanized anti-PTHrP antibody was administered to each of the above-mentioned hypercalcemia model rats (HHM rats) via its tail vein in a dose amount of 5 mg/0.5 ml/kg (n=3). Saline was administered to each of control group via its tail vein in w the same manner (n=2). With respect to any of the antibody-administered rats and the control rats, the determination of blood pH was conducted on day 0 (i.e., the day of administration), day 1 and day 7. The results are given as average of the pH values obtained.

Figure 31:
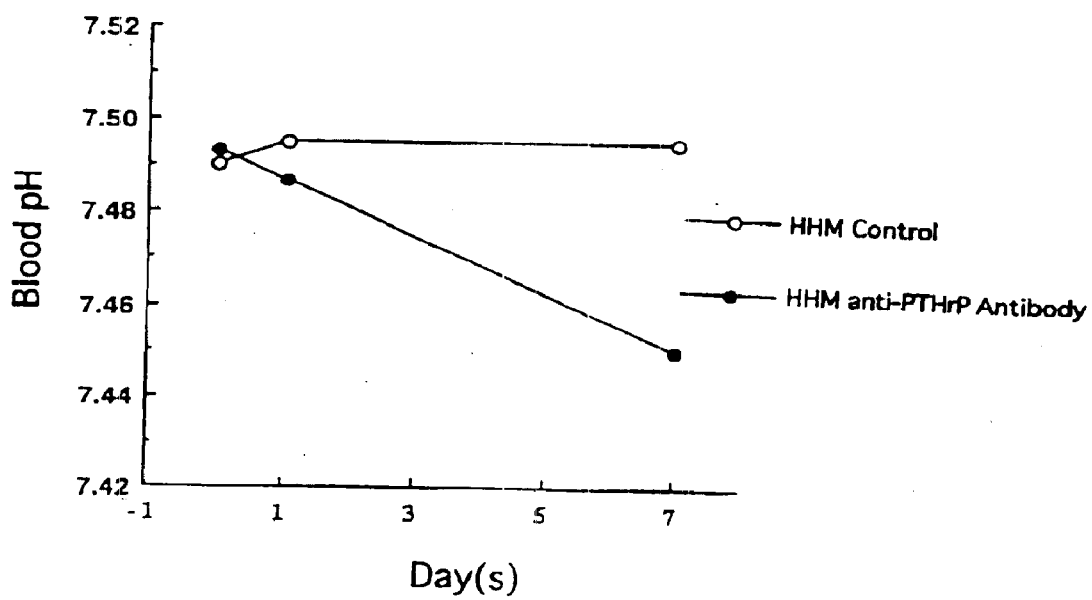
FIG. 31 is a graph showing the change in blood pH of a hypercalcemia model animal over time after administering the anti-PHTHrP antibody according to the invention in comparison with that of a control model animal administered with physiological saline.

As a result, before administering the antibody, the pH of the blood obtained from the hypercalcemic model rats was about 7.49 (whereas that from the normal rats was 7.40±0.02), which means that the model rats obviously had developed metabolic alkalosis. When the humanized anti-PTHrP antibody of the present invention was administered to the model rats, although the control rats showed almost no change in blood pH, the antibody-administered rats showed such an improvement in pH values that the pH values recovered to near the pH value of the normal rats seven days after administering the antibody. As one of the clinical symptoms of malignant tumor-associated hypercalcemia (HHM), metabolic alkalosis has been reported which is known to be induced by the inhibition of excretion of bicarbonate ion ($HCO_3^-$) in kidney. Since the administration of the humanized anti-PTHrP antibody of the present invention normalized the blood pH in the hypercalcemia model animals, it is suggested that the antibody can improve the metabolic alkalosis found in HHM (FIG. 31).

From the results mentioned above, it was demonstrated that the chimeric antibodies and the humanized antibodies of the present invention are useful as agents for improving the clinical symptoms of malignant tumor-associated hypercalcemia.

INDUSTRIAL APPLICABILITY

According to the present invention, a chimeric antibody and a humanized antibody against PTHrP are provided. These antibodies have a low antigenicity against human and therefore are useful as agents for treating hypercalcemia, hypophosphatemia and the like.

What is claimed is:

1. An isolated polypeptide comprising an L chain V region of a humanized antibody comprising an amino acid sequence chosen from SEQ ID NOs: 48–51.

2. An isolated polypeptide comprising an L chain V region of a humanized antibody comprising an amino acid sequence chosen from SEQ ID NOs: 52–55.

3. An isolated polypeptide comprising an H chain V region of a humanized antibody comprising an amino acid sequence as shown in SEQ ID NO: 56.

4. An isolated L chain of a humanized antibody which binds to a human parathyroid hormone related protein, comprising a polypeptide comprising an L chain C region of a human antibody and a polypeptide comprising an L chain V region according to claim 1 or 2.

5. An isolated H chain of a humanized antibody which binds to a human parathyroid hormone related protein, comprising a polypeptide comprising an H chain C region of a human antibody and a polypeptide comprising an H chain V region according to claim 3.

6. An isolated humanized antibody comprising an L chain of a humanized antibody according to claim 4 and an H chain of a humanized antibody according to claim 5, wherein the humanized antibody binds to a human parathyroid hormone related protein.

7. An agent for suppressing hypercalcemia comprising the humanized antibody of claim 6 as an effective ingredient.

8. An agent for suppressing hypercalcemia associated with malignant tumor, comprising the humanized antibody of claim 6 as an effective ingredient.

9. The agent for suppressing hypercalcemia according to claim 8, wherein the malignant tumor is at least one chosen from cancer of the pancreas, lung cancer, cancer of the pharynx, cancer of the larynx, cancer of the tongue, cancer of the gingiva, cancer of the esophagus, cancer of the stomach, cancer of the biliary duct, cancer of the breast, cancer of the kidney, cancer of the urinary bladder, cancer of the uterus and prostate cancer, and malignant lymphoma.

10. An agent for improving hypophosphatemia comprising, as an active ingredient, a substance capable of inhibiting the binding between parathyroid hormone related protein (PTHrP) and a receptor thereof, wherein the substance is the humanized antibody of claim 6.

11. A method of inhibiting the binding between PTHrP and a receptor thereof, comprising:

combining the humanized antibody of claim 6 with the PTHrP;

allowing said humanized antibody to bind to PTHrP; and inhibiting the binding of PTHrP to a PTHrP receptor.

* * * * *